US009615987B2

(12) United States Patent
Worm et al.

(10) Patent No.: US 9,615,987 B2
(45) Date of Patent: Apr. 11, 2017

(54) MULTI-POSITION LIMB HOLDER

(75) Inventors: Dustin L. Worm, Plainwell, MI (US); Everett S. Kettle, Portage, MI (US); Mike S. Rozewicz, Mattawan, MI (US); Dave J. Veldkamp, Grand Rapids, MI (US); John R. Fossez, Frisco, TX (US)

(73) Assignee: Stryker Corporation, Kalamazoo, MI (US)

( * ) Notice: Subject to any disclaimer, the term of this patent is extended or adjusted under 35 U.S.C. 154(b) by 718 days.

(21) Appl. No.: 13/554,010

(22) Filed: Jul. 20, 2012

(65) Prior Publication Data
US 2013/0019883 A1 Jan. 24, 2013

Related U.S. Application Data

(60) Provisional application No. 61/510,843, filed on Jul. 22, 2011.

(51) Int. Cl.
*A61G 13/12* (2006.01)
*A61F 5/37* (2006.01)
*A61G 13/10* (2006.01)
*A61B 17/02* (2006.01)

(52) U.S. Cl.
CPC ...... *A61G 13/1245* (2013.01); *A61B 17/0206* (2013.01); *A61G 13/101* (2013.01); *A61G 13/125* (2013.01); *A61G 13/129* (2013.01); *A61B 2017/0268* (2013.01); *A61G 13/124* (2013.01); *A61G 13/1235* (2013.01); *A61G 2203/78* (2013.01)

(58) Field of Classification Search
CPC .................................................. A61G 13/1245

USPC ..... 128/846, 869, 882; 5/600, 621, 624, 623
See application file for complete search history.

(56) References Cited

U.S. PATENT DOCUMENTS

| | | | |
|---|---|---|---|
| 1,516,795 A | | 11/1924 | Schwarting |
| 2,418,561 A | * | 4/1947 | Stallcup ...................... 128/877 |
| 4,232,681 A | | 11/1980 | Tulaszewski |
| 4,407,277 A | | 10/1983 | Ellison |
| 4,426,071 A | | 1/1984 | Klevstad |
| 4,428,571 A | | 1/1984 | Sugarman |
| 4,443,005 A | | 4/1984 | Sugarman et al. |
| 4,564,164 A | | 1/1986 | Allen et al. |
| 4,615,516 A | | 10/1986 | Stulberg et al. |

(Continued)

OTHER PUBLICATIONS

International Search Report and Written Opinion dated Oct. 10, 2012 in International Patent Appl. No. PCT/US2012/047582.

(Continued)

*Primary Examiner* — Tarla Patel
(74) *Attorney, Agent, or Firm* — Lerner, David, Littenberg, Krumholz & Mentlik, LLP

(57) ABSTRACT

A limb holder generally includes a limb holder assembly, a sled or yoke assembly, a pylon and support bar assembly, a clamp assembly, and a retractor assembly. A limb, such as a leg, is supported by the limb holder. The limb holder is supported by a sled which can move along a support bar that is supported by virtue of a mounting pylon. The mounting pylon is fixed in place by a clamp assembly, the clamp assembly being attached directly to a bed, table, or other patient support. The limb holder can also receive one or more retractor assemblies capable of retracting an incision, such that a user may manipulate a patient's limb during a procedure in which the use of retractors is desired.

15 Claims, 68 Drawing Sheets

(56) References Cited

U.S. PATENT DOCUMENTS

| | | |
|---|---|---|
| 4,809,687 A | 3/1989 | Allen |
| 5,001,739 A | 3/1991 | Fischer |
| 5,007,912 A | 4/1991 | Albrektsson et al. |
| 5,025,802 A | 6/1991 | Laico et al. |
| 5,027,799 A | 7/1991 | Laico et al. |
| 5,056,535 A | 10/1991 | Bonnell |
| 5,290,220 A | 3/1994 | Guhl |
| 5,369,827 A | 12/1994 | Parke et al. |
| 5,462,551 A | 10/1995 | Bailey et al. |
| 5,514,143 A | 5/1996 | Bonutti et al. |
| 5,560,577 A | 10/1996 | Keselman |
| 5,582,379 A | 12/1996 | Keselman et al. |
| 5,645,079 A | 7/1997 | Zahiri et al. |
| 5,775,334 A | 7/1998 | Lamb et al. |
| 5,799,349 A | 9/1998 | Petersen |
| 5,802,641 A | 9/1998 | Van Steenburg |
| 5,918,330 A | 7/1999 | Navarro et al. |
| 5,961,085 A | 10/1999 | Navarro et al. |
| 6,058,534 A | 5/2000 | Navarro et al. |
| 6,234,173 B1 | 5/2001 | Hajianpour |
| 6,263,531 B1 | 7/2001 | Navarro et al. |
| 6,622,980 B2 | 9/2003 | Boucher et al. |
| 6,663,055 B2 | 12/2003 | Boucher et al. |
| 6,704,959 B2 | 3/2004 | Schuerch |
| 6,874,184 B2 | 4/2005 | Chandler |
| 7,243,654 B2 | 7/2007 | Schuerch |
| 7,246,390 B2 | 7/2007 | Mitsuishi et al. |
| 7,316,040 B2 | 1/2008 | Siccardi et al. |
| 7,337,483 B2 | 3/2008 | Boucher et al. |
| 7,380,299 B1 | 6/2008 | DeMayo |
| 7,458,933 B2 * | 12/2008 | LeVahn ............ A61B 17/02 600/227 |
| 7,665,167 B2 | 2/2010 | Branch et al. |
| 7,740,016 B1 | 6/2010 | Pigg |
| 7,827,992 B2 | 11/2010 | Sieber |
| 7,832,401 B2 * | 11/2010 | Torrie ............ A61G 13/0036 128/845 |
| 7,947,006 B2 | 5/2011 | Torrie et al. |
| 7,947,862 B2 | 5/2011 | Livorsi |
| 7,985,227 B2 | 7/2011 | Branch et al. |
| 8,020,559 B2 | 9/2011 | Lacriox |
| 2003/0154550 A1 | 8/2003 | Murphy et al. |
| 2004/0133984 A1 | 7/2004 | Mahoney et al. |
| 2005/0278851 A1 | 12/2005 | DeMayo |
| 2006/0225743 A1 | 10/2006 | Schuerch |
| 2007/0251011 A1 | 11/2007 | Matta et al. |
| 2008/0132818 A1 | 6/2008 | Livorsi |
| 2008/0172791 A1 | 7/2008 | Walczyk |
| 2008/0289636 A1 | 11/2008 | Lacroix |
| 2009/0235457 A1 | 9/2009 | Harvey |
| 2009/0293884 A1 * | 12/2009 | DaSilva ............ 128/845 |
| 2009/0308400 A1 | 12/2009 | Wilson et al. |
| 2010/0018537 A1 * | 1/2010 | Soto et al. ............ 128/845 |
| 2010/0071704 A1 | 3/2010 | Domondon |
| 2010/0154121 A1 | 6/2010 | Swain, Jr. |
| 2010/0163055 A1 | 7/2010 | Wilkinson |
| 2010/0192961 A1 | 8/2010 | Amiot et al. |
| 2010/0242181 A1 | 9/2010 | Bochner et al. |
| 2010/0263129 A1 | 10/2010 | Aboujaoude |
| 2010/0313897 A1 | 12/2010 | Schaeffer |
| 2011/0023893 A1 | 2/2011 | Striggow et al. |
| 2011/0030698 A1 | 2/2011 | Kaufman et al. |
| 2011/0048428 A1 | 3/2011 | Hunter, Jr. |
| 2011/0112455 A1 | 5/2011 | Rocklin |
| 2011/0130688 A1 | 6/2011 | Nakamura et al. |
| 2011/0185506 A1 | 8/2011 | Broens |
| 2011/0247632 A1 | 10/2011 | Gehrke |
| 2011/0253151 A1 | 10/2011 | Tochigi et al. |

OTHER PUBLICATIONS

Canadian Office Action for Application No. 2,842,675 dated Feb. 16, 2015.

* cited by examiner

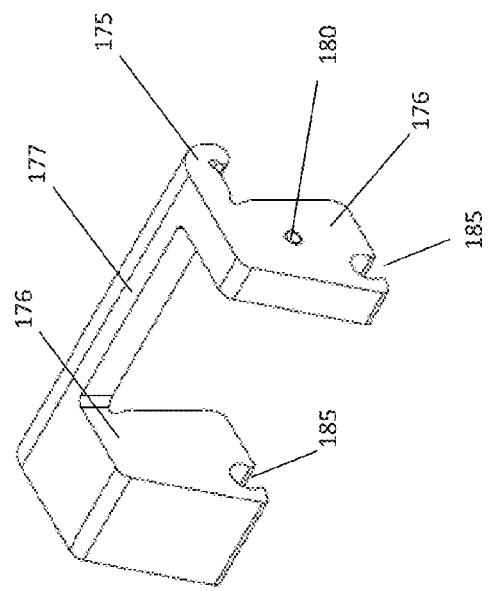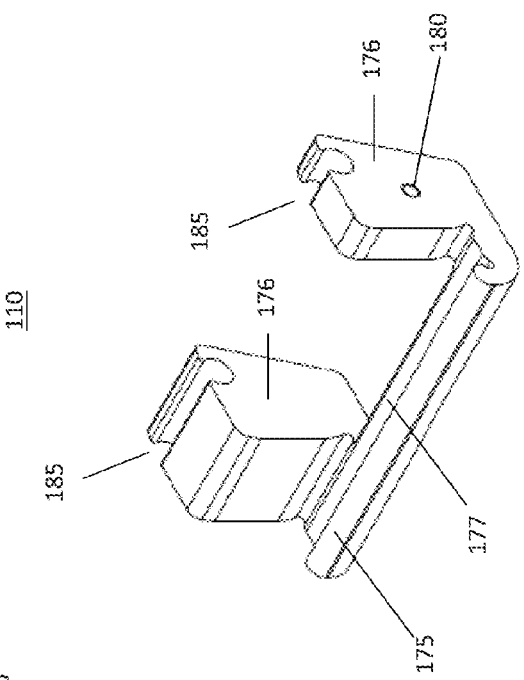
FIG. 5A
FIG. 5B

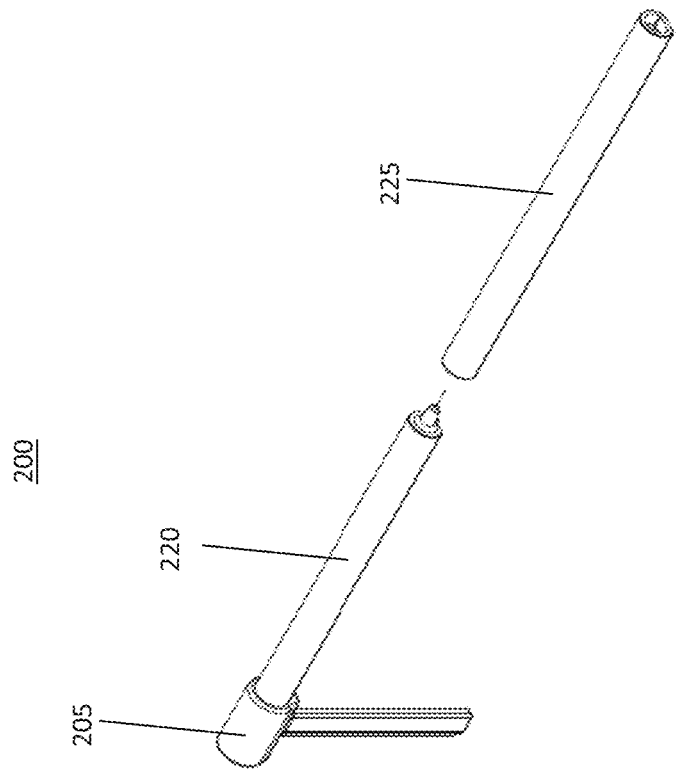
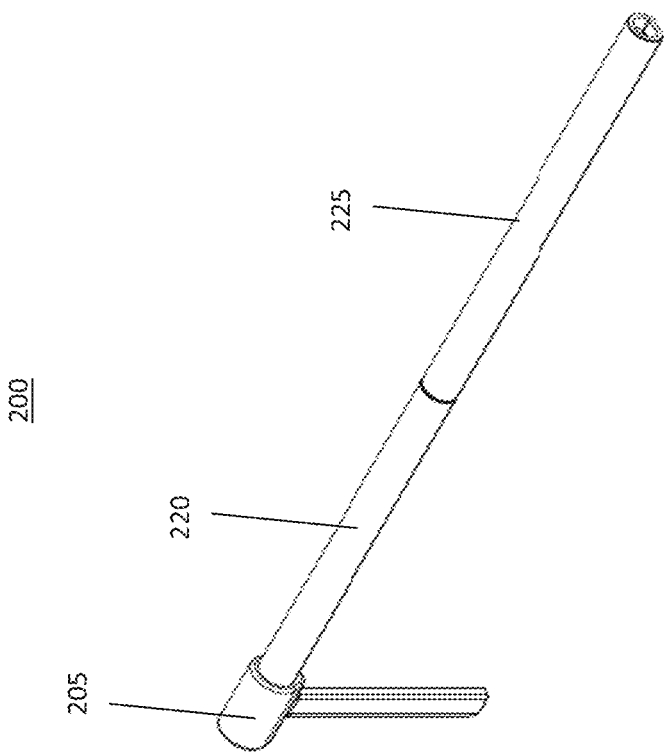

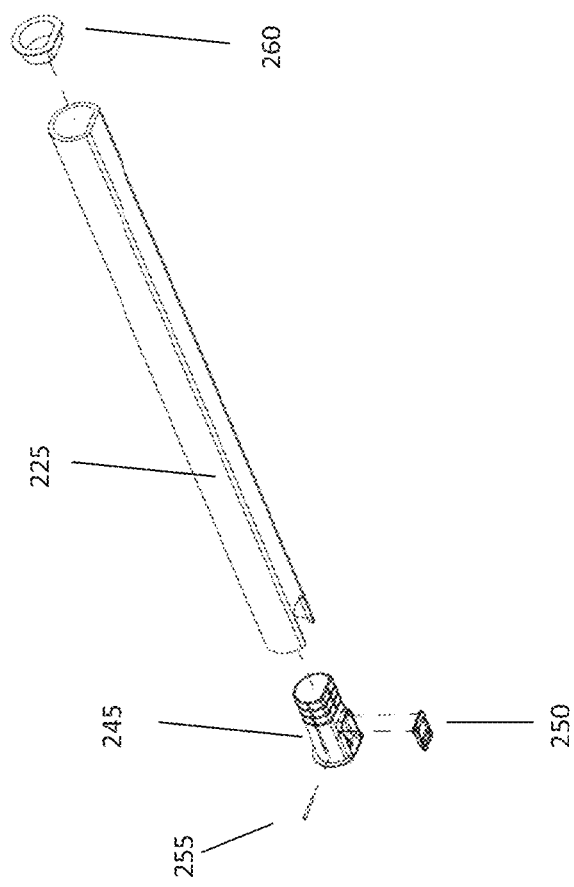
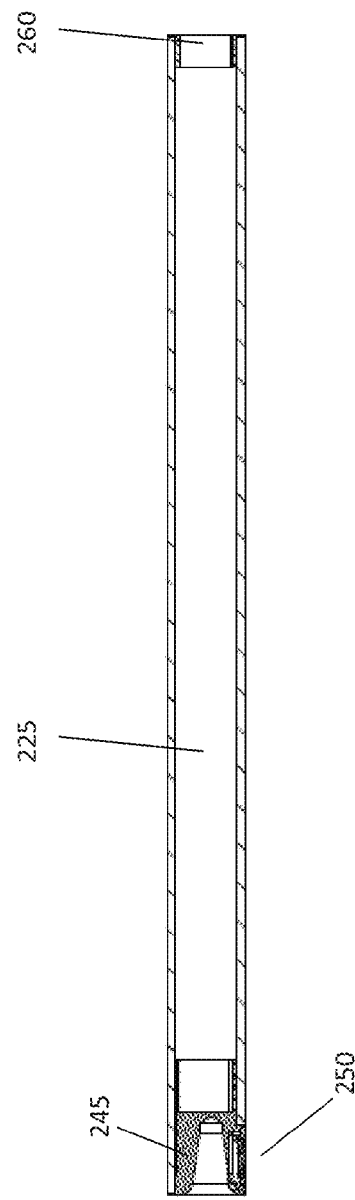

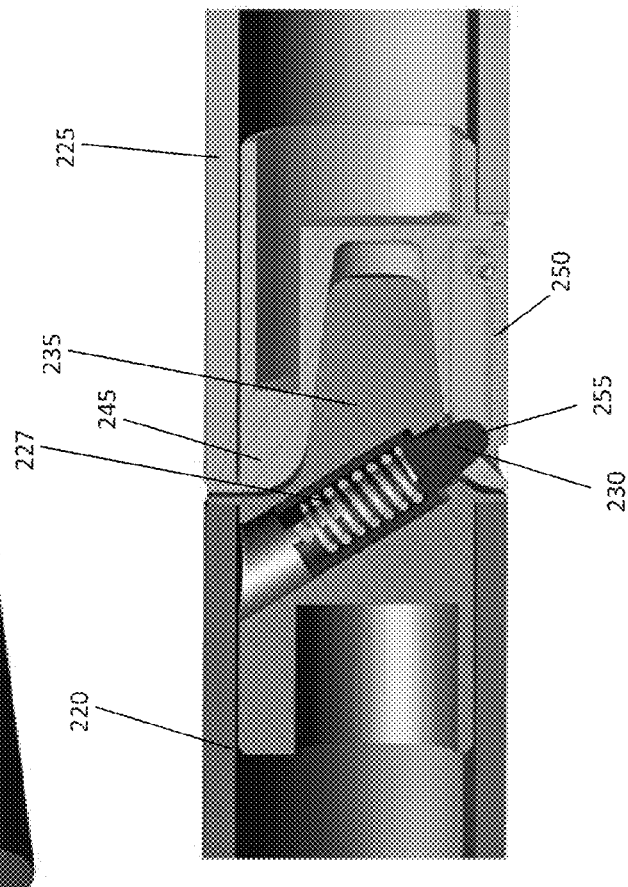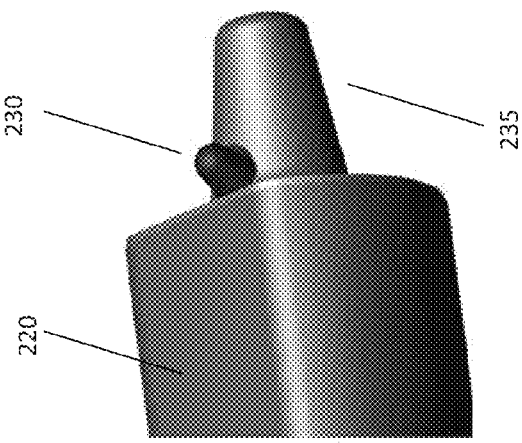

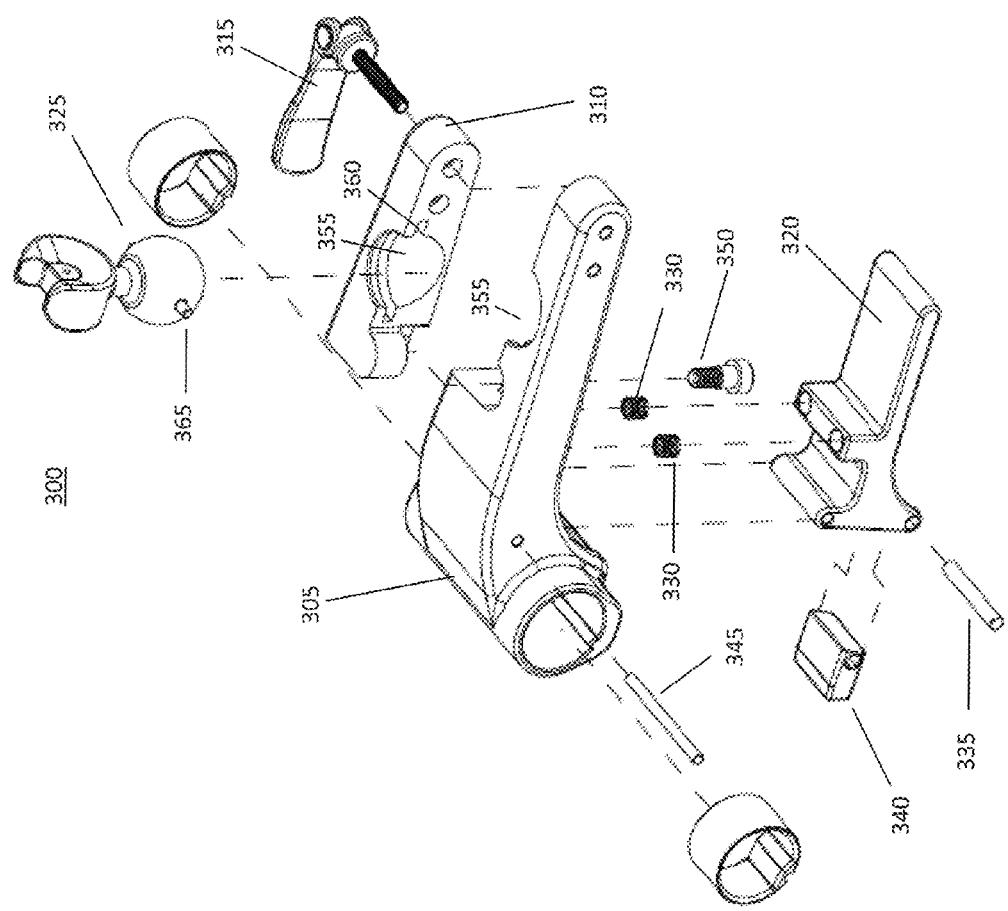

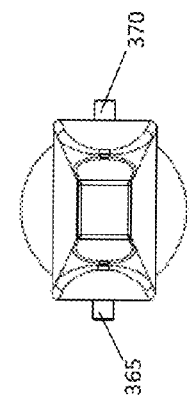
FIG. 11O
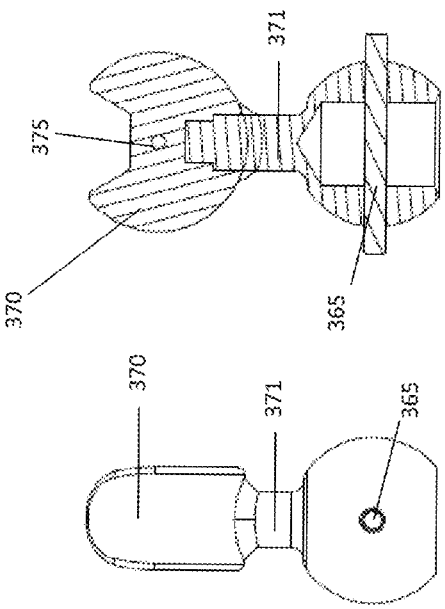
FIG. 11Q
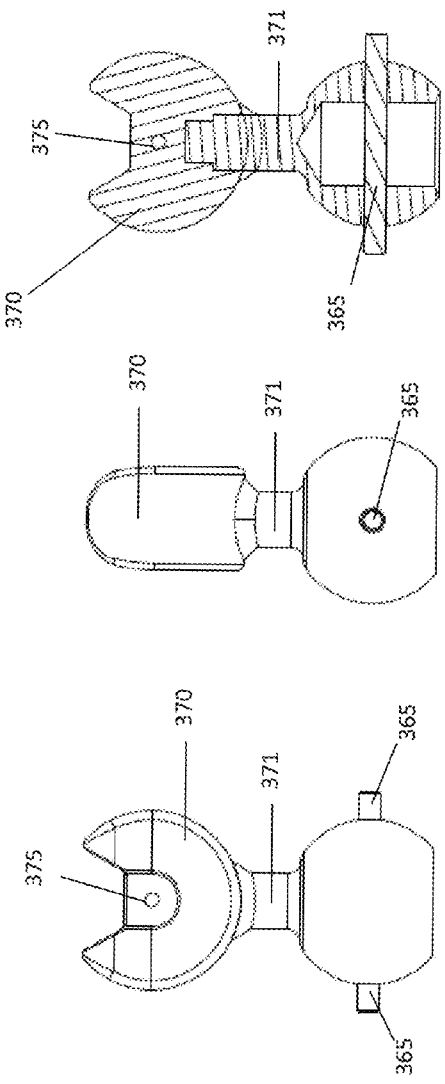
FIG. 11P
FIG. 11R

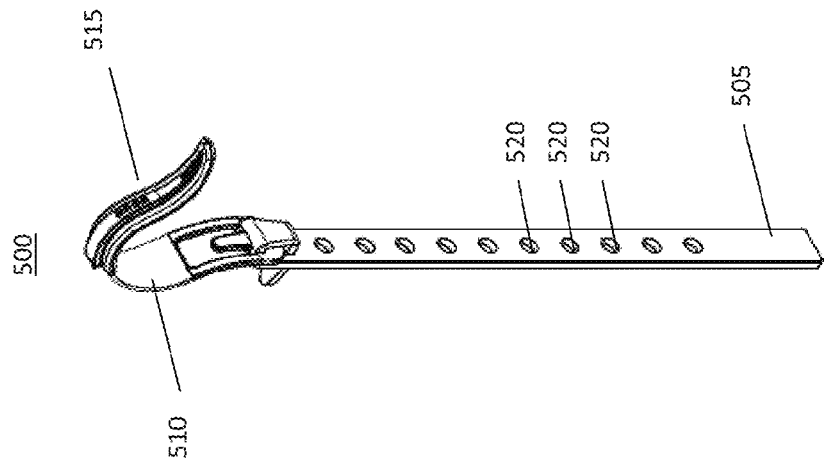

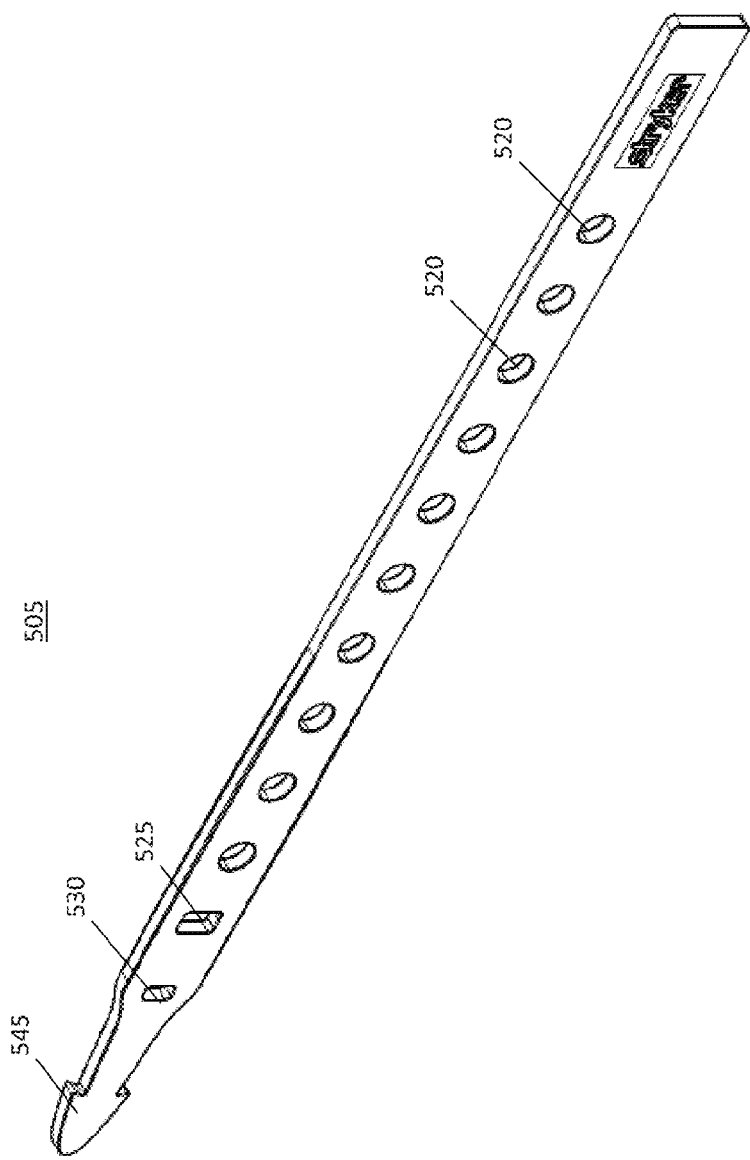

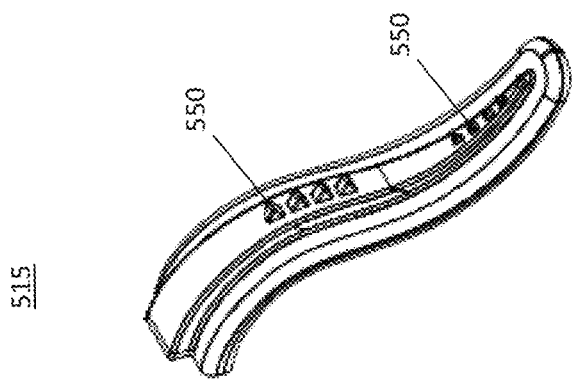

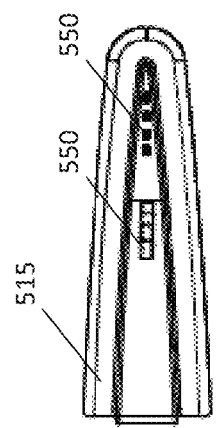
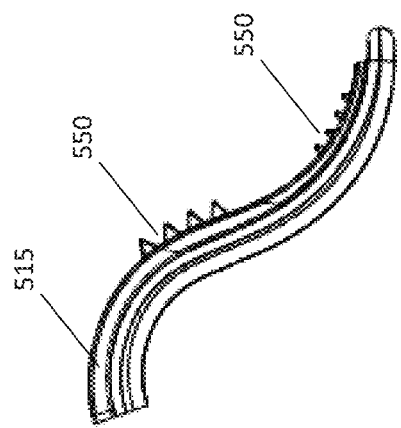
FIG. 14M
FIG. 14N
FIG. 14O

560

570

580

590

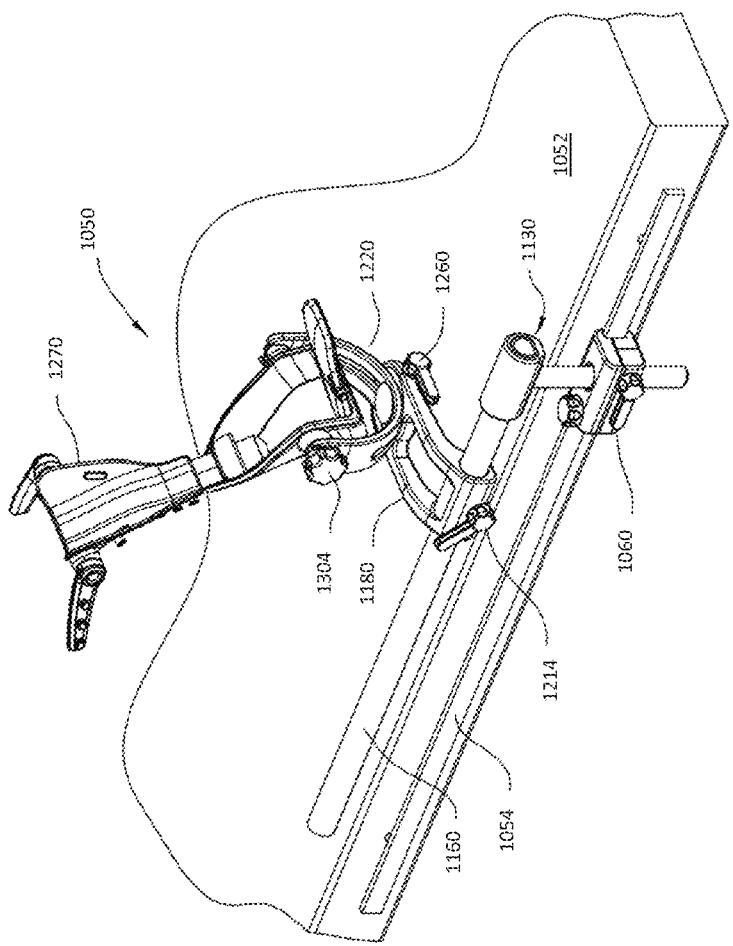

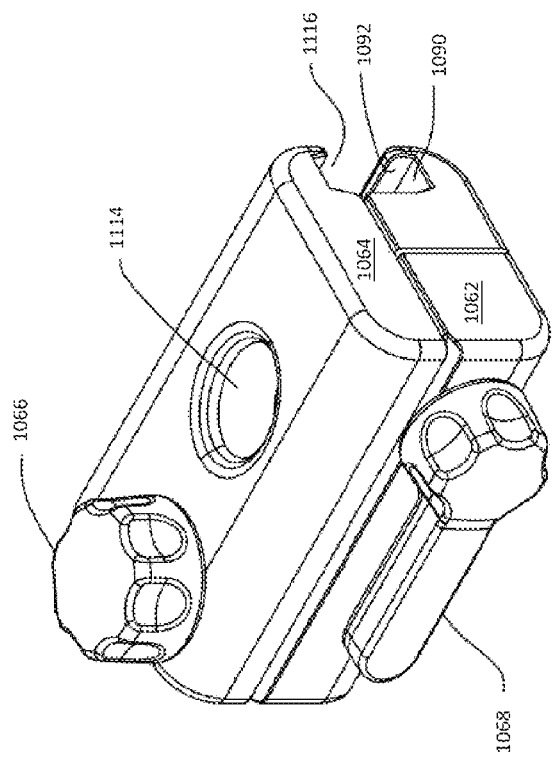

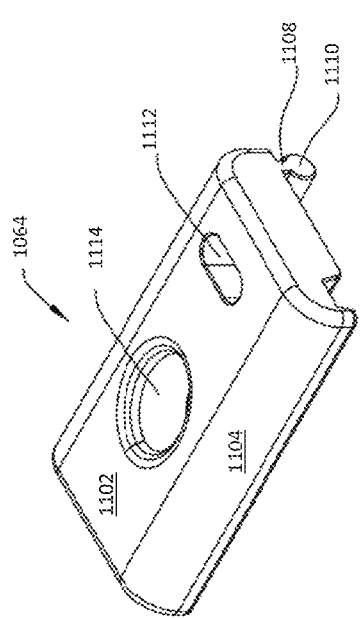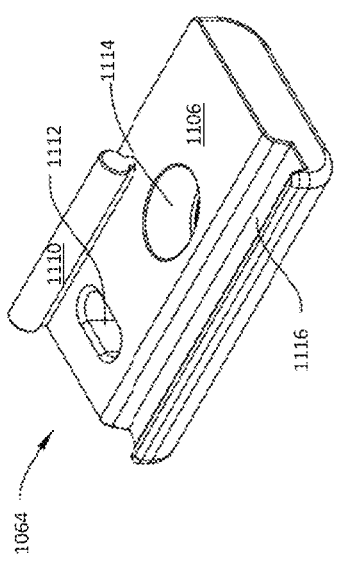

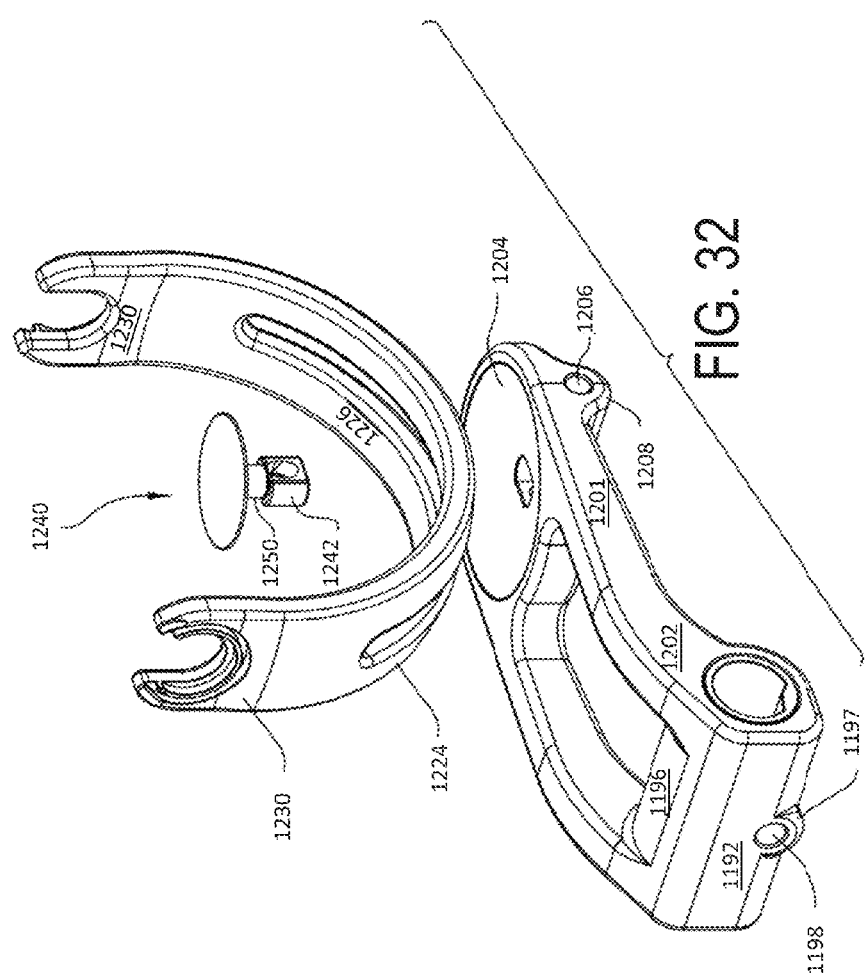

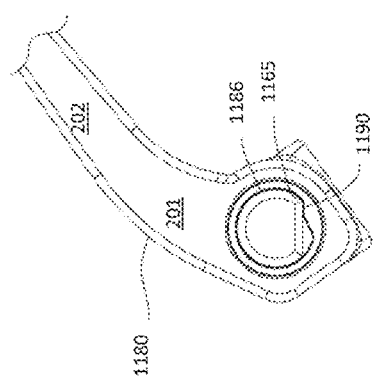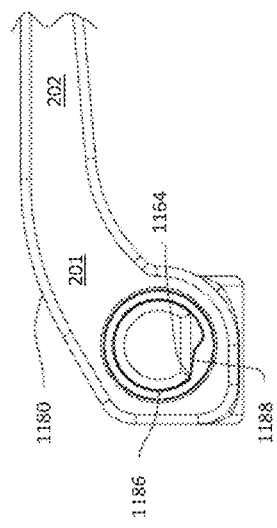

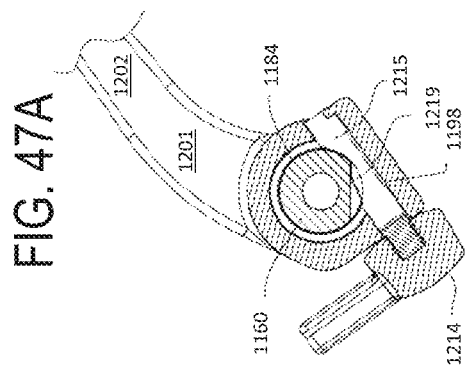
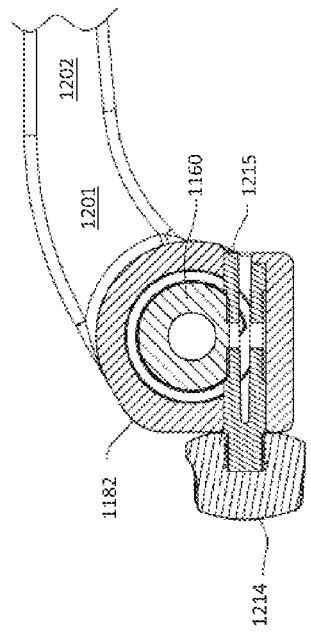
FIG. 47A
FIG. 47B

MULTI-POSITION LIMB HOLDER

CROSS-REFERENCE TO RELATED APPLICATIONS

The present application claims the benefit of the filing date of U.S. Provisional Patent Application No. 61/510,843 filed Jul. 22, 2011, the disclosure of which is hereby incorporated herein by reference in its entirety.

BACKGROUND OF THE INVENTION

This invention relates generally to a holder used to secure a body limb, such as a leg, during a medical or surgical procedure. More particularly, the holder is used to first position the limb in a selected position. The position of the limb can be adjustably set along a number of different axes. Once the position of the limb is set, the limb holder holds the limb in that position to facilitate the performance of a procedure on the patient.

When a medical or surgical procedure is performed on a limb, an arm or leg, it is desirable to restrict movement of the limb. Without holding the limb steady, it can become impossible for the practitioner to perform procedures on the limb. Further, with an increasing frequency, surgical procedures are performed with the aid of surgical navigation systems. This type of system often includes one or more trackers and a camera. In one version of this system, at least one tracker 2000, for example as shown in FIGS. 53-54, is attached to the patient. For example, the tracker 2000 is shown adapted to be used with a general instrument 2300. In order to couple the tracker 2000 to the general instrument 2300, an adapter 2302 may be connected to an adapter interface 2210 of the tracker 2000 and the general instrument 2300 is attached by a clamp screw 2304. Based on the signals emitted by the tracker, the camera and associated software determines the position of the tracker. By extension, this leads to the determination of the position of the attached patient. (Some surgical navigation systems have trackers with units that, instead of emitting energy, track energy emitted from the static source.) For many surgical navigation systems to operate, the trackers and camera must be in close proximity to each other. This means that it may be necessary to restrain the movement of the limb so that the tracker and complementary camera are able to engage in the appropriate signal exchange. Surgical navigation systems are described more fully in U.S. Pat. No. 7,725,162, the entire contents of which are hereby incorporated by reference herein.

Presently there are a number of different devices that can be used to hold the limb of the patient. These devices include some sort of shell or frame designed to receive the limb. Structural members hold the shell or frame to the operating table. At the start of the procedure, the patient's limb is placed in the shell. The shell is positioned at a location which allows the practitioner to perform the procedure. If a navigation unit is used to facilitate the procedure, the shell is further positioned to ensure that any components of the system fitted to the patient are within the appropriate range to the complementary static components of the system.

Available limb holders are able to hold the limb of the patient in a fixed position. However, there are limitations associated with some of these limb holders. Sometimes during a procedure, the practitioner may want to move a portion of the patient. For example, during some orthopedic surgical procedures on the knee, the practitioner may want to bend the knee so that the patient's leg is moved between the extended (straight) and flexed (bent) positions. Some available limb holders are designed so that, to move the limb, the actual limb holding component is temporarily disconnected from the other components of the assembly. This means that, to reposition the limb, the limb holder is first disconnected and then moved. Once the limb holder is repositioned it is reattached to the other assembly components. Having to perform all these steps makes repositioning the limb a complicated task.

Still other limb holder assemblies comprise components that only allow the attached limb to be move in between a number of defined positions. This means that the practitioner may not be able to make precise or small adjustments of limb positioned that may be desired in order to accomplish a particular medical or surgical procedure.

Also, prior to placing the patient on a surgical table, it is common practice to place a sterile drape on the table. This drape functions as a sterile barrier between the table and the patient. Some available limb holders are designed to be attached directly to the tables with which the holders are used. At the location where this type of limb holder is attached it is difficult, if not impossible to, place the drape around and/or under the limb holder so as to provide the desired sterile barrier.

BRIEF SUMMARY OF THE INVENTION

In one embodiment of the invention, a limb positioning device includes a frame generally shaped to receive the limb, the position of which is to be fixed. Plural structural units connect the frame to the surgical table on which the patient is positioned. Each structural unit moves in at least one degree of freedom relative to the structural member to which the structural unit is connected. Generally, at least one structural unit moves linearly relative to the structural units to which they are connected. At least one and, more often two, of the structural units, rotates along at least one axis relative to the structural units to which they are connected.

In another aspect, the position of the limb holding frame can be adjusted while the frame remains attached to the other components of this limb holder. In some embodiments of the invention, it is possible to pivot the frame around at least one axis while the frame remains attached to the other components of the limb holder. In another embodiment of the invention, it is possible to pivot the limb-holding frame about either one axis or a plural number of axes while the frame remains attached to the other components forming the limb holder.

In another embodiment of the invention, the sub-assemblies that hold the components to each other do not have step adjustments. The sub-assemblies that hold the components together for relative vertical or horizontal displacement allow the component positions to be adjusted down to infinitesimally small distances. The sub-assemblies that hold the components together for relatively angular orientations allow the component position to be adjusted down to infinitesimally small angles. These features of the limb holder make it possible for the position of the limb-holding frame to be marginally reset.

The patient's limb is held in position by placing the limb in the frame. The frame and other structural units are then positioned and oriented relative to each other to place the limb in the position desired for the particular medical/surgical procedure. Straps or pads are secured to the frame so as to extend over the limb. The straps/pads hold the limb to the frame in order to allow the desired medical/surgical procedure to be performed.

In an embodiment of the invention, at least one of the structural units is able to move in at least two degrees of freedom relative to the immediate structural member to which the unit is connected.

In an embodiment of the invention, the frame is a boot. This particularly frame is shaped like the bottom of the foot and the adjacent lower leg. Since the limb holder can be moved linearly, the frame can be moved along the operating table while holding the patient's foot and lower leg. Such movement is used to, during the procedure, flex the leg.

In an embodiment of the invention, the frame is shaped to hold the arm. This frame may be in the shape of an elongated shell that, in cross section appears to be semi-circular.

It is still a further feature of an embodiment of the invention that the holder can be mounted over the surgical drape disposed between the operating table and the patient. The presence of this limb holder therefore does not disrupt the sterile barrier provided by the drape.

In yet another embodiment of the invention, the limb positioning device includes a clamp attachable to a patient support, a first support member configured to connect to the clamp, a second support member slidingly coupled to the first support member, and a limb holder polyaxially coupled to the second support member. The limb positioning device can include support wings and devices to attach to the support wings, such as navigation and tracking systems or retractors. When the support wings are fixed to the limb holder, the support wings and connected devices are capable of movement with the limb holder.

In an embodiment of the invention, the limb positioning device is supported in part by a post connected to a clamp that is fastened to a table, and an elongate bar attached to the post. The elongate bar provides a track along which the limb holder slides. The limb holder can be attached to a support with a ball and socket assembly that allows one, two or more degrees of freedom of motion with respect to the support. A number of locking devices can be provided to lock the limb holder from movement relative to its support, and to lock the support from movement relative to the elongate bar. These locks can be configured such that a user must provide some amount of force to unlock a lock. In other words, these locks can be biased to a lock position. The elongate bar can comprise a first portion that attaches to the post and a second portion that attaches to the first portion. The elongate bar can include a coupling mechanism where one portion of the elongate bar has a protrusion that fits into a slot in the other portion of the elongate bar. The limb holder may also be infinitesimally adjustable in six degrees of freedom of motion with respect to the clamp.

In a further embodiment, a limb positioning assembly can include a clamp and a support post. The support post is connectable to the clamp and infinitesimally adjustable in at least one degree of movement with respect to the clamp. A rail is connectable to the support post, and a support assembly is connectable to the rail. The support assembly is infinitesimally adjustable with respect to the rail in at least one degree of movement. A limb holder is detachably connectable to the support assembly and is infinitesimally adjustable with respect to the support assembly in at least three degrees of movement.

According to a further embodiment of the invention, a method of positioning a limb during a procedure includes attaching a clamp over a sterile drape and onto a patient support. A support post is positioned in the clamp at a specific height. An elongate bar is connected to the support post, and a support assembly is connected to the elongate bar. The support assembly is slid along the elongate bar to a specific position and locked in that specific position. A limb holder is connected to a rotation mechanism of the support assembly and is rotated to a specific rotational position and locked in the specific rotational position.

The limb holder can also be detached from the support assembly without adjusting any of the specific height position of the support post, the specific position of the support assembly along the elongate bar, and the specific rotational position of the rotation mechanism. Further, after the limb holder is detached from the support assembly, at least one of the specific height position of the support post, the specific position of the support assembly along the elongate bar, and the specific rotational position of the rotation mechanism can be adjusted. After the adjustment, the limb holder can be reattached. Additionally, a patient's limb can be inserted into the limb holder and the support assembly can slide along the elongate bar to cause the patient's limb to flex or elongate.

BRIEF DESCRIPTION OF THE DRAWINGS

The invention is pointed out with particularity in the claims. The above and further features and benefits of this invention may be better understood from the following Detailed Description taken in conjunction with the drawings.

FIGS. 5A-B are perspective views of the bottom jaw of the clamp assembly shown in FIG. 2.

FIGS. 10A-F show multiple views of a support bar included with the limb holder shown in FIG. 1.

FIGS. 10G-H show the locking and unlocking mechanism of the support bar shown in FIGS. 10A-F.

FIG. 11A shows an exploded view of a sled included with the limb holder shown in FIG. 1.

FIGS. 11N-R show multiple views of a ball assembly of the sled shown in FIG. 11A.

FIG. 14A shows a perspective view of a retractor assembly according to one embodiment of the invention;

FIG. 14G shows a perspective view of the strap of the retractor assembly of FIG. 14A.

FIGS. 14L-O show multiple views of a retractor cover of the retractor assembly shown in FIG. 14A.

FIG. 16 is a perspective view of one particular embodiment of a limb holder, specifically a leg holder, according to another embodiment of the invention.

FIG. 17 is a perspective of the limb holder clamp shown in FIG. 16.

FIG. 20 is a perspective view of the upper jaw of the clamp shown in FIG. 17.

FIG. 21 is an alternative perspective view of the upper jaw of the clamp shown in FIG. 17.

FIG. 32 is an exploded view of the yoke shown in FIG. 29 adjustably mounted to the sled shown in FIG. 26.

FIG. 46A is a side view depicting the orientation of the sled of FIG. 26 relative to a complementary bar when the sled is able to move over the bar.

FIG. 46B is a side view depicting the orientation of the sled of FIG. 26 when the sled is in a locked state over a bar.

FIG. 47A is a partial cross sectional view depicting the relative states of the sled of FIG. 26 and a sled lock knob when the knob is in an unlocked state.

FIG. 47B is a partial cross sectional view depicting the relative states of the sled of FIG. 26 and a sled lock knob when the knob is in a locked state.

DETAILED DESCRIPTION

Figure 1:
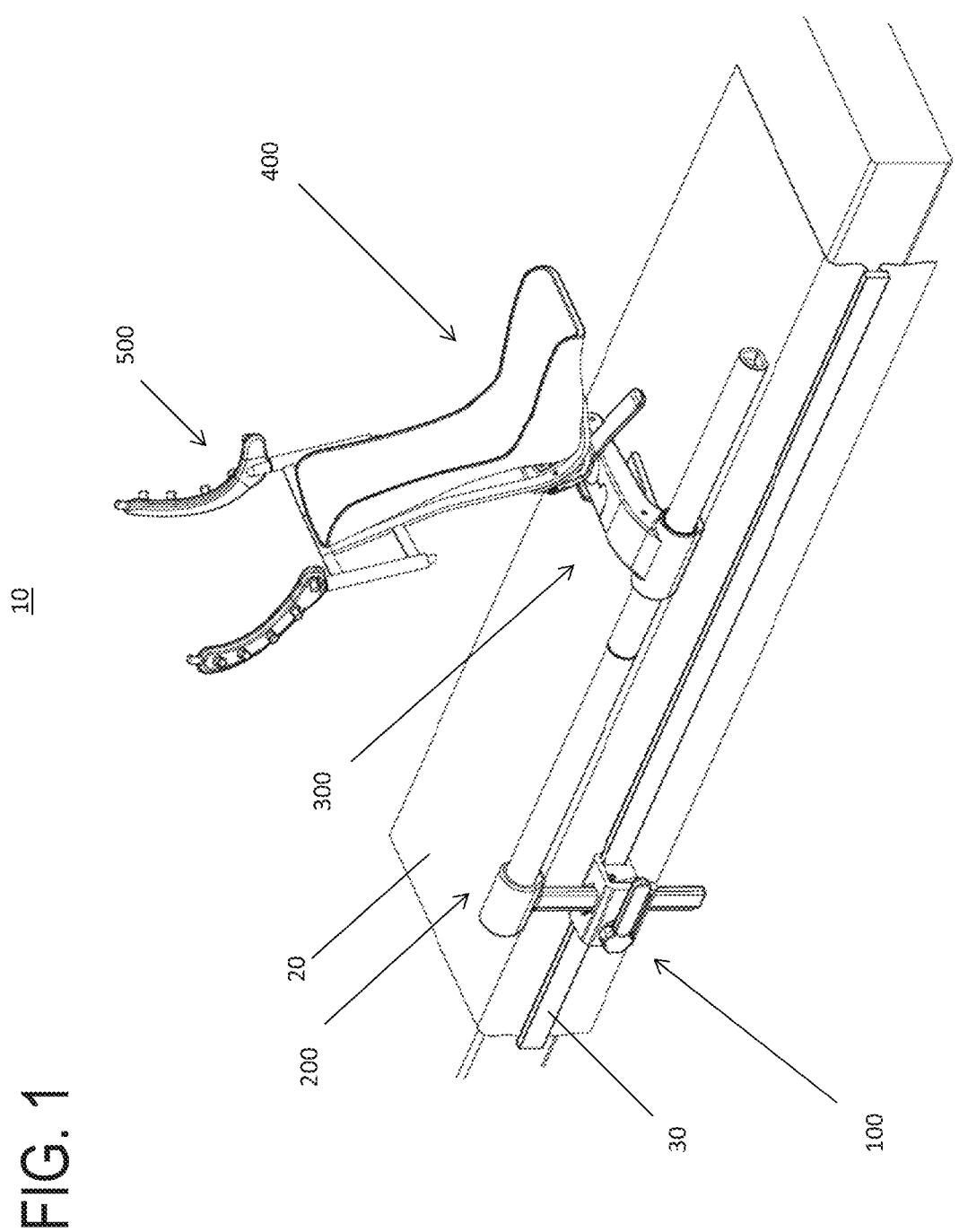
FIG. 1 is a perspective view of a limb holder according to one aspect of the invention.

FIG. 1 illustrates one embodiment of a limb holder 10. Limb holder 10 generally includes a clamp assembly 100, a pylon and rail assembly 200, a sled assembly 300, a limb holding assembly 400, and a retractor assembly 500.

The particular limb holder 10 shown in FIG. 1 is shaped to hold the foot and lower leg in a fixed position to a table 20, which holds the remainder of the patient. Other embodiments of limb holder 10 may be shaped to hold other body parts, such as an arm. Table 20 is understood to be a table, a bed or any support structure upon which a patient may be disposed.

Generally, limb holder 10 is mounted to a DIN rail 30, a rectangular bar that is often fixedly mounted to the side of a surgical table 20, by way of a clamp assembly 100.

Figure 2:
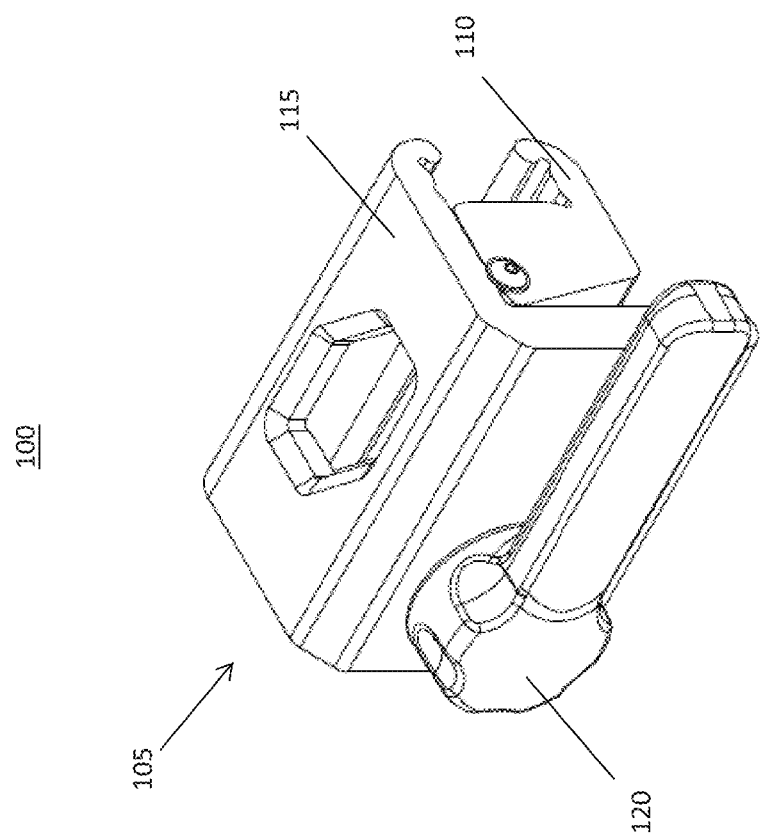
FIG. 2 is a perspective view of a clamp assembly included with the limb holder shown in FIG. 1.
Figure 3B:
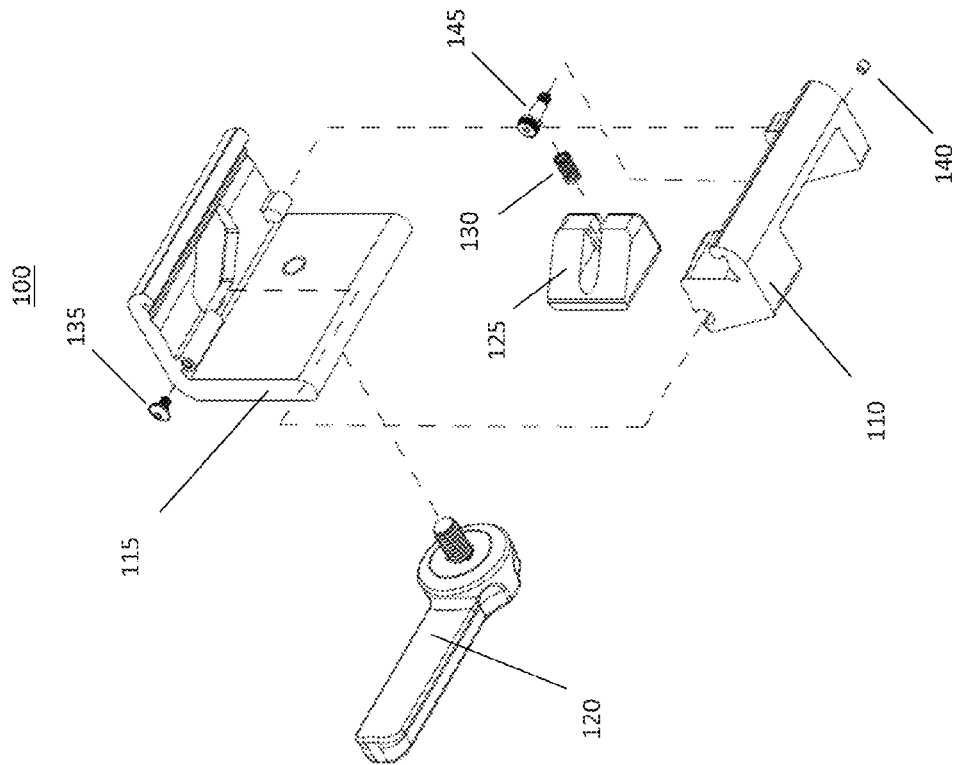
FIGS. 3A-3B are exploded views of the clamp assembly shown in FIG. 2.
Figure 3A:
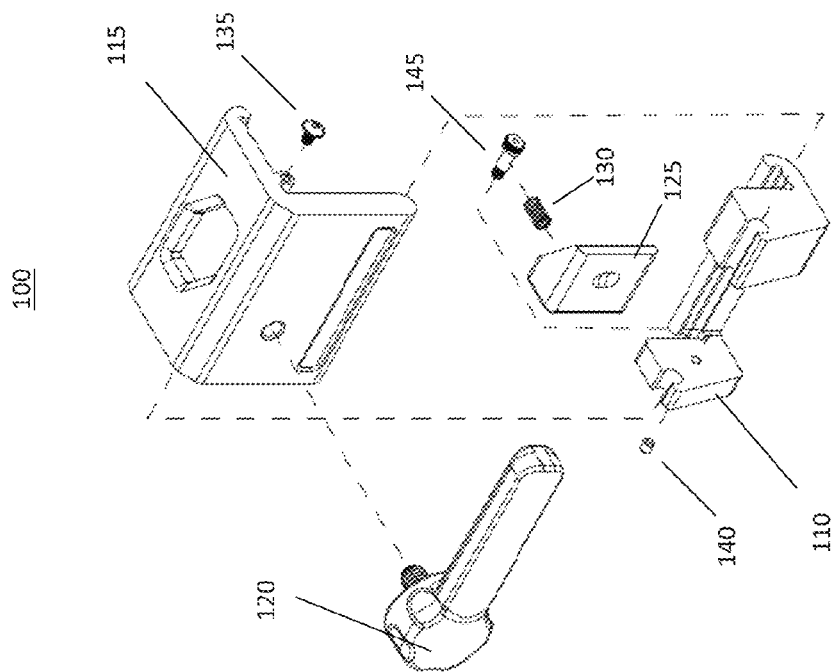

As seen in FIGS. 2 and 3A-3B, clamp assembly 100 generally includes lower jaw 110, upper jaw 115, handle 120, block 125, spring 130, upper jaw screw 135, lower jaw screw 140, and spring pin 145.

Figure 4B:
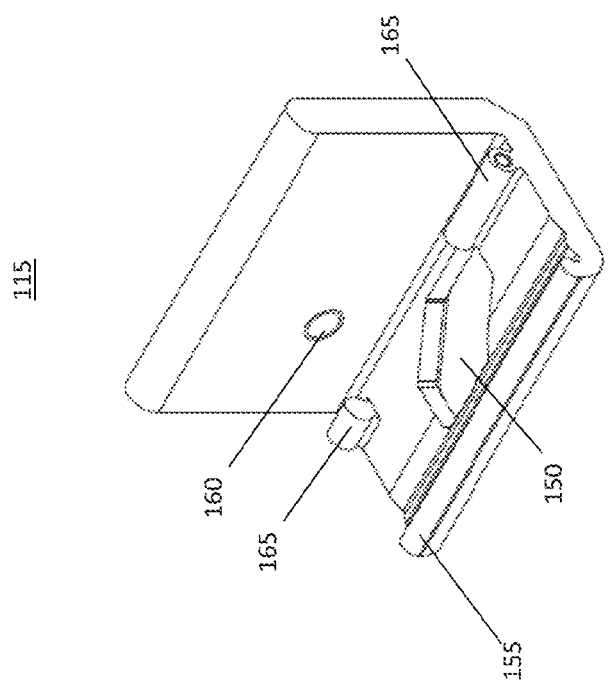
FIGS. 4A-B are perspective views of the top jaw of the clamp assembly shown in FIG. 2.
Figure 4A:
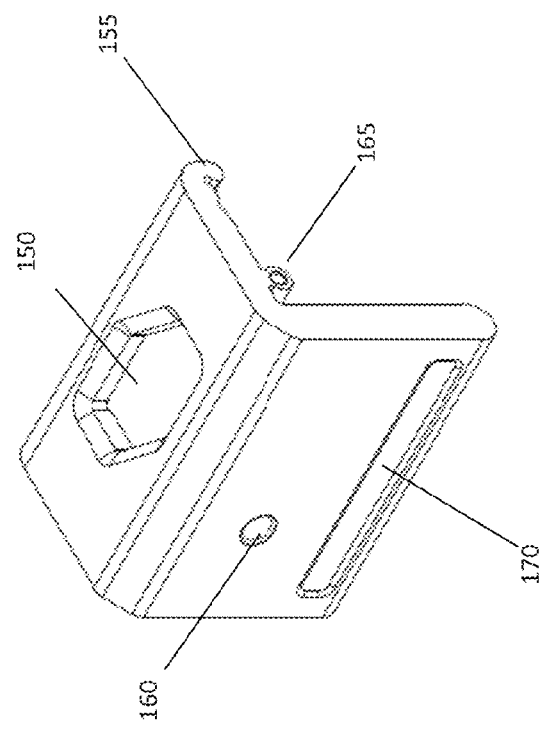

Upper jaw 115, as seen in FIGS. 4A-B, is generally J-shaped. The top surface of upper jaw 115 includes an aperture 150 for receiving a post, such as mounting pylon 205. The aperture 150 can be any shape, such as a circle, oval or square. In one embodiment, aperture 150 is generally hexagon shaped and is capable of preventing rotation of a post received therein. Upper jaw 115 further includes an upper jaw lip 155. Upper jaw lip 155 enhances frictional engagement with DIN rail 30. The sidewall of upper jaw 115 includes handle aperture 160, which may include threading, to receive handle 120. The underside of the top surface of upper jaw 115 further includes one or more mating features 165. In the embodiment shown, two mating features 165 are each cylindrical protrusions. Other mating features, such as hinge or other features that provide a pivotal connection with lower jaw 110, are within the scope of the invention. One or more of the mating features 165 may include apertures, such as threaded apertures. In the embodiment shown, one of the mating features 165 includes a threaded aperture to accept upper jaw screw 135. The sidewall of upper jaw 115 can optionally include gripping surface 170. For example, a user may hold the lower jaw 110 with fingers of one hand, grip the gripping surface 170 of the upper jaw 115 with the thumb, and open and close the clamp 105 with only one hand. The operation of the clamp 105 in relation to the other components is described more fully below.

Lower jaw 110, as seen in FIGS. 5A-B, generally includes two J-shaped pieces 176 connected by an extension member 177. The space between the two J-shaped pieces 176 of lower jaw 110 has sufficient clearance to accept a post, such as mounting pylon 205, after the post is inserted through aperture 150 of the upper jaw 115. The extension member 177 of the lower jaw 110 further includes a lower jaw lip 175. Lower jaw lip 175 enhances frictional engagement with DIN rail 30. A wall of lower jaw 110 includes a spring pin aperture 180, which may include threading, to accept spring pin 145. As best seen in FIGS. 3A-B, spring pin 145, once screwed into spring pin aperture 180, provides a surface against which spring 130 abuts. The other side of spring 130 abuts block 125, described in more detail below. The top surface of lower jaw 110 further includes one or more mating features 185. The mating features 185 of the lower jaw 110 are configured to mate with the mating features 165 of the upper jaw 115. In the embodiment shown, two mating features 185 are each cylindrical indentations that slidingly accept the cylindrical protrusion mating features 165 of the upper jaw 115.

Figure 6B:
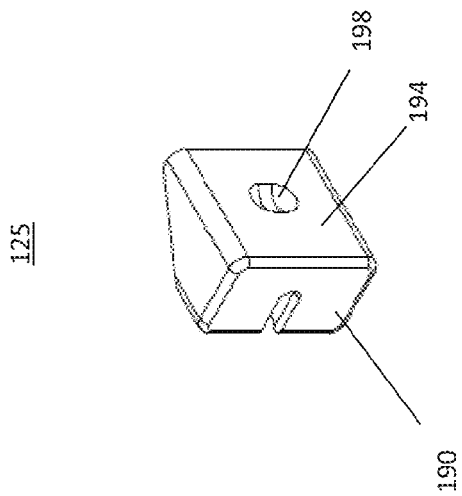
FIGS. 6A-B are perspective views of the block of the clamp assembly shown in FIG. 2.
Figure 6A:
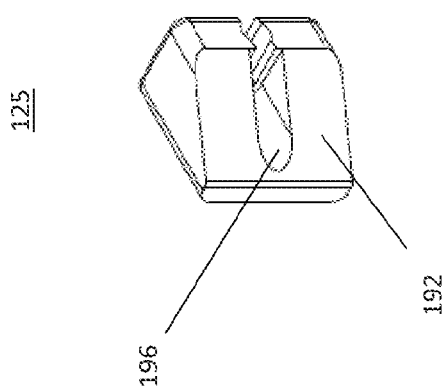
Figure 7:
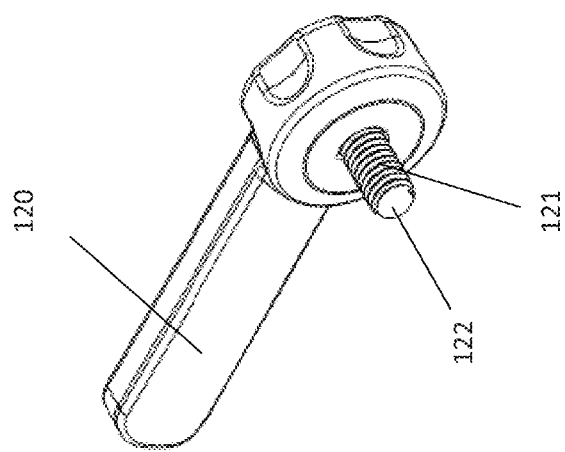
FIG. 7 is a perspective view of the handle of the clamp assembly shown in FIG. 2.

In one embodiment, block 125, as seen in FIGS. 6A-6B, is substantially wedge shaped with a flat side 190, a diagonal face 192, a flat back 194, a groove 196 extending from the flat side 190 through the diagonal face 192, and a half-spherical groove 198. The groove 196 is configured to accept the spring pin 145 and spring 130. One side of spring 130 contacts the groove 196 in the block 125. The other side of spring 130 contacts the spring pin 145. When in place in the clamp 105, the flat side 190 of block 125 abuts one of the J-shaped pieces 176 of lower jaw 110 and the half-spherical groove 198 generally aligns with the handle aperture 160 of the upper jaw 115. Referring to FIG. 7, the handle 120 includes a threaded screw 121 on one end. The end of the threaded screw 121 includes a half-spherical portion 122 adapted to mate with half-spherical aperture 198.

To assemble the clamp 105, the cylindrical protrusion mating features 165 of the upper jaw 115 are slid into the corresponding mating features 185 of the lower jaw 110. Block 125 is then situated between upper jaw 115 and lower jaw 110. The spring 130 is inserted such that it abuts the block groove 196 on one side. The spring pin 145 is threaded into the corresponding spring pin aperture 180 in lower jaw 110. Upper jaw screw 135 is threaded into the aperture in the upper jaw mating feature 165 to lock the mating features 165, 185 in place. The lower jaw screw 140 is threaded onto the spring pin 145 to further stabilize the spring pin 145 within the lower jaw 110. The lower jaw screw 140 can alternatively be a plug that functions to plug the aperture in the outside of the lower jaw 110 created by the spring pin aperture 180.

Figure 8:
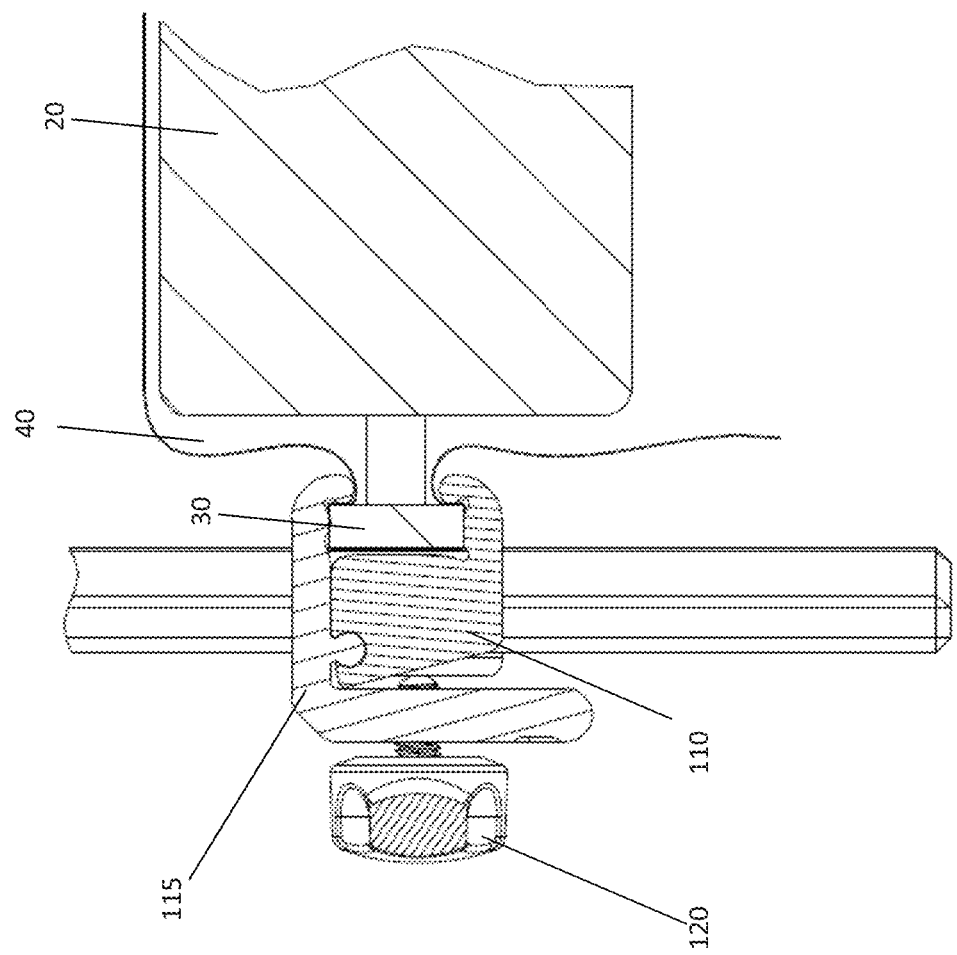
FIG. 8 is a side and partial cross sectional view depicting the clamp assembly of FIG. 2 coupled to a DIN rail over a surgical drape.
Figure 9A:
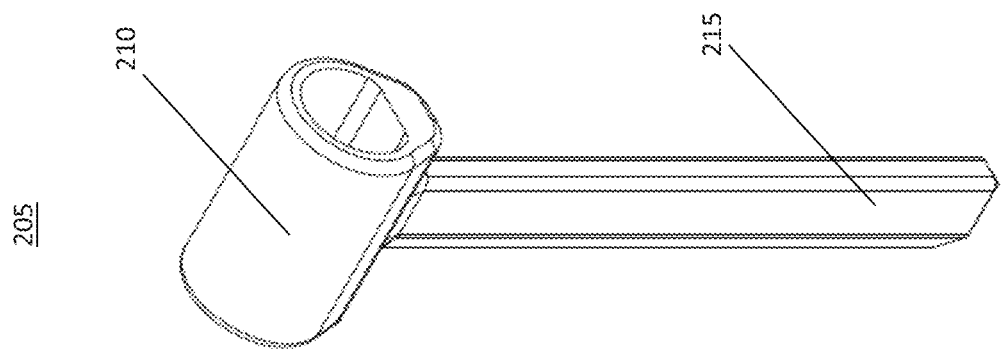
FIGS. 9A-D show multiple views of a mounting pylon included with the limb holder shown in FIG. 1.
Figure 9C:
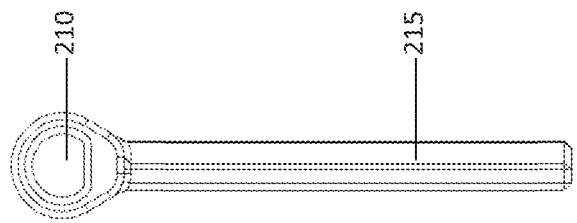
Figure 9B:
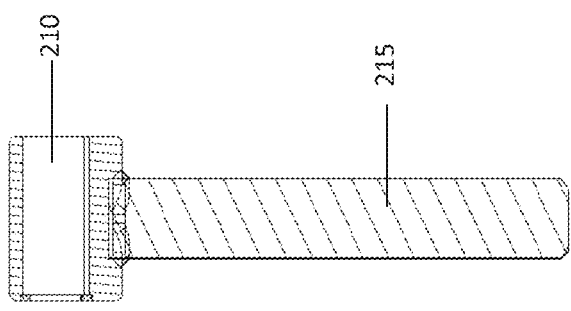
Figure 9D:
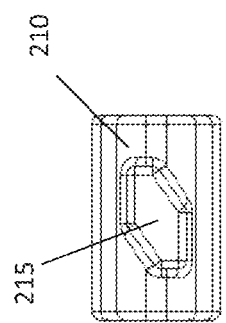

The handle 120 is threaded through handle aperture 160 in upper jaw 115 until the half-spherical portion 122 of the handle mates with the half-spherical groove 198 of block 125. At this point, before the handle 120 is fully threaded through the upper jaw 115 and block 125, a user can open the clamp 105 using a single hand. As the clamp 105 opens, block 125 is pushed generally in the direction of upper and lower jaw lips 155, 175, causing the spring 130 to compress between the spring pin 145 and block 125. This force urges the block 125 back in the general direction of handle 120, such that if the user loosens his grip on the clamp 105, the clamp 105 will tend to close as the block 125 presses backwards against upper jaw 115. This allows a user to manipulate clamp 105 with one hand from a closed configuration to an open configuration, place the clamp 105 in the open position over DIN rail 30, and release his grip such that clamp 105 clamps down over DIN rail 30. As seen in FIG. 8, once clamped over the DIN rail 30, the upper jaw lip 155 and lower jaw lip 175 abut the side of the DIN rail 30 facing table 20, increasing the stability of clamp 105 on DIN rail 30. Further as shown in FIG. 8, the clamp 105 can be closed over a sterile drape 40 that is draped over the table 20 and over the DIN rail 30.

Once clamped onto the DIN rail 30, a device, such as a mounting pylon 205 shown in FIGS. 9A-D, can be inserted into the aperture 150 of the upper jaw 115 and through the lower jaw 110. The mounting pylon 205 generally includes a rail-receiving portion 210 and a shaft 215. Rail-receiving portion 210 of mounting pylon 205 can be shaped to receive a rail to support a device. In the embodiment shown, rail-receiving portion 210 includes a generally hollow cylinder with a flattened portion configured to accept a rail and prevent rotation of the rail. The shaft 215 is shaped to correspond to the aperture 150 of the upper jaw 115. In the embodiment shown, the shaft 215 is generally a hexagon shape, but this is largely a matter of design choice.

Once the mounting pylon 205 is at the desired position within the clamp 105, the user can continue to rotate the handle 120. As rotation continues, the block 125 is pressed into the shaft 215 of mounting pylon 205 while the upper jaw 115 is pulled toward the handle 120. The movement of the upper jaw 115 backwards causes the upper jaw 115 to rotate relative to the lower jaw 110 about a pivot point at the mating features 165, 185. This rotation closes the clamp 105 on the DIN rail 30 into a secure, locked position. Similarly, the pressing action of the block 125 against the mounting pylon 205 locks the mounting pylon 205 at the desired vertical height and position.

Figure 10D:
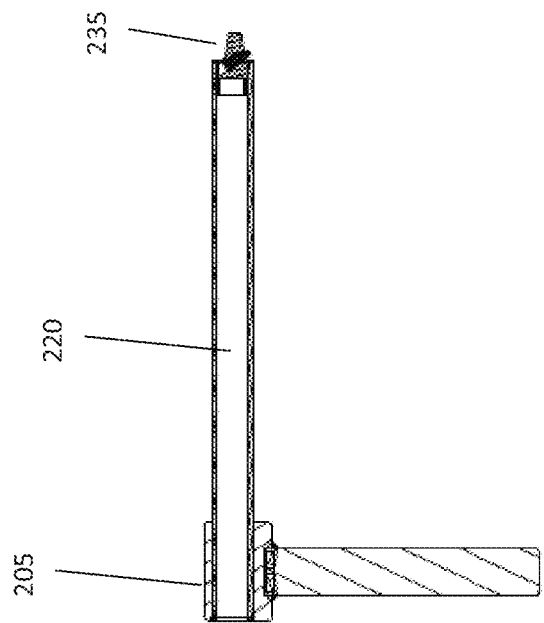
Figure 10C:
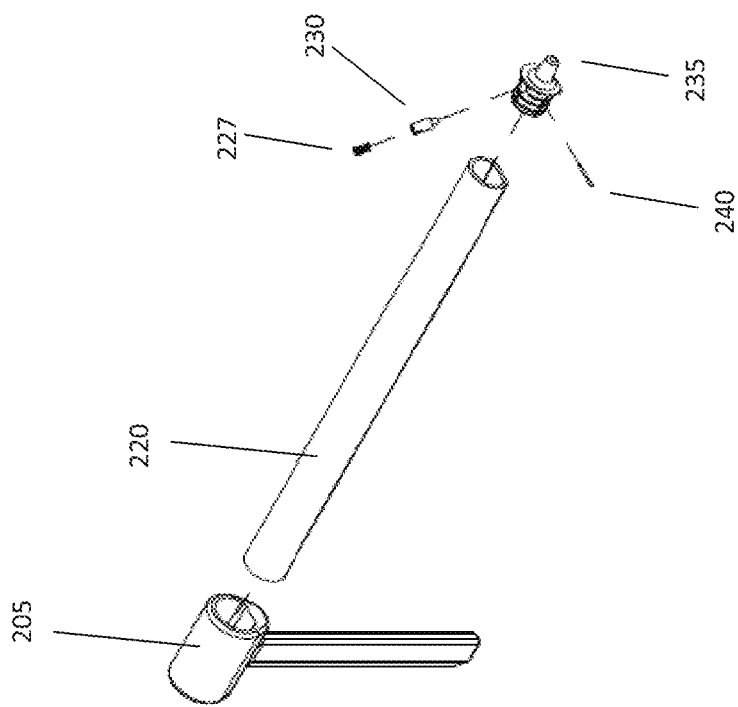

Once the pylon is in place, a rail assembly, as shown in FIGS. 10A-H can be placed into position. In the embodiment shown, the pylon and rail assembly 200 generally includes a mounting pylon 205, described above, a first rail 220 and a second rail 225. As best seen in FIGS. 10C-D, first rail 220 is inserted into rail-receiving portion 210 of the mounting pylon 205. Alternatively, first rail 220 can be fixed within rail-receiving portion 210, for example by epoxy. In the embodiment shown, the first rail 220 is generally cylindrical with a flattened end such that the first rail 220 cannot rotate when inserted within the mounting pylon 205. The end of the first rail 220 remote from the mounting pylon 205 includes a spring 227 and plunger 230 assembly and a tapered orientation feature 235. A cross pin 240 may be included to hold the spring 227 and plunger 230 in place. The second rail 225, as best seen in FIGS. 10E-F, includes a tapered reception portion 245 with a release button 250 on one end, and an end cap 260 on the other end. A cross pin 255 may be included to connect the release button 250 and allow pivoting of the release button about the axis of the cross pin 255. Additionally, an end cap 260 may be included to close the end of the second rail 225. The end cap 260 may additionally be designed to keep the sled assembly 300, described below, from sliding off the end of the second rail 225.

After the first rail 220 is secured in the mounting pylon 205, as best seen in FIGS. 10G-H, the second rail 225 can be snapped onto the first rail 220 if extra length is desired. The second rail 225 has a tapered reception portion 245 that is configured to mate with the tapered orientation feature 235 of the first rail 220. As the tapered orientation feature 235 enters the tapered reception portion 245, the plunger 230 is pushed inward and the spring 227 is compressed. The tapered reception portion 245 has a recess 255 that accepts plunger 230. As a user inserts the second rail 225 onto the first rail 220, he can rotate the second rail 225 until the plunger 230 is properly oriented with the recess 255. Once aligned, the force from the spring 227 will snap the plunger 230 into the recess and lock the first rail 220 with respect to the second rail 225. Because there is only a single recess, the first and second rails 220, 225 can only mate in a single orientation. If the user wants to decouple the first rail 220 from the second rail 225, he can depress the release button 250 on the second rail 225, causing the plunger 230 to move inward and the spring 227 to compress. This unlocks the first rail 220 from the second rail 225, at which point the user can remove the second rail 225. Once the clamp assembly 100 and the pylon and rail assembly 200 are set in place, the sled assembly 300 can be put into position on the pylon and rail assembly 200. In one embodiment, the mounting pylon 205 is formed of a metal such as aluminum, while the first and second rails 220, 225 are formed from carbon fiber or a metal such as stainless steel. The first and second rails 220, 225 may be solid or hollow.

Figure 11B:
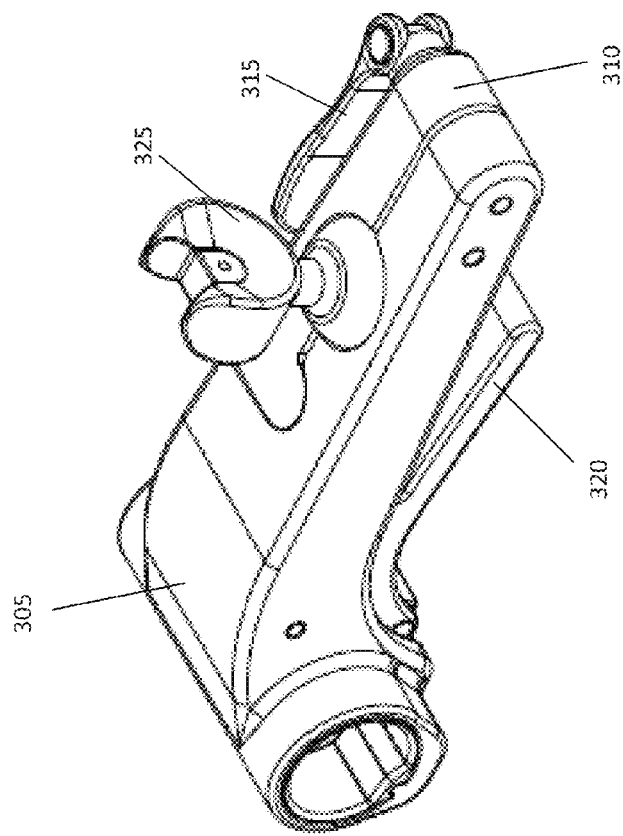
FIG. 11B shows a perspective view of the sled shown in FIG. 11A in a locked state.
Figure 11C:
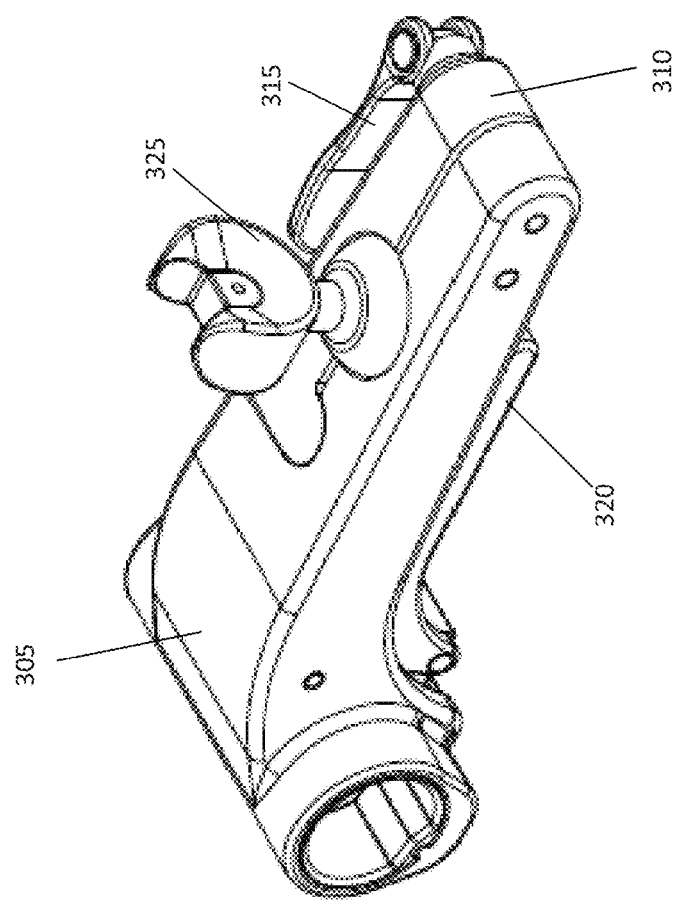
FIG. 11C shows a perspective view of the sled shown in FIG. 11A in an unlocked state.
Figure 11D:
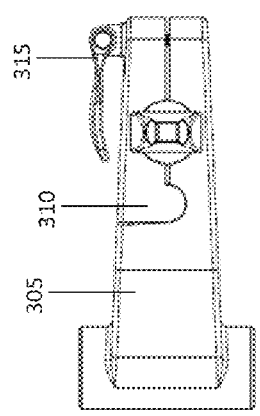
FIGS. 11D-H show multiple views of the sled shown in FIG. 11B in a locked state.
Figure 11E:
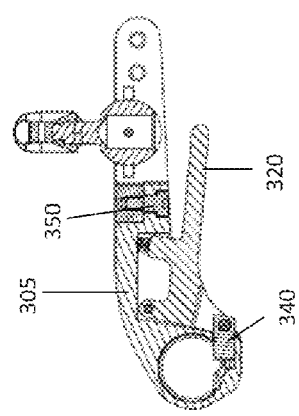
Figure 11F:
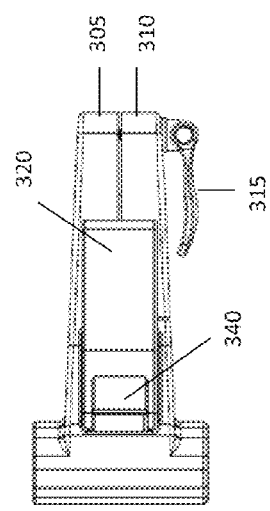
Figure 11H:
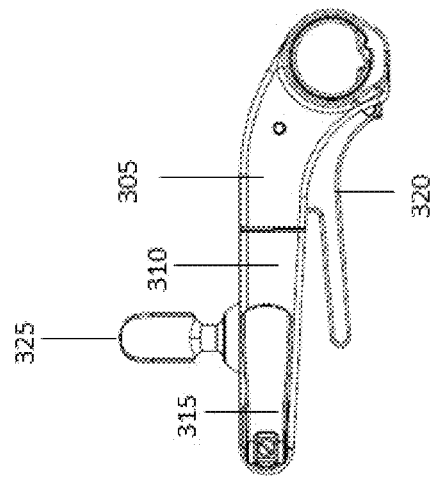
Figure 11G:
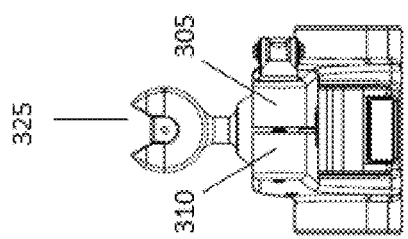
Figure 11I:
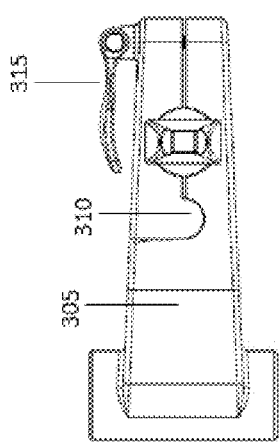
FIGS. 11I-M show multiple views of the sled shown in FIG. 11C in an unlocked state.
Figure 11J:
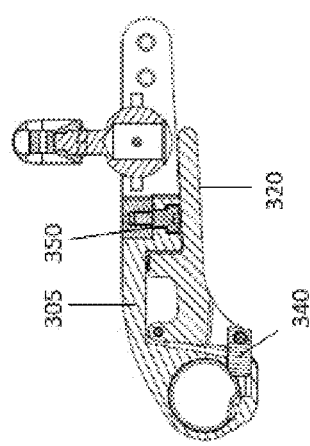
Figure 11K:
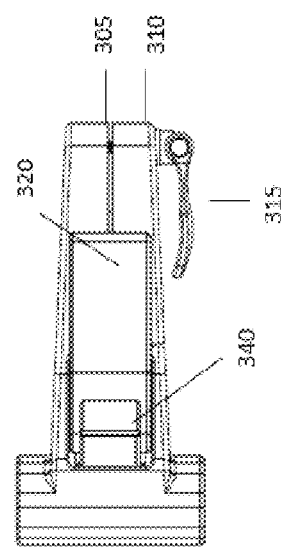
Figure 11M:
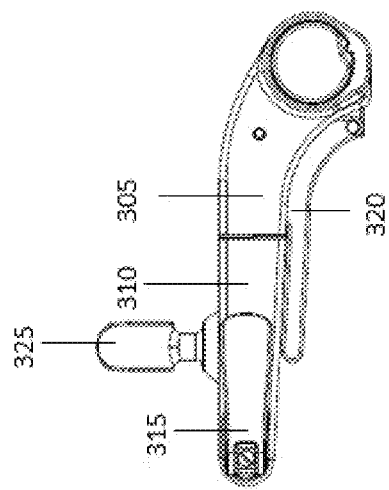
Figure 11L:
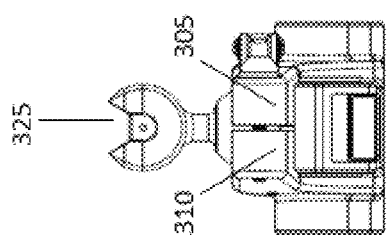
Figure 11N:
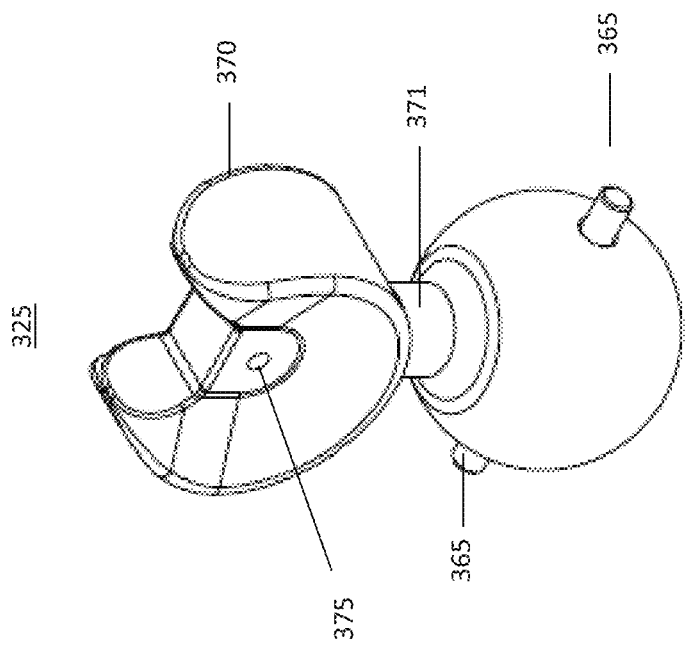
Figure 12A:
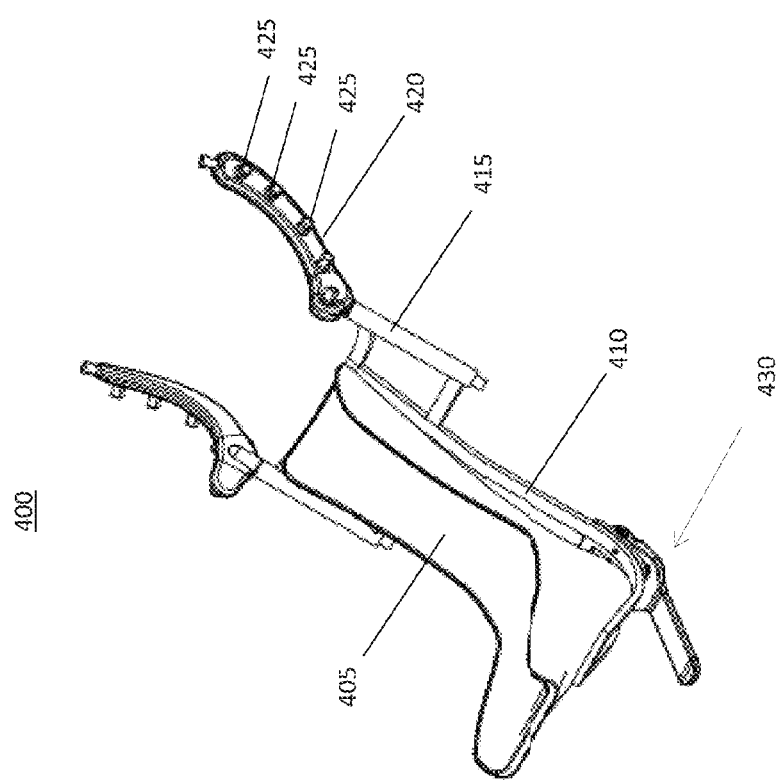
FIG. 12A shows a perspective view of the limb holder assembly shown in FIG. 1.
Figure 12B:
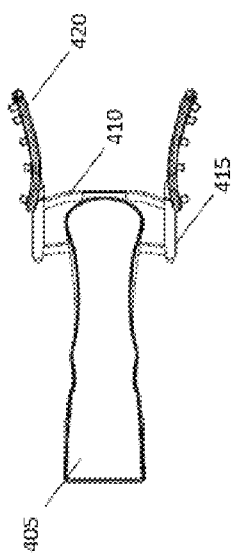
FIGS. 12B-F show multiple views of the limb holder assembly shown in FIG. 12A.
Figure 12C:
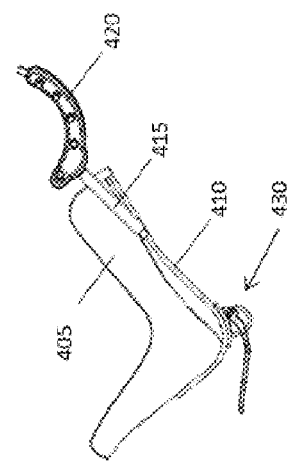
Figure 12D:
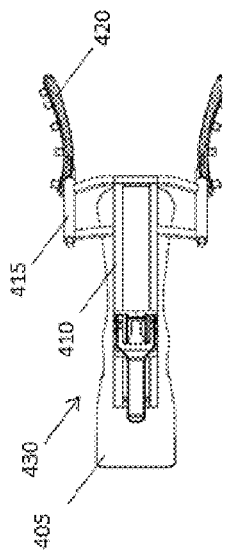
Figure 12F:
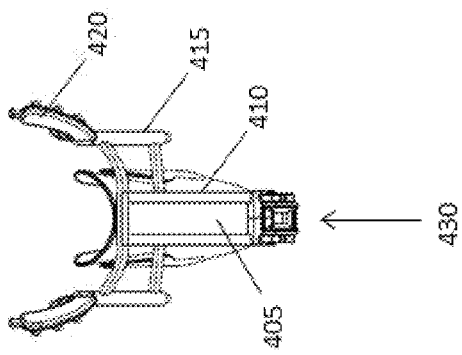
Figure 12E:
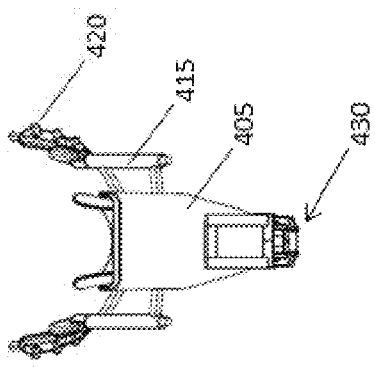

In one embodiment, sled assembly 300, as shown in FIGS. 11A-N, generally includes sled base 305, ball lock 310, locking handle 315, sled base lock 320, and ball assembly 325. Generally, the sled assembly 300 acts to support the limb holding assembly 400 and to provide sliding movement along the pylon and rail assembly 200.

As best seen in FIG. 11A, the sled base 305 includes apertures with a shape that corresponds to the first rail 220 and/or second rail 225. The corresponding shape allows sled assembly 300 to slide along the first rail 220 and/or second rail 225 without the ability to rotate about the first and second rails 220, 225.

Sled base lock 320 is attached to sled base 305 by virtue of a pin 345 that is inserted through apertures in the sled base 305 and further through apertures in the sled base lock 320. Pin 345 allows sled base lock 320 to rotate with respect to sled base 305. A pair of springs 330 abuts the sled base lock 320 on one side and the sled base 305 on the other side, providing a biasing force pushing the handle end of sled base lock 320 away from sled base 305. Locking element 340 is coupled to sled base lock 320 by virtue of another pin 335. As seen in FIG. 11B and FIGS. 11D-H, the sled assembly 300 is in the lock position when no force is being applied to the sled base lock 320. As seen in FIG. 11C and FIGS. 11I-M, a user can depress a handle of the sled base lock 320 toward the sled base 305. As best seen in FIGS. 11E and 11J, when the sled base lock 320 is in the lock position, the locking element 340 forcible presses against the apertures in the sled assembly 300 that receive the first rail 220 and/or second rail 225. The compression of the locking element 340, provided by the spring pair 330, locks the sled base assembly such that it will not slide along the pylon and rail assembly 200. If the user desires to slide the sled assembly 300, he depresses the handle of the sled base lock 320, compressing the spring pair 330 and pulling the locking element 340 out of contact with the pylon and rail assembly 200. Once the sled assembly 300 is in the desired position, the user simply releases the handle of the sled base lock 320 to lock the sled assembly 300 into the current position. The locking element 340 may alternatively act as a secondary safety lock, with a primary locking mechanism functioning based on the geometry between the sled assembly 300 and the first rail 220 and/or second rail 225. The weight of the sled assembly 300 and any attached portions causes the sled assembly 300 to act as a cantilever with respect to the first rail 220 and/or second rail 225. This mechanism is described more fully below with reference to FIGS. 46-47.

Referring back to the embodiment shown in FIG. 11A, the sled assembly 300 also includes ball assembly 325 configured to support limb holding assembly 400, and ball lock 310 configured to lock the ball assembly 325 in a desired position. Ball lock 310 is coupled to sled base 305 by virtue of screw 350, about which ball lock 310 can pivot relative to sled base 305. Sled base 305 and ball lock 310 each have a portion of a spherical socket 355 in which ball assembly 325 can rotate. The spherical sockets 355 each include a track 360. Ball assembly 365 includes a pair of tabs 365 which fit into track 360. The track 360 limits the freedom of motion of ball assembly 325. When the ball assembly 325 sits within the spherical sockets 355 of the sled base 305 and ball lock 310, the ball assembly 325 is free to rotate about two axes at a particular time. When the ball assembly 325 (and thus limb holding assembly 400) is in the desired position, a user rotates the locking handle 315 until a threaded screw of the locking handle 315 compresses the sled base 305 and ball lock 310. The spherical sockets 355 and ball assembly 325 are dimensioned such that this clamping action provides enough frictional engagement between the sockets 355 and ball assembly 325 to limit further rotation of the ball assembly 325.

In one embodiment, ball assembly 325, as best seen in FIGS. 11N-R, includes a connection portion 370 that couples ball assembly 325 to limb holding assembly 400. Connecting portion 370 includes an aperture 375 that enables a connection to limb holding assembly 400, described in further detail below. Neck portion 371 fits into the ball of the ball assembly 325, allowing the neck portion and connecting portion to rotate relative to the ball of the ball assembly.

In one embodiment, shown in FIGS. 12A-F, a limb holding assembly 400 generally includes a limb support 405, a limb holder frame 410, frame posts 415, support wings 420 and limb holder connector 430. Although the specific embodiment shown represents a limb holder assembly for supporting a foot, other parts of the body could be supported by the system, for example an arm.

The limb support 405, generally shown in a boot shape, can be formed of a plastic, such as polyamide. Limb support 405 is attached to limb holder frame 410. Limb support 405 can include straps (not shown), such as Velcro straps, to secure a limb therein. Alternatively, limb support 405 could be used in conjunction with a limb guard (not shown) that covers the front of the limb. The limb guard could, for example, be shaped to correspond to the front of the ankle, as a separate or unitary piece with the limb support 405, to provide for protection and better stability of the limb.

Limb holder frame 410 can include one or more frames posts 415. The frame posts 415 extend to the sides of the limb holder frame 410. One or more support wings 420 are attached to the frame posts 415. The support wings 420 can include attachment features, such as snaps 425, which mate with a cooperating structure, such as retractor assemblies 500 further described below. The shape of the support wings 420 can be of a virtual circle. The support wings 420 may be positioned so the virtual center of that circle is at the center of the knee joint. This may keep the retractors approximately the same distance and under the same tension through the range of motion of the knee (flexion to extension and vice versa). Other devices could be attached to the limb holding assembly 400 by means of the support wings 420, such as components of a navigation system to help automate movement of the limb holding assembly 400 or to assist an operator using the limb holding assembly 400. Other devices that could attach to support wings 420 include, for example, ankle guards or tibia shields to be used in conjunction with the limb holding assembly 400. Frame posts 415 can be solid posts, or, alternatively, can include an extendable structure, such as telescoping posts. With a telescoping post, a user can extend the support wings 420 to different positions with respect to the limb holder frame 410.

Figure 13B:
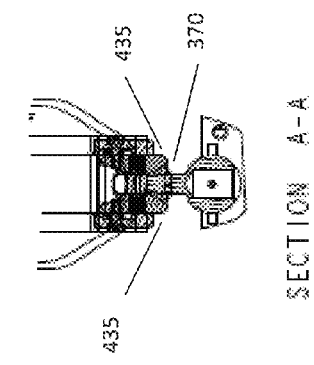
FIGS. 13A-B show a side and cross sectional view the limb holder assembly of FIG. 12A being brought into contact with the sled assembly of FIG. 11A.
Figure 13D:
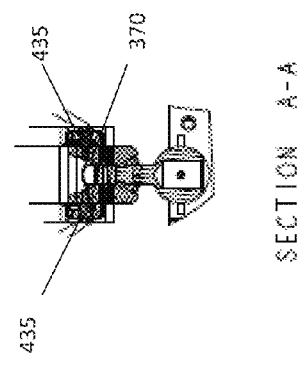
FIGS. 13C-D show a side and cross sectional view the limb holder assembly of FIG. 12A being locked to the sled assembly of FIG. 11A.
Figure 13A:
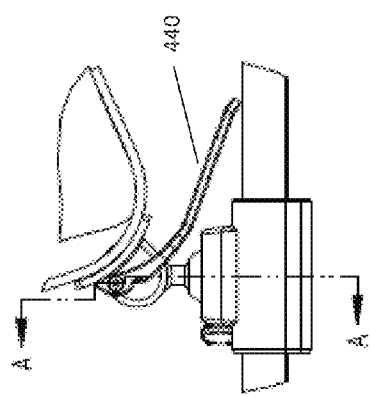
Figure 13C:
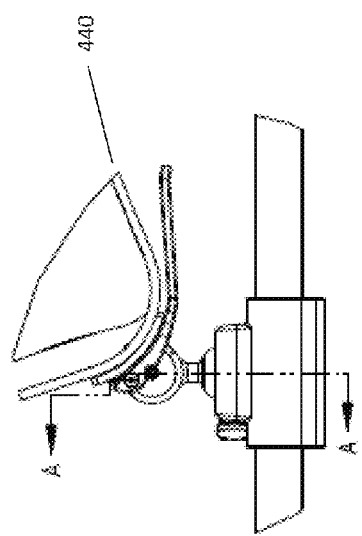
Figure 13E:
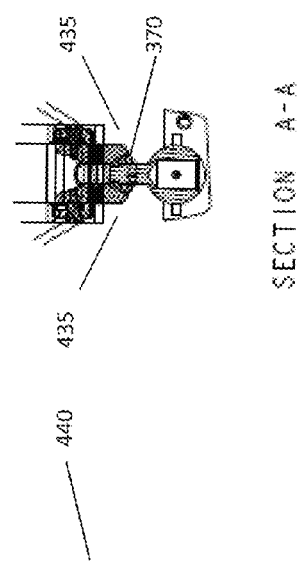
FIGS. 13E-F show a side and cross sectional view the limb holder assembly of FIG. 12A being unlocked from the sled assembly of FIG. 11A.
Figure 13F:
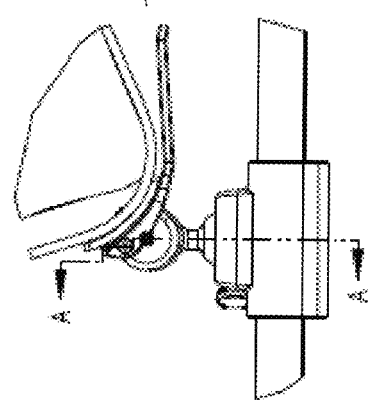
Figure 13G:
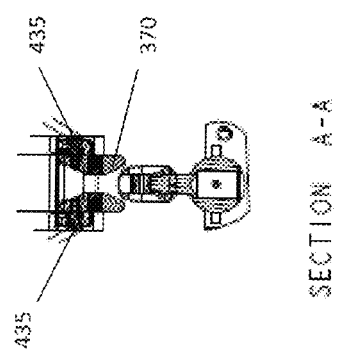
FIGS. 13G-H show a side and cross sectional view the limb holder assembly of FIG. 12A being disconnected from the sled assembly of FIG. 11A.
Figure 13H:
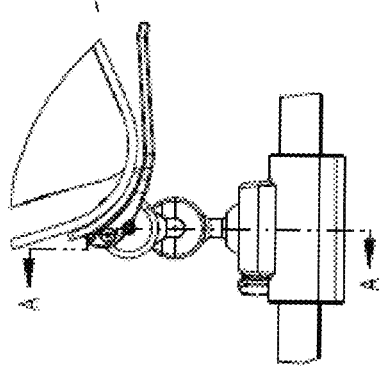

Limb holder connecter 430, one embodiment of which is shown in FIGS. 13A-H, couples limb holder frame 410 to the ball assembly 325 of the sled assembly 300. FIGS. 13A-H each show side and cross sectional views of an event in the sequence of placing the limb holder connector 430 onto the ball assembly (13A-B), locking the limb holder connector 430 onto the ball assembly (13C-D), unlocking the limb holder connector 430 from the ball assembly (13E-F), and removing the limb holder connector from the ball assembly (13G-H). As seen in FIGS. 13A-B, the limb holder connector 430 generally includes two extensions 435 that, acting together, receive the connecting portion 370 of the ball assembly 325. As best seen in FIG. 11N, the connecting portion 370 can include geometrical features to help a user lock the limb holder connector 430 to the connection portion. This may be important if there is poor visibility of the components, such as may occur when a user is standing with both hands holding the limb support 405 and is unable to easily see the bottom of the limb support. Different geometries for the connection portion 370, such as that shown in FIG. 11N, may help the limb holder connector 430 self-align to the connection portion. Limb holder connector 430 may also have a mechanism to lock into the aperture 375 of the connecting portion 360, such as a biased pin (not labeled) that compresses as the two extensions 435 receive the connection portion 370 and snaps into the aperture 375 when appropriately aligned with the aperture 375 due to force from a member, such as a spring. As best seen in FIGS. 13A-H, limb holder connector 430 can include a release mechanism, such as a lever 440, that, when activated, releases limb holder connector 430 from engagement with the connecting portion 370 of the ball assembly 325.

Figures 14B, 14C, 14D, 14E:
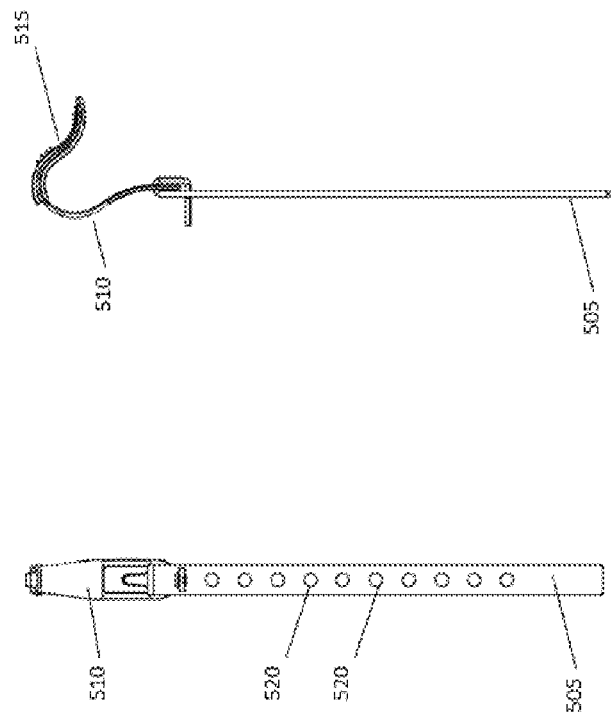
FIGS. 14B-E show multiple views of the retractor assembly shown in FIG. 14A.
Figure 14F:
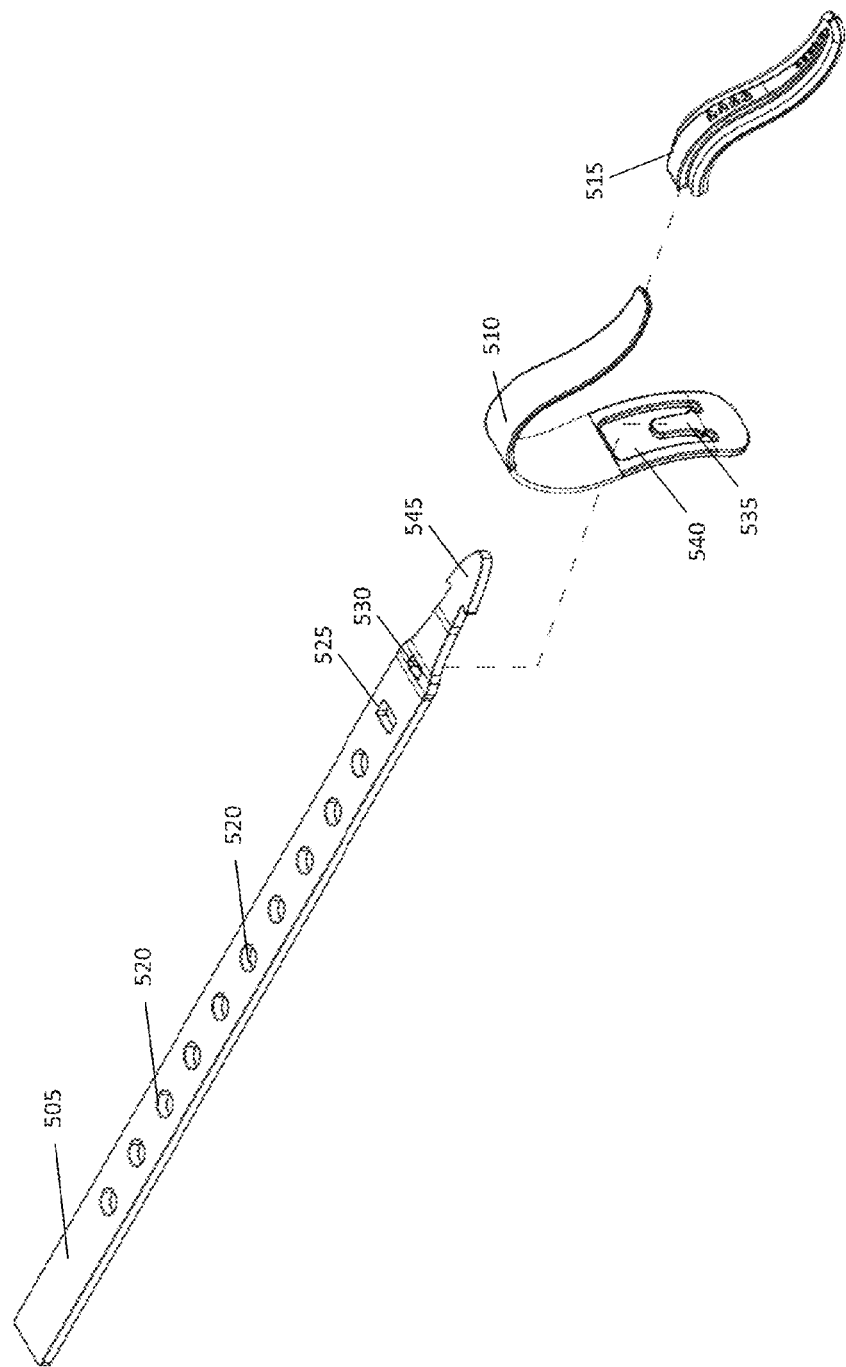
FIG. 14F shows an exploded view of the retractor assembly of FIG. 14A.
Figure 14H:
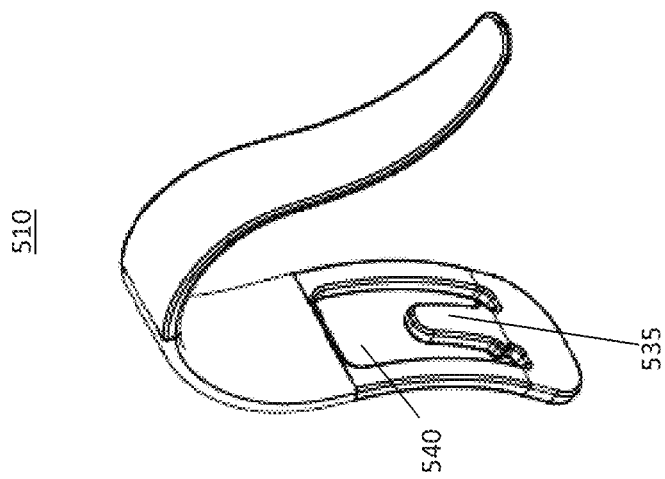
FIGS. 14H-K show multiple views of a retractor head of the retractor assembly shown in FIG. 14A.
Figure 14I:
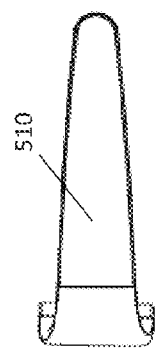
Figure 14J:
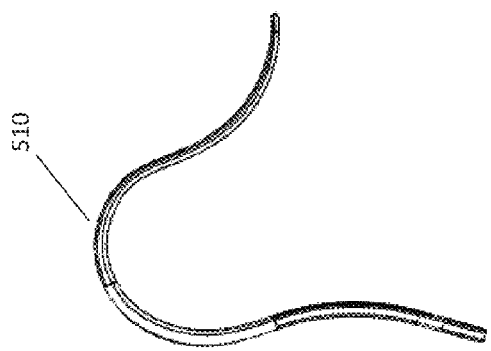
Figure 14K:
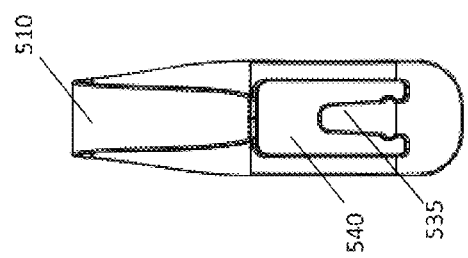
Figure 15A:
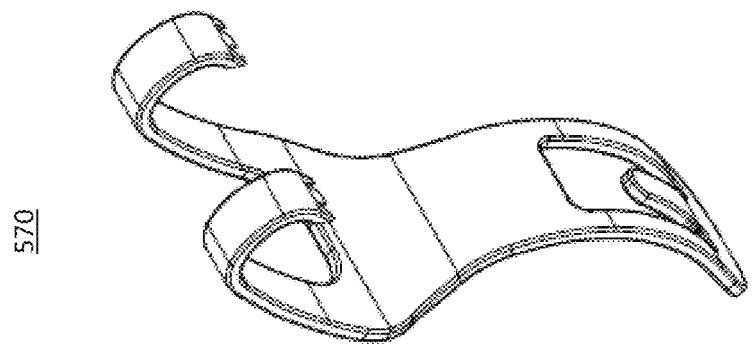
FIGS. 15A-D show perspective views of alternate embodiments of the retractor head shown in FIGS. 14H-K
Figure 15B:
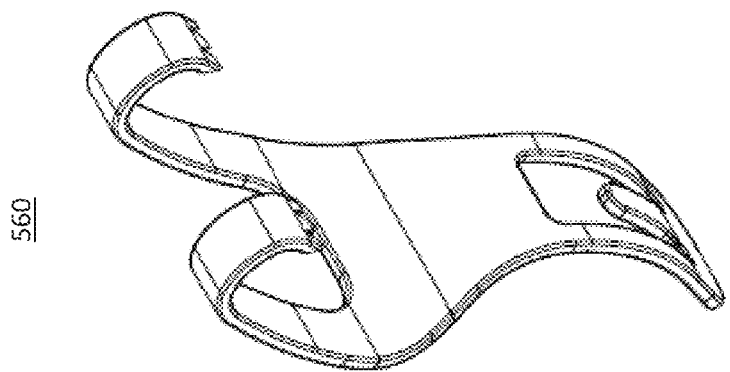
Figure 15C:
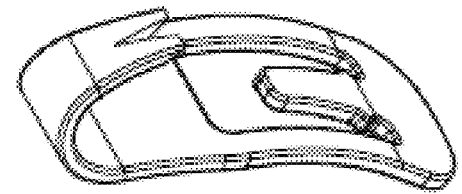
Figure 15D:
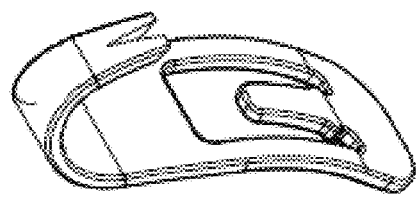

In an embodiment of the invention, limb holder 10 can be used in conjunction with one or more retractor assemblies 500 (as best seen in FIGS. 14A-E), in order to retract tissue during a procedure. One embodiment of retractor assembly 500, as shown in FIGS. 14A-O, generally includes a strap 505, retractor head 510, and retractor cover 515. Strap 505, in one embodiment as best seen in FIGS. 14F-G, is formed from a flexible material. Strap 505 is generally an elongate body with a plurality of apertures formed therein. A first set of apertures 520 are configured to mate with snaps 425 on support wings 420. The straps 505 can have less, more, or the same number of apertures 520 as snaps 425 on support wing 420. The strap 505 also includes additional apertures 525 and 530, as well as tab 545, the use of which is described more fully below.

In one embodiment, retractor head 510, as best seen in FIGS. 14H-K, is generally a curved member configured to retract tissue. The retractor head 510 can be sterilizable and for single or multiple uses and made from various materials, such as plastic, carbon fiber, polyamide or PEEK. Retractor head 510 can also be formed with a void space 540 and a tab 535 extending into the void space 540. The void space 540 is configured to accept the strap 505 and the tab 535 is configured to mate with strap aperture 530. Once tab 535 is secured in aperture 530, the strap tab 545 can be hooked around the bottom of retractor head 510 and inserted into strap aperture 525 for additional stability of the retractor assembly 500, as best seen in FIGS. 14A-F. The final part of the retractor assembly 500 is the retractor cover 515, best seen in FIGS. 14L-O, which slips over the retractor head 510. The retractor cover 515 may be partially or fully covered with one or more sets of textured features, such as teeth 550, to enhance frictional engagement of the retractor assembly 500 with the tissue being retracted. Different retractor heads can be used with the retractor assembly 500 as desired by the user. For example, alternate retractor heads are illustrated in FIGS. 15A-D. Retractor heads 560 and 570 in FIGS. 15A and 15B, respectively, each have two tissue engaging hooks with frictional enhancement features in the form of teeth. Alternate retractor heads 580 and 590 in FIGS. 15C and 15D, respectively, each have a single tissue engaging hook with a more pronounced frictional enhancement feature. Any number of different retractor heads can be used in different combinations in attachment to one or more support wings 420 depending on the particular needs of a procedure or preference of the user.

In a method of use of the embodiment of the limb positioning device shown in FIG. 1, a surgical drape 40 is first placed over the table 20 including over the DIN rail 30. Drape 40 provides a sterile barrier between, on one side, the table 20, including the DIN rail 30, and, on the other side, the patient. The patient is then placed on the table 20, over the drape 40. The lower and upper jaws, 110 and 115, of clamp 105 are then clamped over the drape 40 and over the DIN rail 30. Clamp 105 is positioned along the DIN rail 30 at the location best suited to position pylon and rail assembly 200. The bias provided by spring 130 and block 125 hold the clamp releasably in place over the DIN rail 30. Mounting pylon 205 is then coupled to the clamp 105 by fitting the post 215 in the clamp aperture 150. The extent to which the mounting pylon 205 extends above the clamp 105 is set based on the extent to which the user wants the limb holding assembly 400 to be located above the surface of the table 20. Handle 120 is rotated so that half-spherical portion 122 of the handle mates with half-spherical groove 198 of the block 125. As rotation continues, the upper jaw 115 is pulled toward the handle 120, causing the upper jaw 115 to pivot relative to the lower jaw 110 to close and lock the clamp 105 over the DIN rail 30. This movement also forces the block 125 against the post 215 of the mounting pylon 205, locking the mounting pylon 205 in the desired position as well.

Sled assembly 300 is positioned over bars 220 and/or 225 so the limb holding assembly 400 is located in the position desired by the user. It should be understood that, prior to the positioning of the sled assembly 300, the patient's foot and leg may have already been seated in the limb holding assembly 400. Alternatively, limb holding assembly 400 may already be attached to sled assembly 300. If the patient's foot and leg are in the limb holding assembly 400 and it is attached to sled assembly 300, when sled assembly 300 is moved over the bars 220, 225, the user can determine if the patient's leg will be in the appropriate position, and have the appropriate degree of flexure for the intended procedure.

To position sled assembly 300 along bars 220, 225, the user unlocks the sled assembly 300 as described above, slides the sled assembly 300 with attached limb holding assembly 400 along the bars 220, 225, and releases the sled base lock 320 to lock the sled assembly 300 at the desired position. The position of the sled assembly 300 can be infinitesimally adjusted along the length of the bars 220, 225. In one embodiment, the sled assembly 300 locks along the bars 220, 225 by virtue of the weight of the sled assembly 300 as well as a limb holding assembly 400 and a patients leg. The user can unlock the sled assembly by lifting the sled assembly 300, counteracting the cantilever effect and freeing the sled assembly 300 to be slid along the bars 220, 225. This mechanism is described in more detail with reference to FIGS. 46-47.

Figure 51:
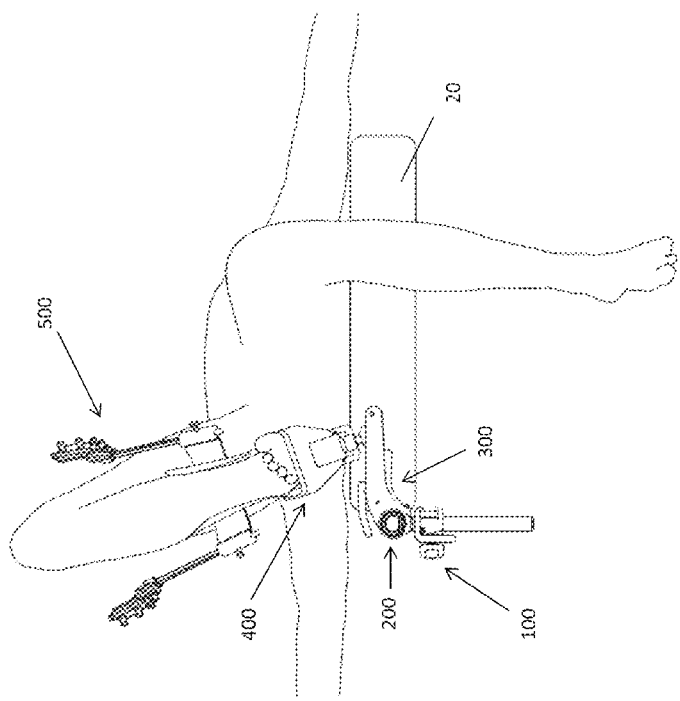
FIG. 51 shows a front view of a leg being held in held in the limb holder shown in FIG. 1 in flexion with the leg laterally rotated.
Figure 52:
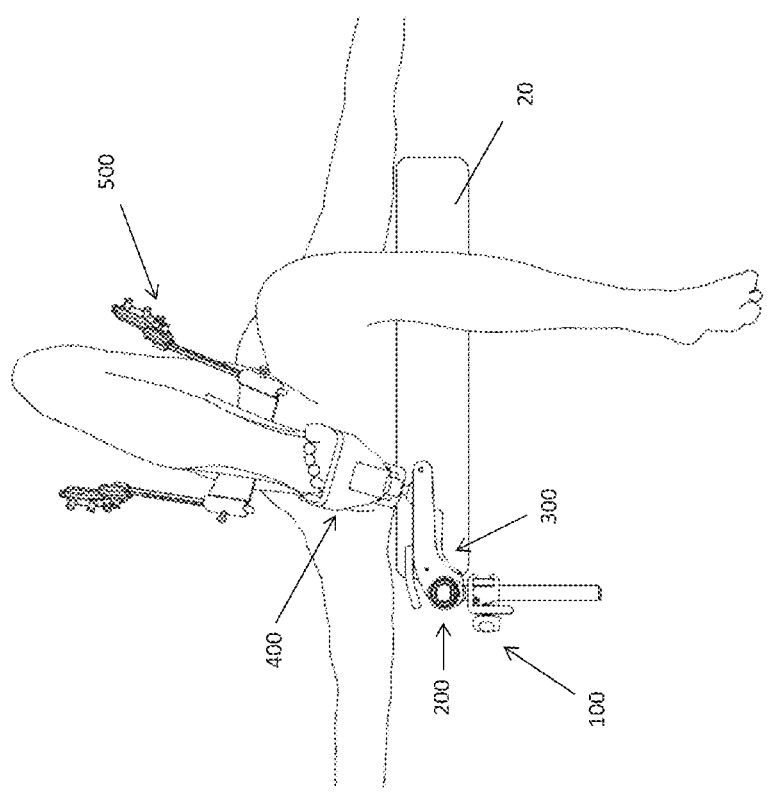
FIG. 52 shows a front view of a leg being held in the limb holder shown in FIG. 1 in flexion with the leg medially rotated.
Figure 53:
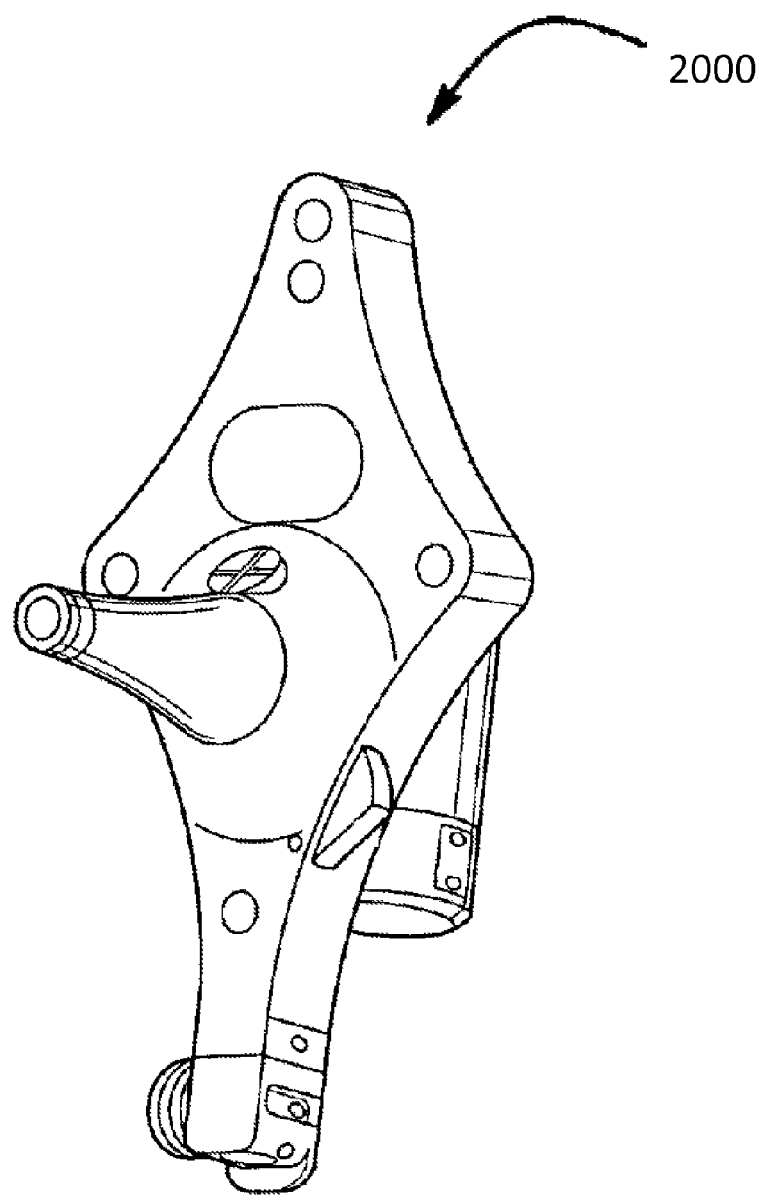
FIG. 53 shows a perspective view of a tracker of a surgical navigation system.
Figure 54:
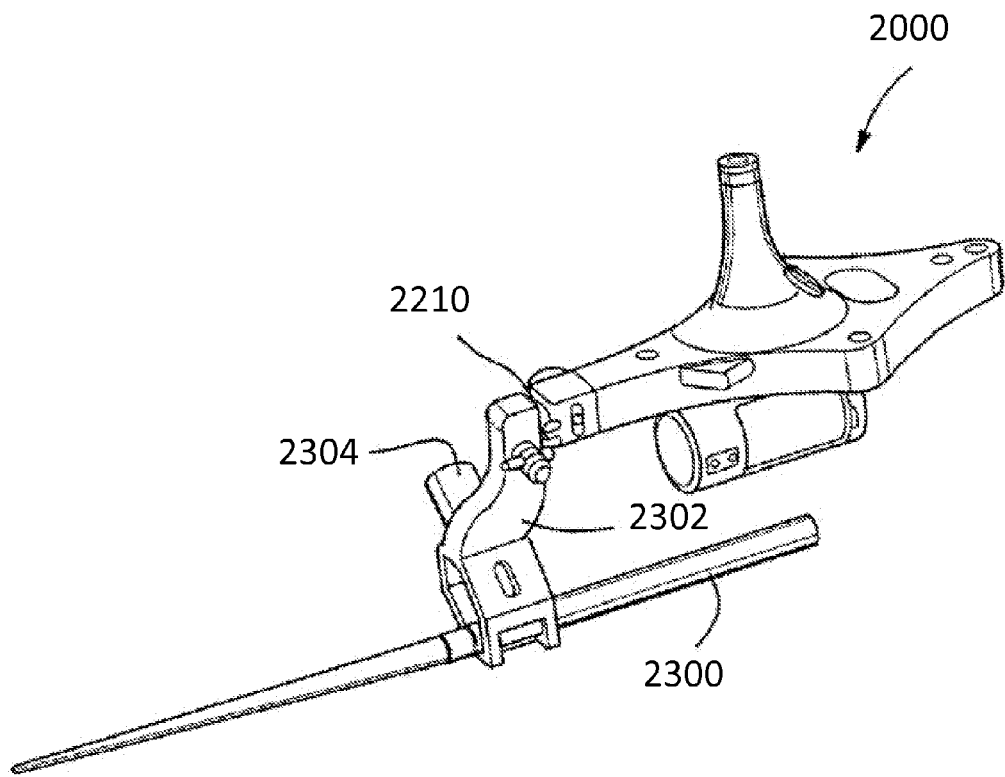
FIG. 54 is a perspective view of the tracker adapted to a general instrument.

The orientation of limb holding assembly 400 can be set along three rotational axes. As part of this process, ball assembly 325, with limb holding assembly 400 attached to connecting portion 370, is rotated as desired by the user. The rotation is carried out while the ball lock 310 is unlocked. For example, a user may move a knee laterally, as shown in FIG. 51, or medially, as shown in FIG. 52, as desired. These are only examples of possible movements of the ball assembly 325, as the rotation is only limited by the anatomy of the patient and the position of the pair of tabs 365 in the track 360 of the spherical sockets 355. When the limb holding assembly 400 is in the desired position, as provided by the ball assembly 325, the user rotates the locking handle 315 to clamp the sled bad 305 and ball lock 310 to fix the ball assembly 325 in the desired position. When the ball assembly 325 is locked in place, and the sled assembly 300 is slid along the bars 220, 225, the connecting portion 370 may still pivot about neck 371.

In the event it is necessary to remove the limb holding assembly 400 from the remainder of the limb position device, the user simply releases limb holder connector 430, as described above, and is able to separate the limb holding assembly 400 from the ball assembly 325. This provides the user the ability to remove the limb holding assembly 400, while maintaining the exact position of the other components of the limb positioning device. If the user needs to reattach the limb holding assembly 400 to the limb positioning device, he will be able to do so and have the limb holding assembly in 400 in the exact orientation it was in prior to the removal. This eliminates the need for the user to go through the positioning steps discussed above for a second time. Alternately, the user can remove the patient's leg along with the limb holding assembly 400, and radically adjust the positions of other components of the limb positioning device. This radical adjustment would be difficult or impossible to accomplish if the patient's leg were attached to the limb positioning device via the limb holding assembly 400 during the radical adjustment.

Figure 48:
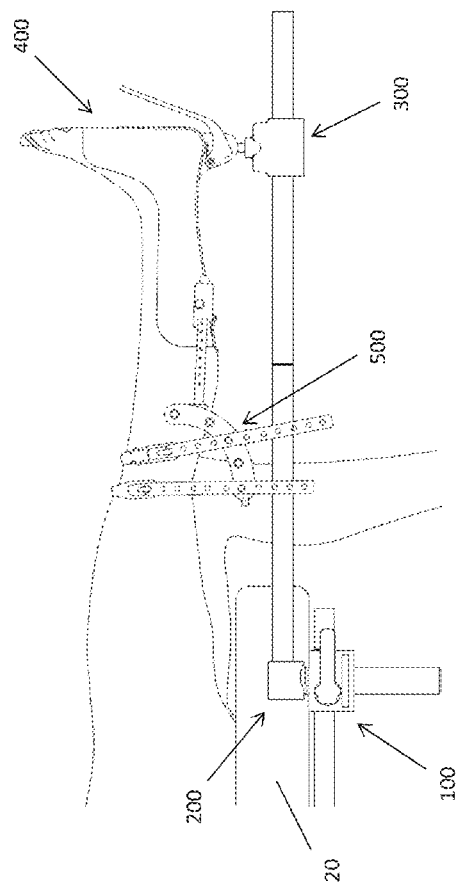
FIG. 48 shows a right-side view of a leg being held in the limb holder shown in FIG. 1 in extension with retractors engaged at a site of operation.
Figure 49:
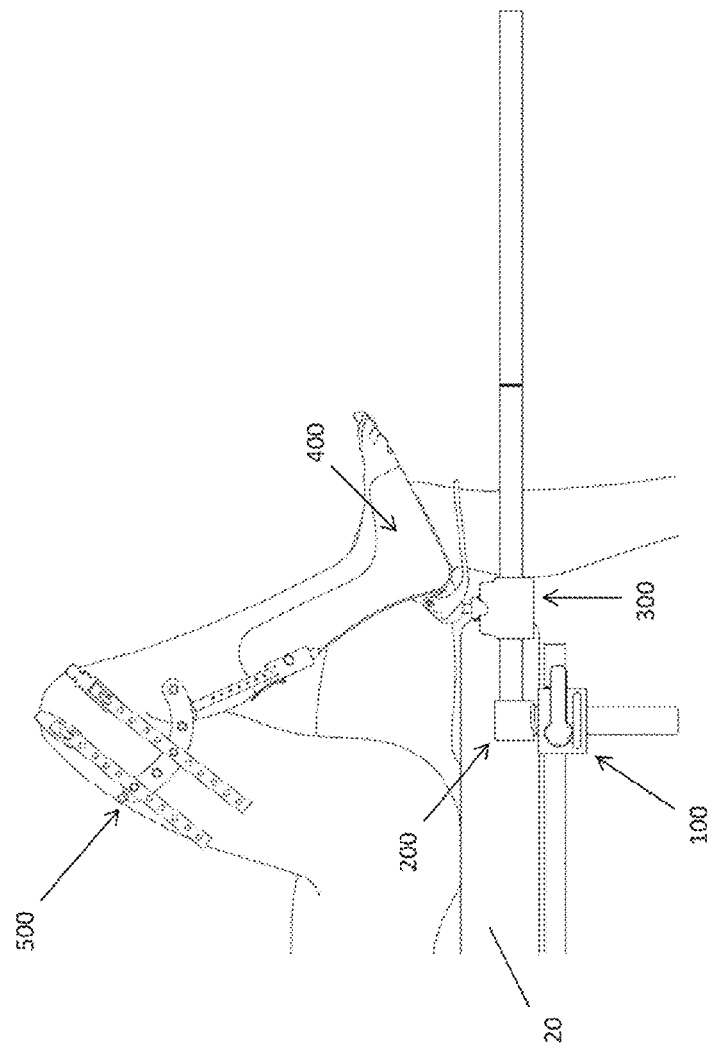
FIG. 49 shows a right-side view of a leg being held in the limb holder shown in FIG. 1 in flexion with retractors engaged at a site of operation.
Figure 50:
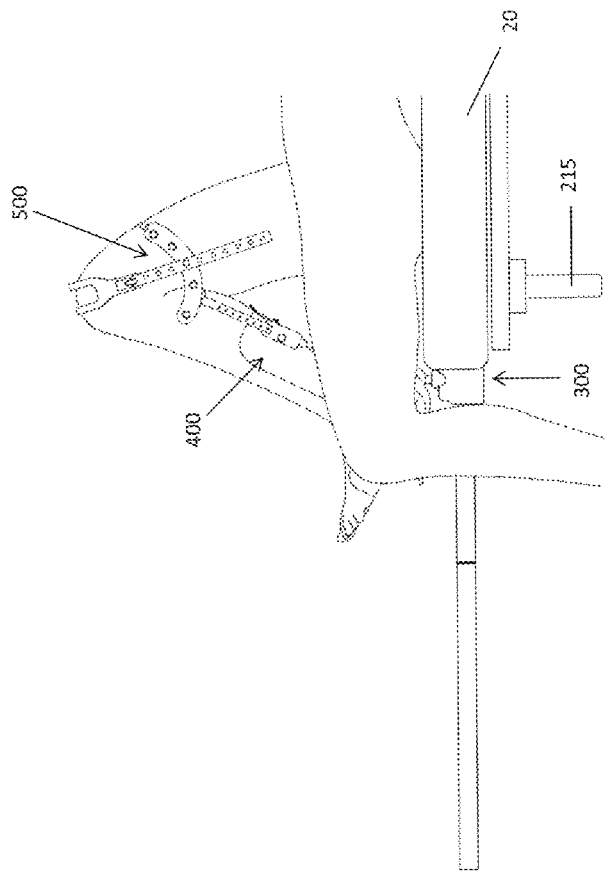
FIG. 50 shows a left-side view of a leg being held in the limb holder shown in FIG. 1 in flexion with retractors engaged at a site of operation.

It should be appreciated that the position of the patient may be adjusted while the limb is attached to the limb holding assembly 400. For example, it may be desirable during a medical procedure on the leg, knee or foot to change position of the limb. One such time when such movement may be desirable is during a procedure on the knee. As part of the procedure, the user may want to bend the leg and knee between extension, as seen in FIG. 48, and flexion, as seen in FIGS. 49-50. While the patient's lower leg and foot are fitted in limb holding assembly 400, and the limb holding assembly remains attached to sled assembly 300 and other components of the limb positioning device, the user can release the sled base lock 320 and slide the limb holding assembly along bars 220, 225 to move the knee from flexion to extension, or vice versa.

During the procedures, a retractor assembly 500 can hold an incision open. Straps 505 hold the retractor assembly 400 to the support wings 420. This feature of the invention eliminates the need to have surgical personnel stand adjacent the incisions solely to hold the retractors in place. Further, because the retractor assembly 500 moves with the limb holding assembly 400, the user may be able to shift the position of the knee without needing to, or minimally needing to, adjust or disconnect the retractor assembly 500 from the limb holding assembly 400.

FIG. 16 illustrates the basic components of another embodiment of a limb holder 1050 of this invention. This particular limb holder 1050 is shaped to hold the foot and lower leg in a fixed position to a medical/surgical table 1052. Here, medical/surgical table 1052 is understood to be a table, a bed or any support structure upon which a patient is disposed. More particularly, the leg holder 1050 is mounted to a DIN rail 1054, a rectangular bar that is often fixedly mounted to the side of a surgical table 1052. Limb holder 1050 includes a boot 1270. Boot 1270 is the component of the limb holder 1050 to which the leg is actually fitted. A tibial shield 1360 (FIG. 36) attached to the boot 1270 extends over the lower leg. The tibial shield 1360 holds the leg in a fixed position to the boot 1270. A clamp 1060, a pylon 1130, a bar 1160, a sled 1180 and a yoke 1220 collectively cooperate to hold the boot 1270 to the DIN rail 1054. More particularly, clamp 1060 holds the pylon 1130 to the DIN rail 1054 at a user-selected position along the rail. Pylon 1130 can be moved vertically relative to the clamp 1060. Bar 1160 extends outwardly from the pylon 1130. Sled 1180 extends outwardly from and can be positioned at different locations along the length of bar 1160. The yoke 1220 is attached to the free end of the sled 1180. The position of the yoke 1220 can be independently set along two axes. The boot 1270 is pivotally mounted to the yoke 1220. Owing to the ability to adjustably set the components of the limb holder 1050 relative to each other, the boot 1270 can be positioned to hold the leg over the surgical table 1052 at plural positions over the table and in orientations that vary along plural axes. Further, the position of the boot 1270 can be reset while the boot remains attached to the other components of the assembly.

As seen in FIG. 17, the clamp 1060 includes lower and upper jaws 1062 and 1064, respectively that are pivotally connected to each other. A knob 1066 extends through the jaws 1062 and 1064. Knob 1066 selectively holds the jaws 1062 and 1064 together in a clamped state. A handle 1068 is moveably mounted to the lower jaw 1062. Handle 1068 is set to selectively lock the mounting pylon 1130 in a fixed position to the clamp 1060.

Figure 18:
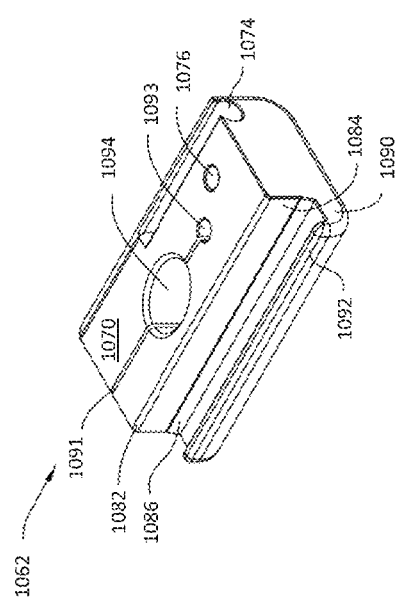
FIG. 18 is a perspective view of the lower jaw of the clamp shown in FIG. 17.
Figure 19:
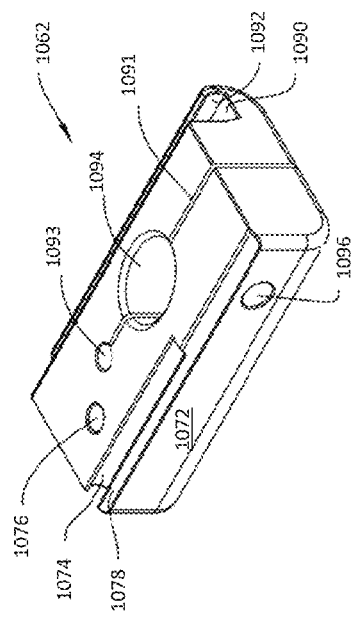
FIG. 19 is an alternative perspective view of the lower jaw of the clamp shown in FIG. 17.

Lower jaw 1062, now described by reference to FIGS. 18 and 19, is formed from a metal such as aluminum or a plastic such as a polyamide. Generally, the lower jaw 1062 is in the shape of a rectangular block. The lower jaw 1062 is shaped to have a top face 1070 that is substantially planar. A bottom face 1073, only the edge of which is seen Figures, is parallel to, spaced from and below the top face 1070. An outer side face 1072 extends generally perpendicularly downwardly from the top face 1070 towards the bottom face. Between the bottom of the side face 1072 and the bottom face 1073, the lower jaw 1062 is formed to have a rounded corner, (not identified).

The lower jaw 1062 is further shaped so as to have a groove 1074 that extends inwardly from the top face 1070. Groove 1074 is spaced inwardly from the outer side face 1072 and extends approximately one-half the length of the jaw 1062. The lower jaw 1062 is shaped so that groove 1074 has an arcuate cross sectional profile. More particularly the jaw 1062 is shaped so that groove 1074 subtends an arc that inscribes an angle of more than 200° and often that inscribes an angle of more than 270°. The opening into the groove in the top face 1070 is narrower than the maximum width across the groove. Below the top face 1070, the width of the groove 1074 extends outwardly and then inward. The widest width portion of the groove 1074, which is located below the jaw top face 1070, has a width equal to the diameter of the circle inscribed by the groove. A threaded bore 1076 (threading not illustrated) extends inwardly from the lower jaw top face 1070. Bore 1076 extends perpendicularly from the top face 1070 to the opposed bottom face 1073.

Between the jaw outer side face 1072 and groove 1074 the top face has a perimeter section 1078. This perimeter section 1078 extends the length of the lower jaw 1062. Unlike the portion of face 1070 the top section on the opposed side of groove 1074, and perimeter section 1078 is not planar. Extending outwardly from the opening into groove 1074 to the outer side face 1072, perimeter section has a small downward curvature.

Lower jaw 1062 is only approximately rectangular in shape. Bottom face 1073 extends further inwardly from the outer side face 1072 than top face 1070. Thus, the lower jaw 1062 is formed to have a step 1090 located below top face 1070 and above bottom face 1073. In some versions of the invention, the top of the step 1090 has a top surface (not identified) that is located a height above the bottom face 1073 that is approximately 20 to 33% of the distance between the top face 1070 and bottom face 1073. Step 1090 extends the full length of the lower jaw 1062. There are three transition surfaces between the top face 1070 and step 1090. A first one of these transition surfaces is curved corner 1082 that extends downwardly from the edge of the top face 1070 adjacent step 1090. A planar first inner face 1084 extends downwardly from corner 1082. First inner face 1084 is in a plane that extends generally perpendicularly to the primary plane of top face 1070. Between the first inner face 1084 and the outer surface of step 1090, the inner jaw is formed to have a second inner face 1086. The second inner face 1086, like the first inner face 1084, is planar. The second inner face 1086 is angled relative to the first inner face 1084 such that the extending downwardly from the first inner face 1084, the second inner face tapers outwardly.

A lip 1092 extends upwardly from the outer edge of step 1090, the edge spaced from faces 1084 and 1086. Lip 1092 extends upwardly to approximately the height where the second inner face 1086 angles away from the first inner face 1084. It should be appreciated that the distance between the second inner face 1084 and lip 1092 is at a maximum where the lip is spaced furthest from step 1090. This width is approximately 0.3 cm greater than the width across the DIN rail 1054. Immediately above step 1090, the width between the second inner face 1084 and lip 1092 is at a minimum. This width is 0.05 cm or less than the width across the DIN rail 1054.

An opening 1094 extends through the lower jaw 1062 from the main portion of top face 1070 to bottom face 1073. Opening 1094 is elliptical in cross section. The opening has a length, (the dimensions along an axis parallel to the longitudinal axis of the lower jaw 1062 that is approximately one-half the overall length of the jaw. Opening 1094 is spaced away from bore 1076. Lower jaw is further formed to define a slot 1091 that extends through the jaw from the top surface 1070 to the bottom surface 1073. Slot 1091 is parallel to side face 1072. The slot 1091 extends inwardly from the end face of the jaw spaced furthest from bore 1076. Slot 1091 is centered on and intersects the major axis of opening 1094. Slot 1091 terminates at a through bore 1093 located between bore 1076 and opening 1094.

Lower jaw 1062 also has a second threaded bore, bore 1096 (threading not illustrated). Bore 1096 extends inwardly from jaw outer side face 1072. Bore 1096 interescts slot 1091. In some versions of the invention, the only portion of bore 1096 that is threaded is the portion located between slot 1091 and face 1084.

Upper jaw 1064, now described by reference to FIGS. 20 and 21, is formed from the same material from which lower jaw 1062 is formed. The upper jaw 1064 is generally rectangular in shape. Upper jaw 1064 therefore has opposed top and bottom faces 1102 and 1106, respectively. The length of upper jaw 1064 is equal to that of lower jaw 1062. Opposed parallel side faces 1104, (only one side face identified,) which extend longitudinally along the jaw 1064, curve outwardly and downwardly from top face 1102. The top face 1102 and side faces 1104 have a collective width that is approximately equal to the width across the jaw bottom face 1106.

A cylindrical rod 1110 extends below jaw bottom face 1106. Rod 1110 has a diameter that is slightly less than the diameter of lower jaw groove 1074. More particularly, in one version of the invention, jaws 1062 and 1064 are shaped so that the diameter of rod 1110 is approximately 0.3 mm less than the diameter of the circle inscribed by lower jaw groove 1074. Rod 1110 has a length substantially equal to the length lower jaw groove 1074. A rectangularly shaped web 1108 extends downwardly from jaw bottom face 1106 so as to hold rod 1110 to the rest of the jaw 1064. Web 1108 suspends rod 1110 a distance of between approximately 2.2 to 11.1 mm below the jaw face 1106. Rod 1110 is positioned so that when the rod is seated in the lower jaw groove 1074, the outer perimeters of the jaws 1062 and 1064 will substantially be in registration. It thus should be appreciated that the rod 1110 is located adjacent the outer portion of the jaw 1064, the portion that is spaced from the table 1052 to which limb holder 1050 is mounted.

Top jaw 1064 is further shaped to have two openings that extend through the jaw from top face 1102 to bottom face 1106. One opening is an oval shaped hole 1112. Jaws 1062 and 1064 are collectively shaped so that when the jaws are mated to form the clamp 1060, top jaw hole 1112 is located above and extends around bottom jaw bore 1076. The second opening is opening 1114. Opening 1114 is elliptically shaped. More particularly, opening 1114 has the same cross sectional dimensions, dimensions in a plane parallel to the jaw bottom face 1106, as bottom jaw opening 1094. When jaws 1062 and 1064 are assembled together top jaw opening 1114 is in registration with and disposed over bottom jaw opening 1094. A tapered counterbore 1115 extends inwardly from jaw top face 1102 into and around bore 1114.

As best seen in FIG. 21, upper jaw 1064 is further formed to have a groove 1116 that extends inwardly, upwardly, from bottom surface 1106. Groove 1116 is located inwardly from the inner side of the jaw 1064, the side that closest to table 1052. The groove 1116 extends the length of the top jaw 1064. The upper jaw 1064 is dimensioned so that the width across the groove 1116 is slightly greater than the width across DIN rail 1054.

Figure 22:
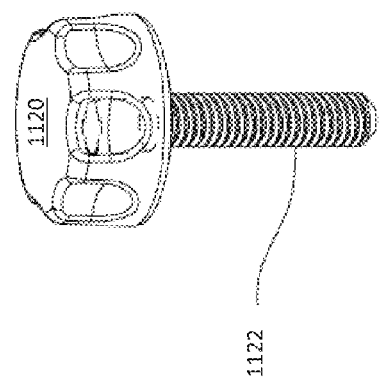
FIG. 22 is a perspective view of the knob that extends between the clamp jaws shown in FIG. 17.

Knob 1066, seen best in FIG. 22, has a head 1120. A cylindrical shaft 1122 formed with threading (not identified) extends downwardly from knob head 1120. Knob shaft 1122 has a length that allows the shaft to extend through upper shaft hole 1112 into lower jaw bore 1076. Shaft 1122 is further dimensioned to engage the threading of lower jaw bore 1076.

Owing to the dimensioning of jaws 1062 and 1064, when clamp 1060 is assembled, web 1108 and rod 1110 essentially hold the outer portion of the lower jaw 1062 away from the overlying bottom surface 1106 of top jaw 1064. The lower jaw 1062 is able to pivot about the longitudinal axis of top jaw rod 1110. Knob 1066 is positioned so that the knob head 1120 is disposed against upper jaw top face 1102 and the shaft 1122 is disposed in lower jaw bore 1076. The rotation of knob therefore causes lower jaw 1062 to move towards or away from the top jaw 1064. More particularly, owing to capture of the lower jaw 1062 by rod 1110 integral with the top jaw, the rotation of the knob 1066 results in the pivoting of the lower jaw around the rod 1110.

The clamp 1060 is attached to the DIN rail 1054 by positioning lower jaw 1062 so that that step 1090 abuts the downwardly directed face of the rail and the upper jaw 1064 so that the top of rail 1054 seats in groove 1116. Clamp 1060 may be infinitesimally set to any location along the length DIN rail 1054 where such positioning results in the desired positioning of boot 1270. The rotation of knob 1066 results in the movement of lower jaw step 1090 towards the upper jaw groove 1116. Jaw faces 1084 and 1086 press against the adjacent surfaces of the DIN rail 1054. The adjacent face of the upper jaw 1064 that defines the outer perimeter of groove 1116 likewise presses against the DIN rail 1054.

Figure 23:
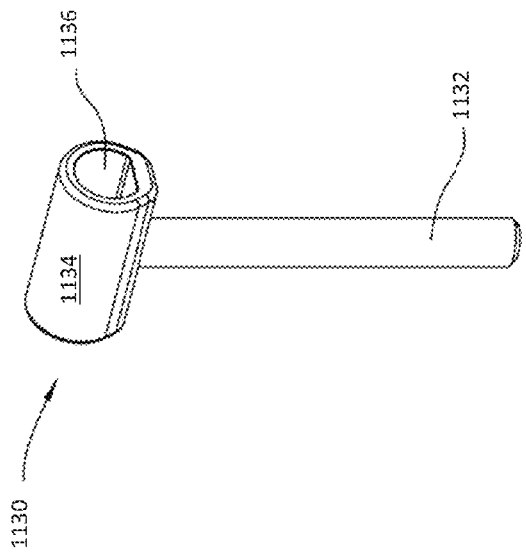
FIG. 23 is a perspective view of the pylon shown in FIG. 16.

Pylon 1130, as seen in FIG. 23, is a single piece unit. The pylon 1130 includes a post 1132 typically formed from metal such as aluminum. Post 1132 has a cross sectional shape that is elliptical. More particularly, the post 1132 has a cross sectional shape that allows the post to slip fit within clamp openings 1094 and 1114. The post 1132 has a side-to-side width that is approximately 0.3 mm less than the length across jaw openings 1094 and 1114.

A head 1134, also part of pylon 1130, is mounted to the top of post 1132. Head 1134 is a tube like structure. The head has a length such that the opposed ends of the head extend beyond the sides of post 1132. A bore 1136 extends axially through the head 1134. Bore 1136 thus has a center longitudinal axis that is perpendicular to the longitudinal axis of the pylon post 1132. While pylon head 1134 is approximately tube like in shape, the features of the head are not completely circular. Bore 1136 does not have a circular cross sectional profile. Instead, the bore has a cross sectional profile of a circle form which a section has been removed. The bore is defined by an arcuate and straight inner wall sections of the head 1134, inner wall sections not identified. The arcuate inner wall section inscribes an arc of approximately 280°. The straight inner wall section extends between the opposed ends of the arcuate inner wall section. The straight wall section is a plane perpendicular to the longitudinal axis of the post 1132 and defines the section of bore 1136 closest to the post. The distance across the straight inner wall section of head 1134 is less than the diameter of the circle partially inscribed by the arcuate inner wall section. The actual body of the head 1134 that defines the bore has an outer surface geometry that generally corresponds to the bore-defining inner walls of the head.

For reasons of assembly, an opening (not illustrated) extends upwardly from the bottom of pylon head 1136 into bore 1138. The top end of post 1132 is press fit in this opening. In some versions of the invention the pylon post 1132 and head 1138 are fabricated out of a single piece of metal.

Figure 24:
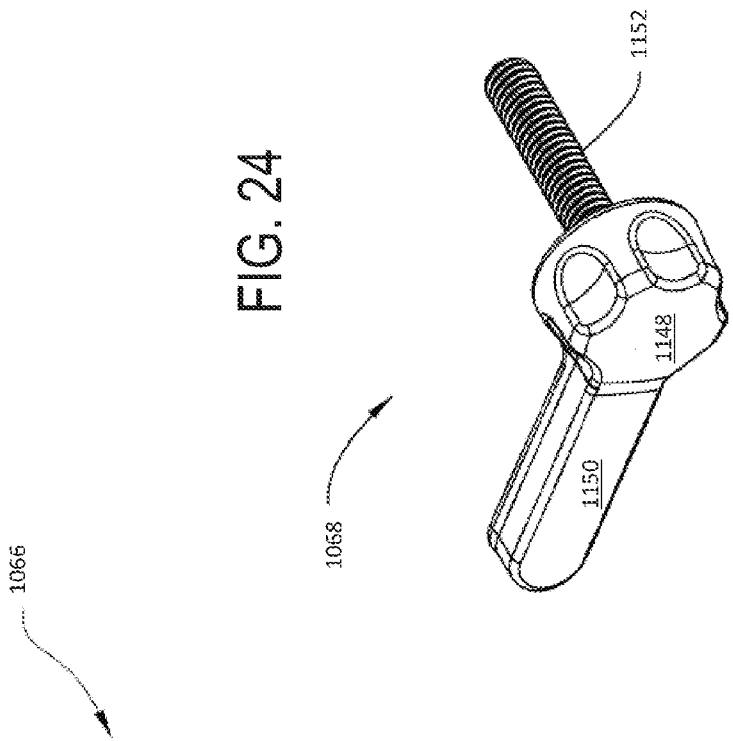
FIG. 24 is a perspective view of a handle that secures the pylon to the clamp shown in FIG. 17.

Handle 1068, the handle that holds pylon 1130 to clamp 1060, is now described by reference to FIG. 24. The handle 1068 has a cylindrical head 1148. A lever arm 1150 is formed integral with the head and extends radially away from the center axis of the head. Collectively, handle head 1148 and lever arm 1150 are dimensioned to fit in the hand. Typically handle head 1148 and lever arm 1150 are formed from single piece of aluminum.

The handle 1068 also has a stem 1152. Stem 1152 is extends away from and has a diameter less than that of head 1148. The stem 1152 is formed from metal. The outer surface of handle stem 1152 is threaded (threading not identified). Handle stem 1152 is dimensioned to threadably engage bore 1096 internal to clamp lower jaw 1062.

Pylon 1130 is mounted to clamp 1060 by sliding the pylon post 1132 into the openings 1094 and 1114 in, respectively jaws 1062 and 1064. More particularly, the pylon post 1132 is disposed between the outer surface of the DIN rail 1054 disposed in jaw openings 1094 and 1114 and the opposed faces internal to the jaws that define the openings. Handle 1068 is rotated so as to cause the portion of the lower jaw between the outer face 1072 and slot 1091 to compress inwardly towards the portion of the jaw closest to the DIN rail 1054. More specifically, the jaw pivots around bore 1093. This deflection of the jaw 1092 decreases the length of the minor axis of opening 1094. Lower jaw 1062 thus clamps pylon post 1132 in opening 1094 at a fixed height.

Figure 25:
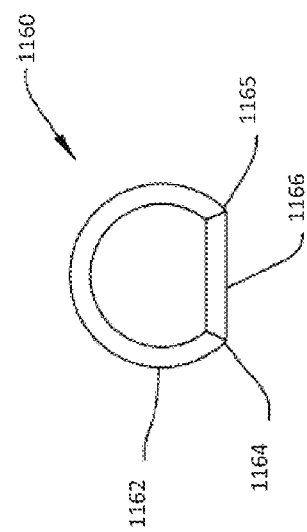
FIG. 25 is an end view of a bar that extends from the pylon shown in FIG. 23.
Figure 26:
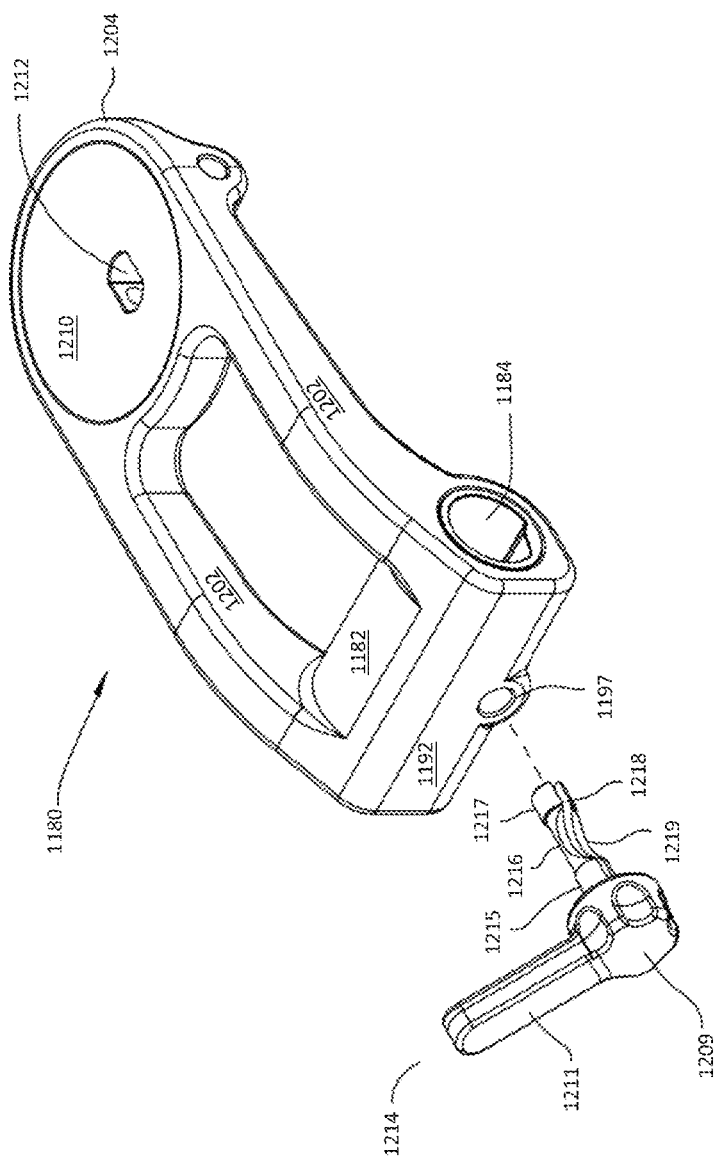
FIG. 26 is an exploded view of a sled and a handle, used to releasably secure the sled to a bar, shown in FIG. 16.

Bar 1160, seen in FIGS. 16 and 25, is a single piece elongated structure that may be solid or hollow. The bar 1160 may be formed from carbon fiber or a metal such as stainless steel. From the side view of FIG. 25 it can be seen that the bar 1160 has a cross sectional section of that, while arcuate, is not that of a complete circle. Specifically, the bar has curved face 1162 only the edge of which is seen in FIG. 26. Face 1162 subtends an arc of approximately 270°. A planar face 1166 extends between the two ends of curved face 1162. Opposed corners 1164 and 1165 function as the transition surfaces between the adjacent ends of curved face 1162 and planar face 1166. Arbitrarily, corner 1164 is located outward of the table 1052 to which bar 1160 is attached; corner 1165 is located proximal to the table.

Bar 1160 is dimensioned to fit in pylon head bore 1136. Thus the bar 1160 is shaped so that bar curved face 1162 subtends the same arc as arcuate inner wall section of pylon head 1134 that defines bore 1138. In one version of the invention, the bar is formed to be press fit in pylon head bore 1138. As seen in FIG. 16, one end of the bar 1160 is fit in bore 1138.

Figure 27:
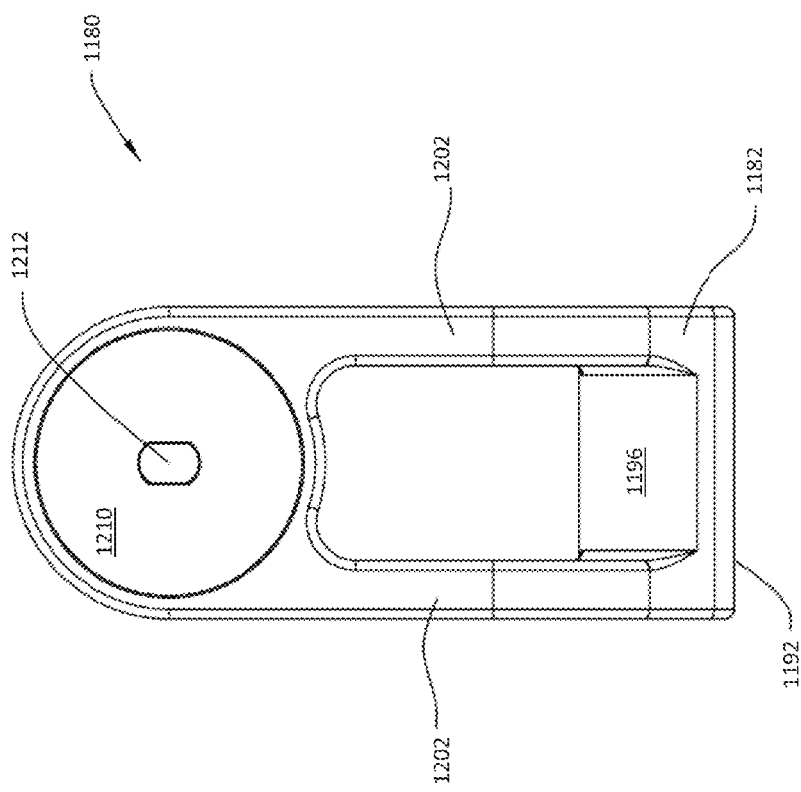
FIG. 27 is a top plan view of the sled shown in FIG. 26.
Figure 28:
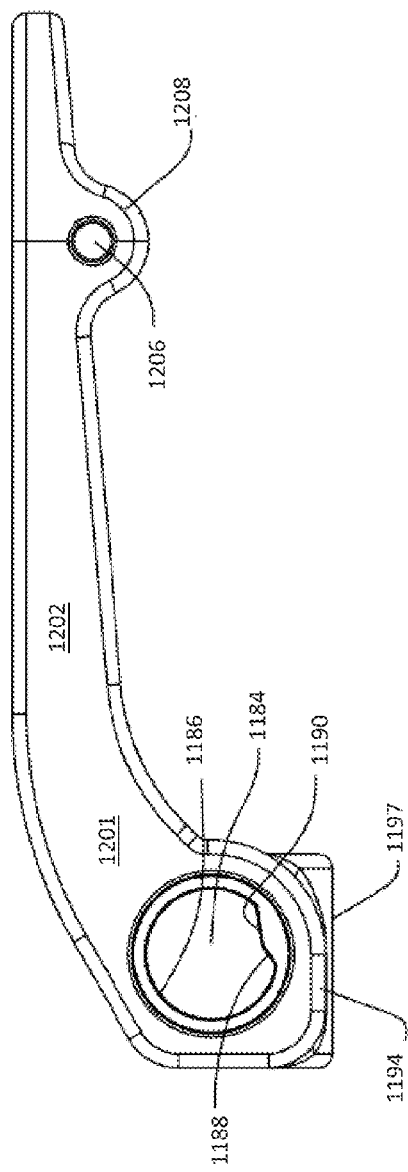
FIG. 28 is a side view of the sled shown in FIG. 26.

As seen in FIGS. 26-28, sled 1180 is formed from a single piece of metal. The sled includes a tube like base 1182 that is slidably disposed over bar 1160. Base 1182 includes a longitudinally extending bore 1184. Bore 1184 is the void space internal to the base through which bar 1160 extends.

The bore 1184 is defined by a number of faces internal to sled base 1182, the edges of which are seen best in FIG. 28. The largest face is arcuate face 1186. Arcuate internal face 1186 subtends an angle of approximately 314°. Sled 1180 is further formed so that arcuate face 1186 has a radius of curvature that is approximately 0.3 mm larger than the radius of curvature of bar arcuate face 1162. Two flat faces, faces 1188 and 1190, connect the opposed ends of arcuate face 1186 so as to complete the definition of the perimeter of bore 1184. Flat faces 1188 and 1190 meet an angle. This angle, when measured within bore 1184, is greater than 180°. One flat internal face, face 1188 in FIG. 28, has a width that is less than the width of the complementary flat face, face 1190. Here "width" is the distance across the face along an axis perpendicular to the longitudinal axis through bore 1184. Face 1188 extends upwardly from the position near the bottom of bore 1184. Flat face 1188 is at an angle such that when the sled 1180 is mounted to the bar 1160, the face is angled towards the surgical table 1052. Flat face 1190 extends inwardly, towards the surgical table 1052, from the end of face 1188 spaced from arcuate face 1186.

On the outside, the sled base 1182 is shaped to have two flat external faces 1192 and 1194 and a curved external face 1196. Flat external face 1192 lies in a vertical plane. When limb holder 1050 is assembled, face 1192 is parallel to the major surfaces of the DIN rail 1054. The second external flat face, face 1194, the edge of which is called in FIG. 28, forms the bottom, downwardly directed, outer surface of the sled base 1182. Curved external face 1196 extends inwardly and downwardly from flat external face 1192 to meet the inner end of flat external face 1194.

Sled base 1182 is further formed to have a rib 1197 that projects below external face 1194. Rib is located in the middle of the base 1182 and extends perpendicularly to the longitudinal axis of the base. A bore 1198 extends through rib 1197. As best seen in FIG. 47A a section of bore 1198 intersects bore 1184.

Parallel arms 1202 extend away from the opposed ends of sled base 1182. Each arm 1202 has a shoulder section 1201 that is the section of the arm that actually extends away from the base 1182. Each arm shoulder section in addition to extending away from the base 1182, extends upwardly a small distance, approximately 1.9 cm. The sections of the arms 1202 spaced from sled base 1182 generally just extend away from the base.

A dish 1204, also part of sled 1180, is disposed between the ends of the arms 1202 spaced from the base 1182. Dish 1204 is generally circular in shape. A rib 1208 is integrally formed with and extends below dish 1204. Rib 1208 extends diametrically across the dish 1204 and is parallel to sled base 1182. The rib 1208 is formed to have a threaded bore 1206, (threading not illustrated). Sled 1180 is further formed so that dish 1204 has a top face 1210 with a concave, downwardly curved shape. A through opening 1212 extends downwardly from the center of dish face 1210, the base, the lowest portion of dish face 1210 and through rib 1208. Dish opening 1212 thus intersects rib bore 1206. The sled is formed so that dish opening 1212 has an oval shape.

A knob, 1214 now described by reference to FIG. 26, is mounted to sled base 1182. Knob 1214 has a head 1209 and lever arm 1211 essentially identical to the head and lever arm 1148 and 150, respectfully, of knob 1066. A stem extends away from the head 1209 and is coaxial with the head. The stem is formed with three sections 1215, 1216, and 1217 that are cylindrical and coaxial with head 1209. Section 1215 is closest to head 1209; section 1216 extends from section 1215; and section 1217 extends from section 1216 and is further from the knob head. Stem sections 1215 and 1217 have the same diameter. This is a diameter that is slightly greater than the diameter of sled base bore 1198. Stem section 1216 has a diameter less than that of sled base bore 1198. A single slot 1218 extends diametrically across each of stem sections 1215, 1216 and 1217. Slot 1218 extends the length of stem 1213. Slot 1218 allows the portions of stem sections 1215 and 1217 on the opposed sides of the slot 1218 to move in on towards each other when the stem is seated in sled base bore 1198. Knob stem 1213 is thus designed to tightly rotate in the sled base bore 1198. Knob 1214 is further formed so that there is arcuate notch 1219 in stem section 1216. Notch 1219 has a curve that is centered on an axis perpendicular to the longitudinal axis of the stem 1215. The radius of curvature of notch 1219 is slightly greater than the radius of curvature of bar arcuate face 1162. A recess (seen but not identified in FIG. 47B) is present at the end of stem section 1217. A tab (seen but not identified in FIG. 47B) integral with the sled base 1160 extends into the stem recess. This arrangement holds knob 1214 to the sled 1180.

Figure 29:
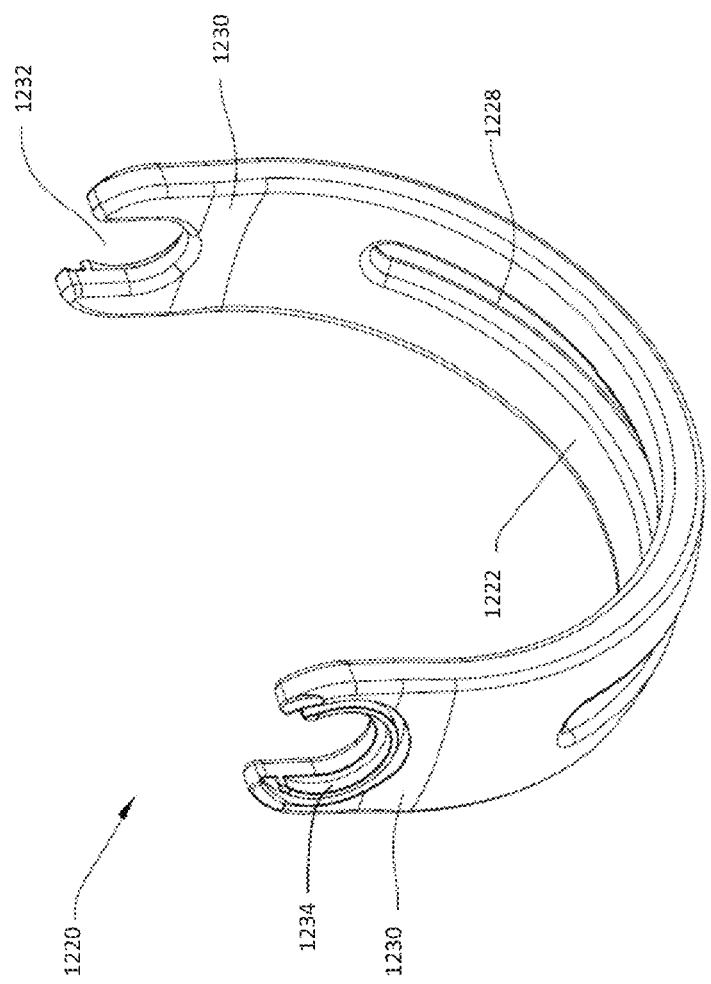
FIG. 29 is perspective view of the yoke shown in FIG. 16.
Figure 31:
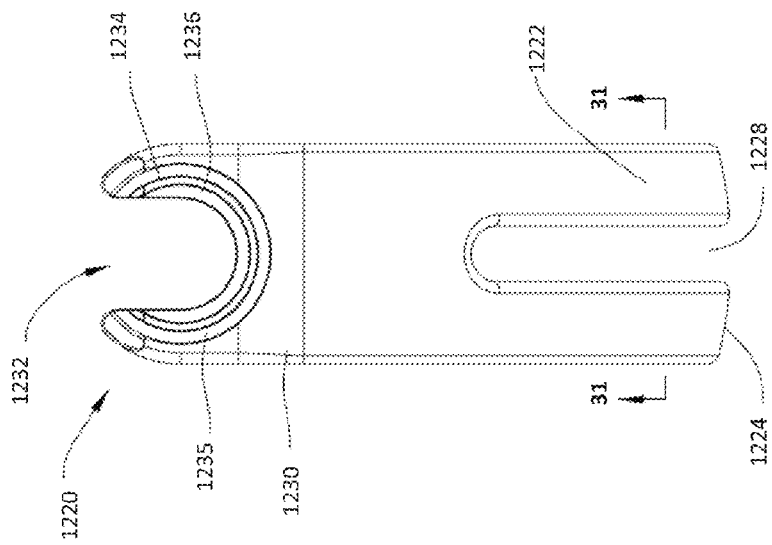
FIG. 31 is a partial cross sectional view of the yoke taken along line 31-31 of FIG. 29.

The yoke 1220, now described by reference to FIGS. 29 31, is a single piece unit formed from aluminum. The yoke 1220 is shaped to have a base 1222 that is generally in the shape of semi-circular beam. Yoke 1220 is further formed so that in cross section, base 1222 has a concavo-convex profile. Specifically, base has a downwardly directed face, face 1224 with a convex cross sectional profile. The opposed face, face 1226 of yoke base 1222 has a concave profile. Yoke base 1222 is further formed to have an elongated slot 1228. Slot 1228 is centered on the longitudinal axis of the yoke base. The yoke 1220 is further formed so that slot 1228 does not extend to the opposed ends of the yoke base 1222. For reasons apparent below, the yoke 1220 is further shaped so that the base outer surface 1224 has both longitudinal and lateral radii of curvature that are equal to the radius of curvature of sled dish face 1210.

An arm 1230 extends outwardly from each end of the yoke base 1222. The yoke 1220 is further formed so that a notch 1232 extends inwardly from the outer end of each arm 1230. Each notch 1232 is generally U-shaped. Yoke 1220 is further formed so that each arm 1230 has a step surface 1236 that is recessed inwardly relative to the outer face of the arm 1230. (Here the arm "outer surface" is the surface that faces away from the opposing yoke arm 1230.) Each step surface 1236 is located inwardly from the outer perimeter of the arm 1230 in which the surface is formed. The inner perimeter of each step surface 1236 defines the outer perimeter of the associated yoke notch 1232. The outer perimeter of each step surface 1236 is in arcuately shaped and subtends an angle of approximately 275°

Figure 30:
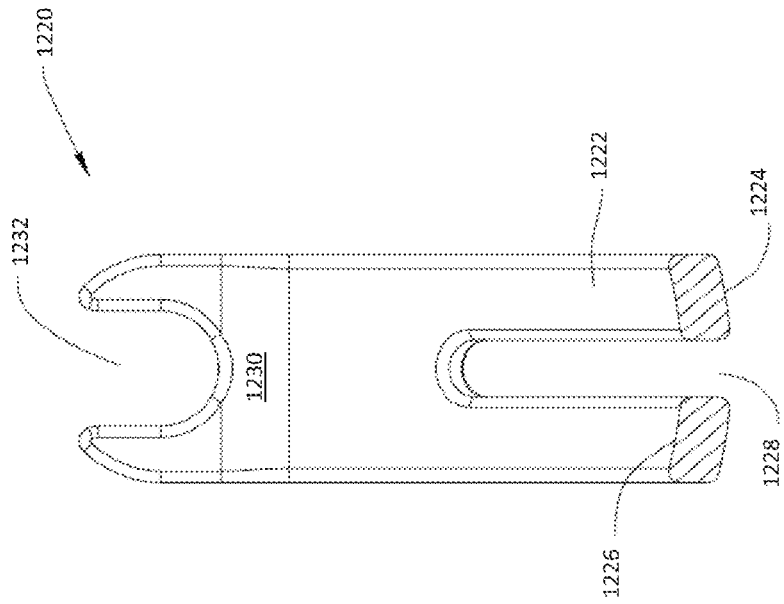
FIG. 30 is a side view of the yoke shown in FIG. 29.

An arcuately spaced rib 1234 extends outwardly from each step surface 1236. Each rib 1234 subtends the same angle as the associated step surface 1236. Each rib 1234 is spaced outwardly from the inner perimeter of the associated step surface and inwardly from the outer perimeter of the associated step surface. Owing to the inward spacing of the rib 1234 from the outer perimeter of step 1236, each yoke has an arcuate groove 1235 defined by the step and rib 1234. As seen best in FIG. 30, each arm notch 1232 intersects the associated rib 1234, groove 1235 and step surface 1236.

As depicted in FIGS. 16 and 32 when limb holder 1050 is assembled, the yoke 1220 is positioned so that the outer surface 1224 of the yoke base 1222 seats against face 1210 of the sled dish 1204. A yoke lock 1240 both seats over the yoke base inner face 1226 and extends through yoke slot 1228. The yoke lock 1240 also extends into sled dish opening 1212 to seat in sled rib 1208. A knob 1260 rotatably mounted in one of the sections of sled rib 1208 selectively holds the yoke lock 1240 against the yoke 1220.

Figure 34:
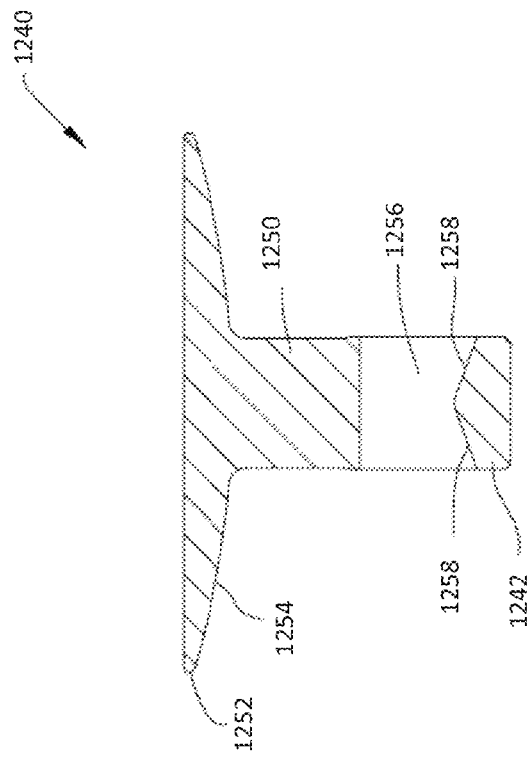
FIG. 34 is a cross sectional view of the yoke lock shown in FIG. 33.
Figure 33:
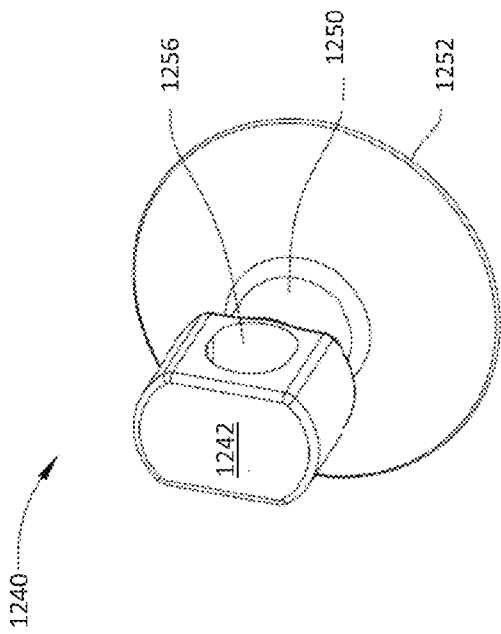
FIG. 33 is a perspective view of the underside of the yoke lock shown in FIG. 32.

The yoke lock 1240, shown in detail in FIGS. 33 and 34, is a single piece component formed from stainless steel. The yoke lock 1240 is shaped to form a foot 1242. When viewed in cross section in a plane perpendicular to the longitudinal axis of the yoke lock, foot 1242 has an oval cross sectional profile. More particularly, the foot 1242 is dimensioned to seat in and slip fit in sled dish opening 1212.

A leg 1250 extends upwardly from foot 1242. Leg 1250 is cylindrical in shape. Leg 1250 is coaxial with the center axis that extends bottom-to-top through foot 1242. The yoke lock is shaped so that leg 1250 has a diameter no greater than the width across foot 1242. Yoke lock 1240 is further formed to have a cap 1252 that extends upwardly and outwardly from leg 1250. Specifically, the cap has a bottom surface 1254 that is convex in that as the surface extends radially away from the leg 1250 the surface curves upwardly. Collectively, the yoke 1220 and yoke lock 1240 are shaped so that the radius of curvature of the cap bottom surface is equal to the radius of curvature of yoke body inner face 1226. Yoke cap 1252 has a diameter equal to the width across the yoke body inner face 1226. The top surface of the yoke cap, (surface not identified) is planar.

The yoke lock 1240 is further formed to have a bore 1256 that extends through the foot 1242. Bore 1256 extends between the two parallel planar faces of the foot 1242. The yoke lock 1240 is formed so that the opposed openings into bore 1256 are oval in shape (openings not identified). Bore 1256 is not constant in cross sectional dimensions along its length. As seen in FIG. 34, internal to yoke foot 1242 are two ramp surfaces 1258. Ramp surfaces 1258 are symmetric relative to the longitudinal axis that extends through top-to-bottom through the yoke lock 1240. Each ramp surface 1258 extends upwardly from the opening into the adjacent opening into the bore. Ramp surfaces 1258 meet at the intersection of the yoke longitudinal axis and the minor axis of the yoke foot. Extending inwardly from each opening into bore 1256, the length across bore decreases. The length across bore 1256 is at a minimum in the plane where the two ramp surfaces 1258 meet.

Figure 35:
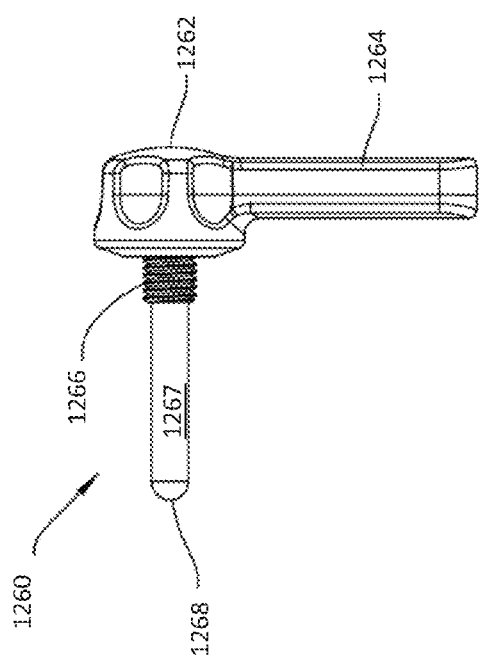
FIG. 35 is a side plan view of the handle, shown in FIG. 26, fitted to the sled that latches the yoke lock.

Knob 1260, now described in detail by reference to FIG. 35, has a head 1262 and lever 1264 similar to head and lever 1148 and 1150, respectively, of handle 1068. A multi-section metal stem extends axially away from knob head 1262. The stem has a first section, section 1266 adjacent the boss 1264. (Not illustrated is the section of the stem embedded in the boss 1264) Stem section 1266 is formed with threading, (not identified). The threading is dimensioned to engage with the threading internal to the ends of bore 1206 internal to sled rib 1208. Extending forward from the stem first section is a second section, section 1267. Stem section 1267 has a diameter less than that of stem section 1268. At the most forward end of stem section 1267 the stem is formed to have nose 1268. Nose 1268 is semi-spherical in shape.

Figure 36:
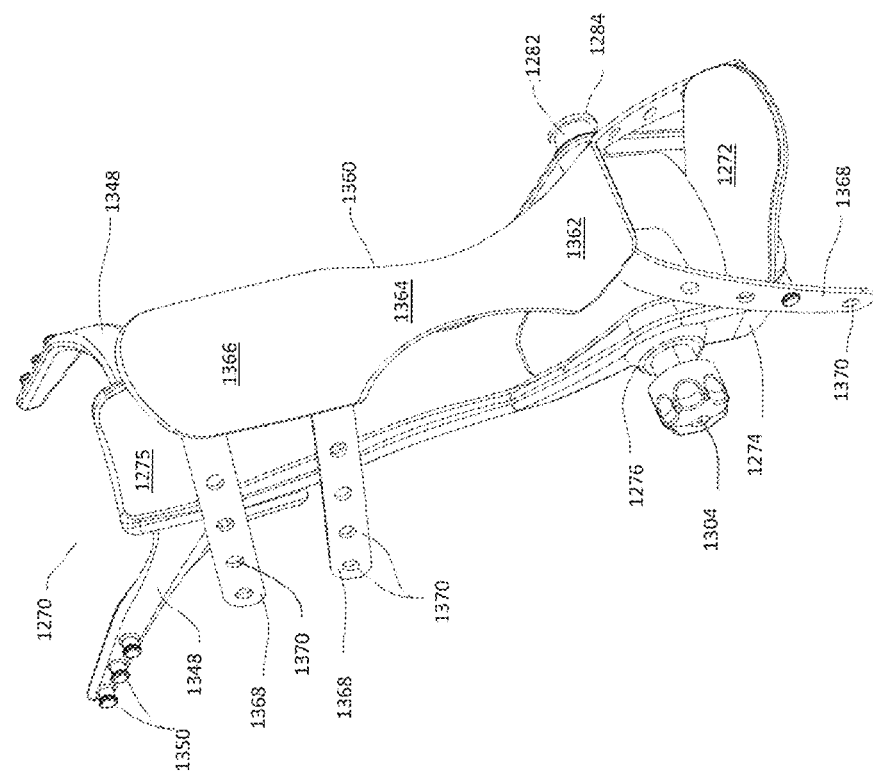
FIG. 36 is a perspective view of the boot shown in FIG. 16 with a complementary tibia shield.
Figure 37:
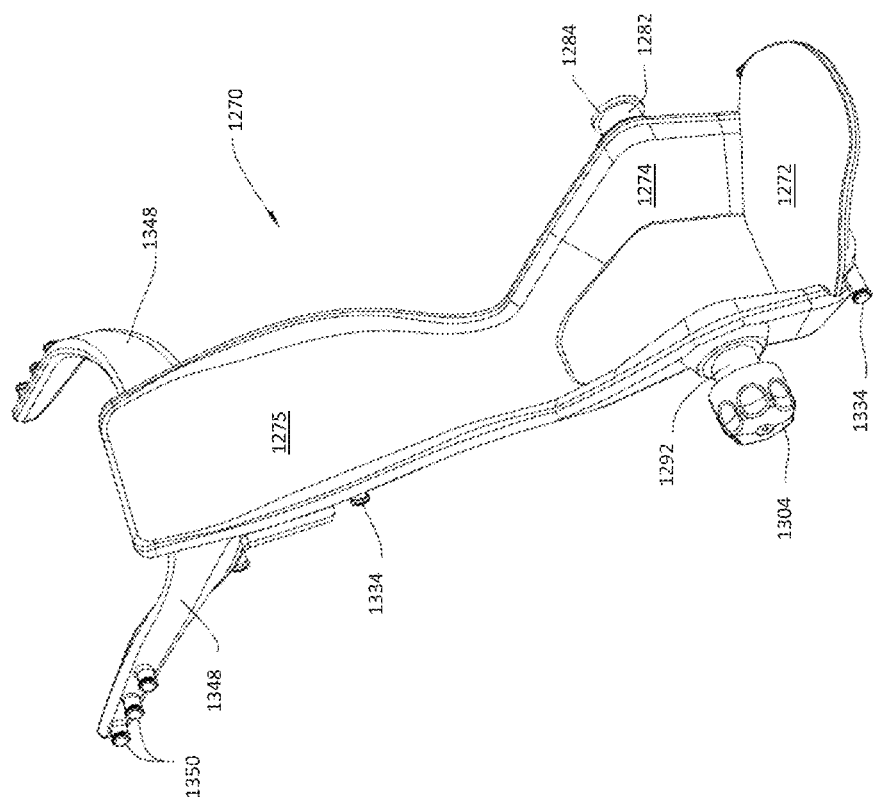
FIG. 37 is a perspective view of the boot shown in FIG. 36 without the tibia shield.
Figure 38:
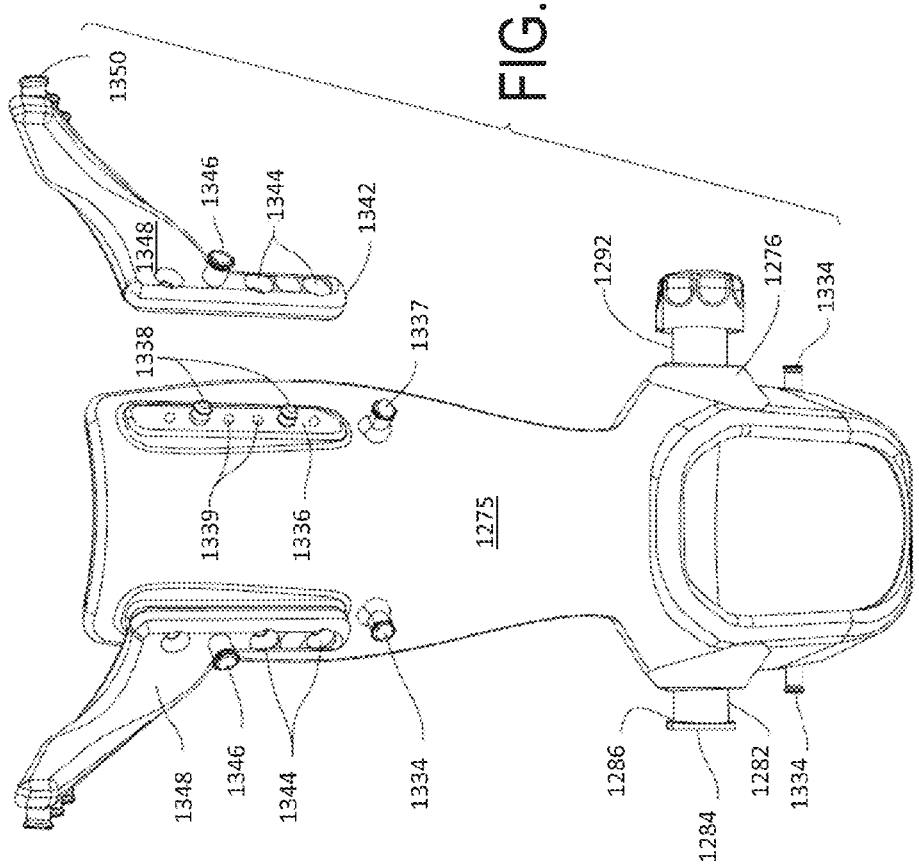
FIG. 38 is a plan and partial exploded view of the back of the boot shown in FIG. 37.

The limb holder boot 1270, now initially described by reference to FIGS. 36-38 is formed from a plastic such as polyamide. Boot 1270 is formed to have a foot plate 1272. Foot plate 1272 is generally in the form of outsized representation of the surface of the human foot. The foot plate 1272 may be shaped to have a length less than of an adult foot. Two ankle plates 1274 extend upwardly from the opposed sides of foot plate 1272. The ankle plates 1274 extend upwardly from the sides of the foot plate 1272 at locations immediately forward of the heel end of the foot plate. Each ankle plate 1274 has two sections (individual sections not identified). A first section of each ankle plate 1274 extends essentially straight up from the foot plate 1272. A second section of the ankle plate 1274 angles upwardly and rearwardly away from the first section. A boss 1276 extends outwardly from each ankle plate 1274. Each boss 1276 extends outwardly from the associated ankle plate 1274 where the plate second section angles away from the first section.

The ankle plates 1274 second sections curve inwardly toward each other and meet at a calf plate 1275, also part of the boot 1270. Calf plate 1275 is approximately in the form of an oversized representation of the back of the calf. Two wings 1348 are adjustably mounted to the back of the calf plate 1275. As discussed below, wings hold retractors 1390 in place. The retractors 1390 hold open an incision cut in the leg of the patient.

From FIG. 38 it can be seen that two posts 1282 and 1292 extend outwardly from the opposed sides of boot 1270. Each post 1282 and 1292 extends outwardly from a separate one of the bosses 1276. Each post 1282 and 1292 has a diameter that is approximately 0.25 mm less than the width across yoke notches 1232. The relative dimensioning of the yoke 1220 and the boot posts 1282 and 1292 allows the boot posts to both closely slip fit in the yoke notches 1232 and pivot around the yoke arms 1230.

Figure 39:
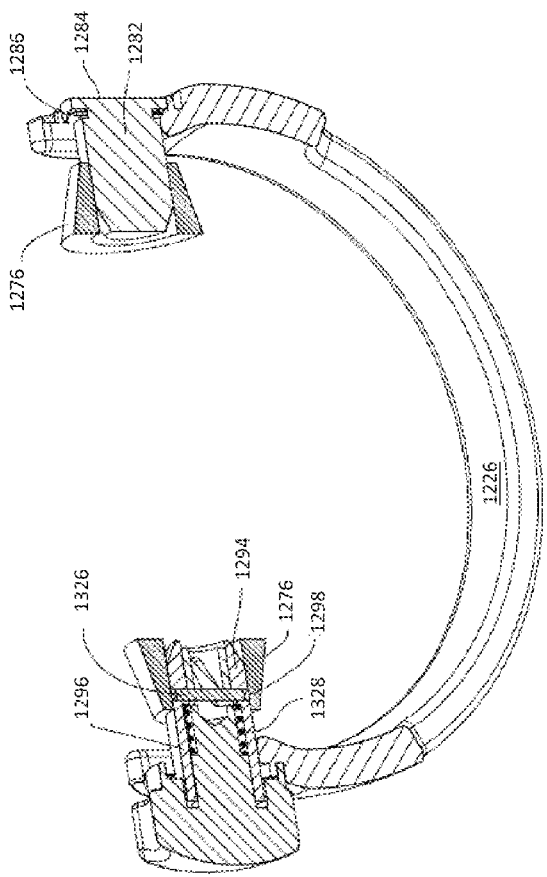
FIG. 39 is a cross sectional view of how a boot lock holds the boot shown in FIG. 36 in a fixed axial position to the yoke.

A static head 1284 is mounted to the free end of post 1282. Head 1284 has a diameter greater than the width across the yoke notches 1232. A rim 1286, a portion of which is best seen in FIG. 39, extends inwardly from head 1284, towards the adjacent ankle plate 1274. Rim 1286 has a diameter and width thereacross such that the rim can fit in the annular groove 1235 in the adjacent yoke arm 1230. A wave spring, not illustrated, is disposed over post 1282. The wave spring extends between the outer surface of the boss 1276 from which post 1292 and that adjacent inner surface of the yoke arm 1230

From FIG. 39 it can be seen that post 1292 is tube-like in shape. Post 1292 has a stem internal section 1294 and an exposed section 1296. The outer diameters of post sections 1294 and 1296 are equal. Post section 1292 has a wall thickness greater than the wall thickness of post section 1294. Post stem section 1292 is seated in the bore 1277 formed in the associated boot boss 1276. Two coaxial bores 1298 (one identified) extend radially through post internal section 1294. The bores 1298 are located immediately adjacent the step internal to the post 1292 between post sections 1294 and 1296. Post exposed section 1296 extends outwardly from the stem section 1294. Post exposed section 1296 is the section of the post 1292 that projects away from the associated boot boss 1276 and is seated in one of the yoke notches 1232.

Figure 40:
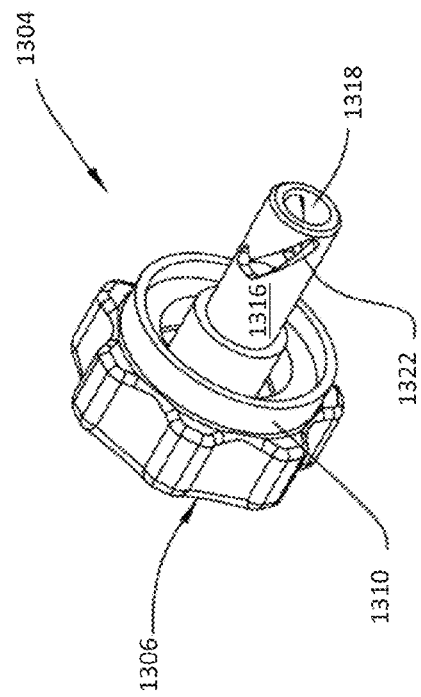
FIG. 40 is a perspective view of the boot lock shown in FIG. 37.
Figure 42:
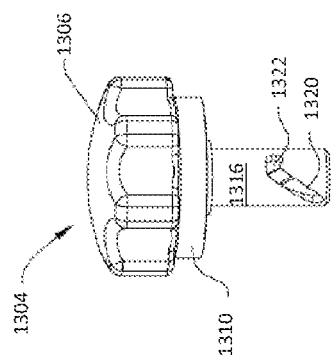
FIG. 42 is a side view of the boot lock shown in FIG. 40.
Figure 41:
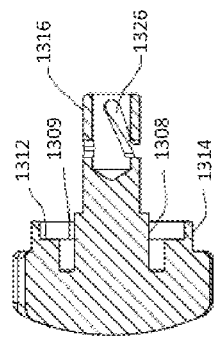
FIG. 41 is a cross sectional view of the boot lock shown in FIG. 40.

Boot lock 1304, now described by reference to FIGS. 40-42, is a single piece unit that is typically formed from metal. The boot lock 1304 has a circular head 1306. Not identified are the indentations in the knob head 1306 that function as finger holds. A neck 1308 and a skirt 1310 both extend inwardly from the knob head 1306. Both neck 1308 and skirt 1310 are coaxial with the knob head 1306. Neck 1308 has an outer diameter less than that of head 1306. More specifically, neck 1308 has a diameter that allows the neck to move within the open bore of exposed section 1296 of boot post 1292.

Skirt 1310 circumferentially surrounds and is radially spaced from knob neck 1308. Boot lock 1304 is shaped so that skirt 1310 has an upper section 1312 adjacent head 1306 and a lower section 1314 spaced from the head. The outer diameter of skirt sections 1312 and 1314 are essentially identical. The wall thickness of the upper skirt section 1312 is greater than the wall thickness of the adjacent lower skirt section. More particularly, Boot lock 1304 is formed so that there is an annular groove 1309 between the outer circumferential wall of neck 1308 and the adjacent radially spaced away inner wall of skirt upper section 1312. Boot lock 1304 is shaped so that the end of post exposed section 1296 can seat in groove 1309.

Skirt lower section 1314 extends longitudinally away from and has a wall thickness less than that of the adjacent skirt upper section 1312. The boot lock 1304 is shaped so that the skirt lower section 1314 can seat in the grooves 1235 internal to the yoke arms 1230.

A cylindrical leg 1316 extends outwardly from knob neck 1308. Leg 1316 is coaxial with neck 1308. The leg 1316 has an outer diameter that allows the leg to slidably fit in the bore of the stem section 1294 of boot post 1292. A closed end bore 1318 extends inwardly from the free end of leg 1316. Leg 1316 is further formed to have two diametrically opposed slots 1320. Slots 1320 extend through the portion of leg 1316 that defines bore 1318. Slots 1320 are helically shaped. Each slot 1320 is formed with a detent 1322. Each detent 1322 extends downwardly away from the top end of the slot 1320 with which the detent is integral.

The portion of the leg 1316 adjacent the neck 1308 as well as the knob neck 1308 is seated in boot post exposed section 1296. A pin 1326, seen in FIG. 39, extends through post bores 1298 and boot lock leg slots 1320. Pin 1326 thus holds boot lock 1304 to boot post 1292. A coil spring 1328 is disposed in the bore of the boot post 1292 exposed section 1296 around the adjacent portion of knob leg 1316. One end of spring 1328 is disposed between the stepped surface that is transition between post sections 1294 and 1296. This is the static surface against which spring 1328 bears. The opposed end of spring 1328 is disposed around an annular step located around the portion of knob leg 1316 closest to head 1306.

As part of the process of assembling the limb holder 1050 of this invention, spring 1328 is disposed around knob leg 1316. The knob leg 1316 is then disposed in post 1292. Pin 1326 is then fitted to post stem section 1294. In this manufacturing step, the pin 1326 is inserted through knob slots 1320. The seating of the pin in post 1292 and through the knob leg 1316 holds the knob to the post. Post stem section 1294, with the attached lock knob 1304, is then press fit and/or adhesively secured in boot boss bore 1277.

Returning to FIG. 38, it can be seen that four pins 1334 extend outwardly from the outer surface of boot 1270. Each pin 1334 has a stem and a head that extends outwardly over the end of the stem (heads and stems not identified.) One pin 1334 extends outwardly from below the opposed sides of foot plate 1272. The pins 1334 that extend outwardly from below the foot plate 1272 may be longitudinally aligned.

The remaining two pins 1334 extend outwardly from the outer surface of the calf plate 1275, the surface opposite the surface against which the patient's leg rests. The pins 1334 integral with the calf plate 1275 are centered over separate lines that angle in towards and intersect each other at a location forward of the inner surface of the calf plate.

Spaced slightly above each calf plate pin 1334, boot 1270 is formed to have a rib 1336, one rib 1336 identified. The ribs 1336 extend outwardly from the calf outer surface. Each rib 1336 has a planar outer surface (not identified). Two posts 1338 extend outwardly from the outer surface of each rib 1336. Each rib 1336 is formed to have a number of closed end threaded bores 1339. Bores 1339 are linearly aligned. Posts 1338 are linearly aligned with and located between bores 1339.

Integral with each wing 1348 is an elongated spine 1342. Each spine 1342 is in the form of an elongated bar. Spines 1342 are generally of the same length as ribs 1336. Each spine 1342 has a flat surface (not illustrated) that is directed towards the complementary rib 1336. A number of openings 1344 extend through each spine 1342. The spine is shaped so that when the spine is disposed against the complementary rib 1336, at least two wing openings 1344 are aligned with two of the closed end bores 1339 formed in the rib 1336. Fasteners, not illustrated, extend through the openings 1344 into the rib bores 1339 so as to removably hold the wings 1348 to the boot 1270. There are more rib bores 1339 than wing openings 1344. This feature of the invention makes it possible to adjust the height of the wings 1348 relative to the boot 1270.

The inner surface of each wing spine 1342 is formed with a set of closed end bores or a groove, bores/groove not illustrated. When a wing 1348 is attached to the boot 1270 the rib posts 1338 seat in these spine bores (or groove). This seating of the rib post 1338 in the spine 1342 enhances the strength of the mechanical connection between the boot 1270 and the spine 1342.

A pin 1346 extends outwardly from the spine 1342. Pins 1346 are identical in shape to pins 1334.

Each wing 1348 extends away from the longitudinal axis of the spine 1342 with which the wing is integral. More particularly, the wing and spine component is shaped so that when this component is attached to the boot 1270, the wing flares rearwardly away from and slightly outwardly from the boot. Plural pins 1350 are attached to each wing 1348. The pins 1350 extend outwardly so as to extend away from the associated boot. Pins 1350 are the same general shape as pins 1334 and 1346.

The tibial shield 1360, seen in FIG. 37, holds the leg and foot to the boot 1270. The tibial shield 1360 is formed from a flexible material such as neoprene. The depicted tibial shield 1360 has a foot section 1362. Shield foot section 1362 is of constant width and is dimensioned to extend over the upper portion of the foot seated in the boot 1270. Extending upwardly from the foot section 1362, the shield 1360 has an ankle section 1364. The shield 1360 is shaped so that opposed sides edges of the ankle section are concave. As the ankle section 1364 extends away from the foot section 1362, the edges first curve inwardly and then curve outwardly from each other. Tibial shield 1360 also has a tibia section 1366 located immediately above ankle section 1364 The opposed sides of the tibia section 1366 are parallel. In the illustrated version of the invention, the sides of tibia section 1366 are spaced apart the same distance the oppose sides of the shield foot section 1362 are spaced apart. When the tibia shield 1360 is fitted over the patient, the shield extends over the portion of the leg seated in the boot 1270.

Flexible straps 1368 integral with the tibia shield 1360 hold the shield to the boot 1270. Straps 1368 are made of material such as neoprene. Each strap 1368 is formed with a set of holes 1370. Holes 1370 have a diameter that allow the straps to be fitted over boot pins 1334 and 1346 while allowing the pin heads to retain the straps. Mechanical fasteners, not illustrated, secure the straps 1368 to the shield 1360.

In the depicted version of the invention, one strap 1368 extends outwardly from each side of the shield foot section 1362. When the shield 1360 is secured to the boot 1270, straps 1368 that extend outwardly from the shield ankle section are fitted over the pins 1334 located below the foot plate 1272. Two straps 1368 extend outwardly from the shield tibia section 1366. The lower pair of straps 1368, the straps adjacent the shield ankle section 1364, are fitted to the opposed boot pins 1334 that extend from the calf plate 1275. The upper pair of straps that extend outwardly from the shield tibia section 1366 are fitted to the pins 1346 that extend outwardly from the spines 1342.

Figure 44:
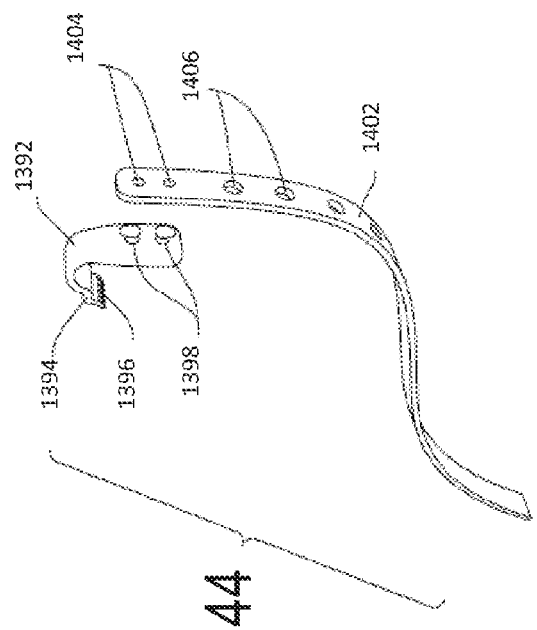
FIG. 44 is an exploded view of the retractor shown in FIG. 43.
Figure 43:
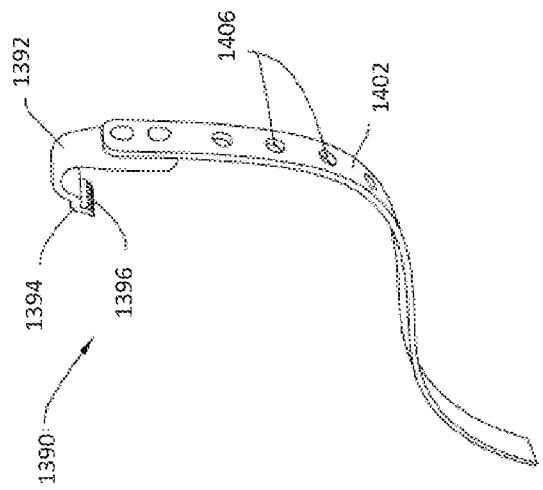
FIG. 43 is a perspective view of a retractor used with the limb holder shown in FIG. 16.

A retractor 1390 used with the limb holder 1050 of this invention is now described by reference to FIGS. 43 and 44. Retractor 1390 includes a head 1392. If the head 1392 is sterilizable, the head is formed from plastic or carbon fiber. Use once heads 1392 are formed from sterilizable plastic such as polyamide or PEEK. The head 1392 is shaped to hold open the tissue defining the incision into the patient. In the depicted version of the invention the head 1392 is in J-shaped. An outwardly directed step 1394 is formed in the short length section of the head. Teeth 1396 extend outwardly from the short length section of the head. Two pins 1398 extend outwardly from the long length section of the head 1392. Pins 1398 extend outwardly from the surface of the long length section directed away from teeth 1396. Each pin 1398 is formed with a head (not identified).

A flexible strap 1402, also part of retractor 1390, is attached to the head. Strap 1402 may be formed from the same material from which tibial shield straps 1368 are formed. Strap 1402 is formed with two openings 1404. Openings 1404 are dimensioned to receive pins 1398 so that the pins hold the strap 1402 to the retractor head 1392. The strap 1402 is also formed with multiple openings 1406. Openings 1406 are designed to receive a post 1350 that extends outwardly from one of the wings 1348.

Figure 45:
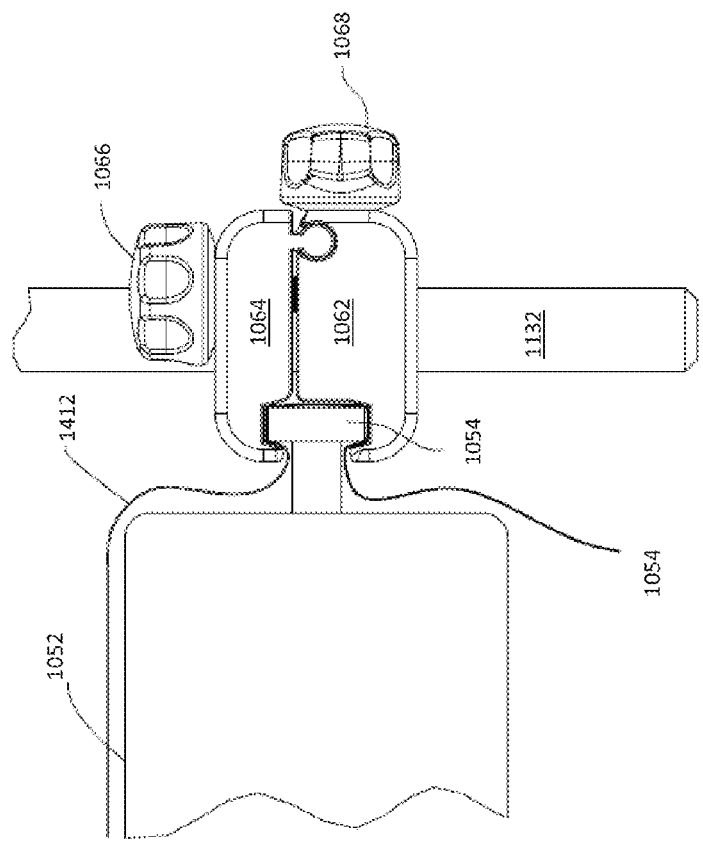
FIG. 45 is a side and partial cross sectional view depicting the clamp assembly of FIG. 17 coupled to a DIN rail over a surgical drape.

In the process of using limb holder 1050 of this invention, a surgical drape 1412, seen in FIG. 45 is first placed over the surgical table 1052 including over the DIN rail 1054. Drape 1412 provides a sterile barrier between, on one side, the table 1052, including the DIN rail 1054, and, on the other side, the patient. The patient is then placed on the table 1052, over the drape 1412. The lower and upper jaws 1062 and 1064, respectively, of clamp 1060 are then clamped over the surgical drape 1412 and over the DIN rail 1054. Clamp 1060 is positioned along the DIN rail 1054 at the location best suited to position bar 1160. Knob 1066 is tightened to releasably hold the clamp 1060 to the DIN rail 1054. Pylon 1130 is then coupled to the clamp 1060 by fitting the pylon post 1132 in the clamp jaw openings 1094 and 1114. The extent to which the pylon 1130 extends above the clamp 1060 is set based on the extent to which the practitioner wants the boot 1270 to be located above the surface of the surgical table 1052. Handle 1068 is rotated so that the handle stem 1152 press the outer portion of lower jaw 1062 against the inner section so that the pylon post 1132 is releasably clamped in the desired position.

Sled 1180 is positioned over bar 1160 so the boot 1270 in located desired by the practitioner. It should be understood that, prior to the positioning of the sled 1180, the patient's foot and leg may have already been seated in the boot 1270 and the tibial shield 1360 fitted over the leg and foot. While not illustrated, padding may be provided around the boot 1270 to prevent chaffing of the patient's foot and lower leg. Alternatively, the boot 1270 may already be attached to sled 1180. If the patient's foot and leg are in the boot and the boot is attached to the sled, when sled 1180 is moved over the bar, the surgical personnel can determine if the patient's leg will be in the appropriate position, and have the appropriate degree of flexure for the intended medical/surgical procedure.

To position sled 1180, the base 1182 is rotated around bar 1160. Sled base 1182 is rotated by pivoting one of the arms 1202. More specifically, the arm 1202 is pivoted away from the underlying surgical table 1052. The resultant rotation of the sled base 1182 results in the sled base being oriented relative to bar 1160 as is depicted in FIG. 46A. As a result of this rotation of the sled 1180, the corner between sled arcuate surface 1186 and flat surface 1190 is located adjacent bar corner 1165. Since the sled arcuate face 1186 has a radius of curvature greater than that of the bar curved surface 1162 the sled 1180, when in this position, can be freely moved over the bar 1160 to the desired position. The position of the sled 1180 can therefore be infinitesimally adjusted along the length of bar 1160.

Once the sled 1180 is in the selected positioned, the sled is rotated back to where the arms 1202 are in their at rest position over the surgical table 1052. As seen in FIG. 46B, as a result of this rotation of the sled base 1182, the corner between sled arcuate face 1186 and flat face 1188 is adjacent bar corner 1164. The center of gravity of the sled is located inward of base 1182. Consequently, the natural tendency of the sled 1180 is for the sled flat face 1186 presses against the portion of bar face 1166 adjacent corner 1164, as seen in FIG. 46B. This pressing of the sled 1180 against the bar 1160 at least initially holds the sled in the desired location over the bar.

Once sled 1180 is in the desired location, knob 1214 is rotated to secure that sled in that position. Specifically as seen by reference to FIG. 47B, the knob is rotated so the cylindrically shaped surface of knob stem section stem section 1216 presses against bar planar face 1166. More particularly, the edge surface between the notch 1219 and the outer cylindrical surface are what presses against the bar 1160. This knob stem-against-bar face abutment releasably holds the sled 1180 in the preferred location along the bar 1160. When it is necessary to again adjust the position of the sled 1180 on the bar 1160, knob 1214 is first rotated from the locked state to an unlocked state. As seen in FIG. 47A, the knob 1214 is returned to the unlocked state by rotating the knob so that the stem notch 1219 faces bar 1160. This allows the sled 1180 to be pivoted about the bar as described above.

The orientation of boot 1270 can be set along three axes. These orientations may be set consecutively or simultaneously. As part of this process, the position of yoke 1220 is set. In the following, the descriptions are of the orientation of the longitudinal axis top to bottom of the boot 1270 relative to the longitudinal axis of bar 1160.

The position of the yoke 1220 is set to establish the position of the boot along two axes. Specifically, the yoke 1220 is rotated around an axis that extends through longitudinal axis of the yoke lock 1240. This positioning of the yoke establishes, to which end or side of the surgical table boot 1270 is directed. Yoke 1220 may also be rotated around the axis that is orthogonal to the longitudinal axis through the yoke lock 1240. This rotational axis is in a plane parallel to and above the plane of surgical table 1052. The rotation of the yoke around this axis results in the tilting of the longitudinal axis of the boot through the horizontal plane across the surgical table 1052. In FIG. 16, this is the tilting of the boot 1270 so that the boot wings 1348 are either tilted towards the DIN rail 1054; at a zenith position above the surgical table 1052; or tilted away from the DIN rail. Both the rotation position and the tilt angle of the yoke 1220 relative to the sled 1180 can be infinitesimally adjusted.

Once yoke 1220 is in the desired orientation, knob 1260 is turned to releasably lock the yoke in position. Knob 1260 is rotated so as to advance stem nose 1268 into the bore 1256 internal to the yoke lock foot 1242. The handle nose 1268 abuts the adjacent ramp surface 1258 internal to the handle foot 1242. The continued advancement of the handle nose 1268 against ramp surface 1258 results in the handle downwardly displacing the yoke lock 1240 so that yoke lock head 1252 is urged towards face 1210 of sled dish 1204. Yoke 1220 is releasably compression secured in the desired position between the sled dish 1204 and yoke lock head 1252.

As mentioned above, boot posts 1282 and 1292 are able to rotate within the notches 1232 internal to the yoke arms 1230. By extension, this means the boot 1270 is able to rotate around the axis through the yoke arm notches 1232. When the yoke 1220 is set so that the longitudinal axis through the yoke arm notches 1232 is parallel to the plane of the table 1052, the rotation is the rotation of the boot around an axis that is located above and parallel with the plane of the table. Once the boot 1270 is in the desired angular position relative to yoke 1220, the boot is locked in place.

Owing to the dimensioning of the components, boot lock skirt 1314 seats in the yoke arm groove 1235. The seating of knob skirt 1314 in place by rotating the boot lock 1304 and pushing inwardly on the boot lock so that pin 1326 integral with the boot 1270 seats in the boot lock detents 1322. While spring 1328 exerts an outward force on the boot lock 1304 in this process, this force can be overcome by manual force. As a consequence of this inward movement of the boot lock 1304, toward the boot 1270 the boot lock lower skirt 1314 seats in the adjacent groove 1235 internal to the adjacent yoke arm 1230. The boot lock 1304, when in this position, is in the locked state. When the boot lock 1304 is in the locked state, skirt 1314 abuts the surface of the yoke arm 1230 that forms the base of the groove 1235. The wave spring disposed over post 1282 imposes a compressive force on the opposed boot ankle plate 1274. Collectively, the pressing of the boot lock skirt 1314 and the opposed wave spring against the opposed yoke arms 1230, hold the boot 1270 in a fixed axial position to the yoke 1220.

In the event it is necessary to remove the boot 1270 from the yoke 1220, the boot lock 1304 is rotated so that the lock can be displaced outwardly, into a release state. Spring 1328 provides a force to assist in the outward translation of the boot lock 1304. Once knob skirt 1314 is free of the yoke arm 1230, the boot can be lifted away from the yoke arm notches 1232. The boot can then be reset in the yoke arms 1230. This resetting of the boot 1270 can include the reoriented of the boot. Thus the boot can be rotated so, for example, the boot in FIG. 16 is instead of being directed to the right side of the Figure, directed to the left side. Once the boot is repositioned the boot lock is rotated so that pin 1298 resets in the detents 1322 in the knob slots 1320. Knob skirt 1314 is seated in the adjacent groove 1235. The boot 1270 is again free to rotate around the axis between the yoke arm notches 1232.

Once the boot 1270 is in the desired position, Boot lock 1304 is rotated so that pin 1326 seats in the opposed knob shaft detents 1322. The seating of pin 1326 in detents 1322 prevents the outward loosening movement of the boot lock 1304.

Limb holder 1050 of this invention provides a means to hold the limb fitted to the holder steady in a number of different positions. The limb holder 1050 makes it possible to hold the patient's limb in the position or positions the practitioner finds most useful for conducting the medical or surgical procedure.

It should be appreciated that the position of the patient may be adjusted while the limb is attached to the holder 1050 of this invention. For example, it may be desirable during a medical procedure on the leg, knee or foot to change the position of the limb. One such time when such movement may be desirable is during a procedure on the knee. As part of the procedure, the practitioner may want to bend the leg and knee between the extended (leg straight) and flexed (leg bent at the knee) states. While the patient's lower leg and foot are fitted in boot 1270, and the boot remains attached to the other components of limb holder 1050, this readjustment of the position of the patient may be performed by loosening knob 1214 and pivoting the sled 1180 so the sled can rotate relative to bar 1160. Sled 1180, can then be moved along the bar 1160. The movement of the sled 1180 and attached boot 1270 as well as the patient's lower leg and foot results in the desired flexing or straightening of the leg. It should be understood that during this flexing of the leg, boot 1270 will rotate as appropriate around the axis between the yoke arm notches 1232.

Once the leg is bent to the desired position, the sled is rotated back to the locked state. As a result of this rotation of the sled 1180, the sled is at last initially locked against the bar 1160. Knob 1214 is rotated against the bar 1160 to provide a more robust locking of the sled 1180 to the bar.

During the procedure, retractors 1390 hold an incision open. Straps 1402 hold the retractors to boot 1270. This feature of the invention eliminates the need to have surgical personnel stand adjacent the incision solely to hold the retractors in place.

Still another benefit of limb holder 1050 is that the position of bar 1160 can be selectively set. By extension this makes it possible to position the boot 1270 in a number of different locations relative to the surgical table 1052. For example, instead of positioning the bar 1160 so that the bar substantially overlies the DIN rail 1054, the bar can be locked to the pylon 1130 to extend outwardly away from the DIN rail 1054. If FIG. 16 was redrawn to show the bar 1160 in this position, the bar would extend outwardly away from the table 1052.

It should also be appreciated that, boot 1270, with the patient's leg mounted to it may be removed from the rest of the limb holder 1050. Thus, during a procedure, the practitioner can remove the boot 1270 with the leg still attached in order to perform some flexure of the hip, leg or knee. Then, the practitioner can refit the boot, with the leg still attached, to the limb holder. During this removal and reattachment of the boot 1270 from the other components of limb holder 1050, the positions of the other components of the limb holder need not be disturbed. This means that after the practitioner has performed the desired flexing of the patient, the leg can be returned to the same position in which it was in prior to the flexing. Alternatively, as a result of the repositioning of the sled 1180 and/or reorientation of the yoke 1220, when the boot is reattached to the rest of the limb holder 1050, the boot and leg are in a new position.

As described above the mechanism that hold the components of limb holder 1050 to each other are constructed to allow infinitesimally small adjustment of the positions/orientations of these components relative to each other. The practitioner is not limited to step adjustments of the position/orientation of these components. By extension the practitioner is therefore not limited to the stepped adjustment of the limb captured by the limb holder. Instead the position and orientation of the limb can, the components holding the limb, be infinitesimally adjusted.

The foregoing is directed to one specific version of the limb holder of this invention. Other versions of the invention may have features different from what has been described.

For example, a limb holder of this invention designed to hold the arm in position will have a frame shaped to receive the arm different from the described boot 1270. The limb holding frame of these versions of the invention may be in the form of an elongated shell that, in cross section, appears semi-circular.

Likewise, the features of the invention may vary from what has been described. There is no requirement that the locking members that releasably hold the components of this assembly to each other be the described knobs with threaded shafts. In some versions of the invention, spring biased clamps may be employed to releasably hold the components of the assembly to each other.

In some versions of the invention, the clamp may not have a jaw that clamps over the pylon post 1132. Instead, a knob with a threaded stem may press against the pylon post 1132 in order to releasably hold the pylon at a select height relative to the clamp 1060. Similarly, in some versions of the invention, bar 1160 may be adjustably mounted to the pylon 1130. In these versions of the invention, a knob with a stem or a lever may be movably mounted to the head of the pylon. The knob stem or lever is configured to selectively abut the bar 1160 to hold the bar in a fixed position to the pylon head.

Likewise, in some versions of the invention the stem of the knob that holds the sled in position may have an end surface that simply presses against a complementary face of the bar to which the sled is mounted.

Similarly, in alternative versions of the invention, the sled may be provided with other features that allow the sled to move freely longitudinally and, when set in position, from being restrained from further movement. For example, ball bearings may be mounted to the sled so as to project into the bore in which the bar is seated. A pawl is moveably mounted to the sled to engage the bar. When it is desirable to reposition the sled, the pawl is moved to a disengaged state. The ball bearings allow the sled to freely move over the bar. Once the position of the bar is reset, the pawl is reset to an engaged state. When in the engaged state, the pawl engages a portion of the bar to prevent further movement of the sled.

The clamp assembly may be designed to be secured to another feature of the surgical table 1052. This is required in versions of the invention designed for use with tables that do not have DIN rails. Thus, in some versions of the invention, the limb holder may be a stand alone unit, separate from the bed. In these versions of the invention, the limb holder may, instead of a clamp and a pylon, include a base from which a post extends. The bar extends outwardly from the base.

It should similarly be appreciated that alternative versions of the invention may include features that provide the components fewer degrees of freedom than in the described version. For example, there is no requirement that in all versions of the invention that it is necessary to provide a bar-holding pylon 1130 able to move vertical relative to the component to which the pylon is attached. Similarly, in some versions of the invention it may be desirable to provide the pylon with a head that rotates. Specifically it may be desirable to provide the pylon with a head that rotates in the plane perpendicular to the longitudinal axis of the pylon. In these versions of the invention, the pylon could then be rotated to set the bar 1160 so that the bar extends over or away from the surgical table 1052. This positioning of the bar would allow the limb-holding frame to be positioned towards the center of the table 1052 or away from the table edge.

Generally, it is believed that limb holder of this invention has features that allow the limb holding frame to move linearly along at least one axis and rotationally around at least two axes. Also, in some versions of the invention one or more structural units may be able to both move linearly and be able to rotate relative to the structural unit to which it is attached.

In some versions of the invention, bar 1160 may be eliminated. In these versions of the invention, the sled and attached components are attached directly to the clamp or pylon. While these versions of the invention may have less utility than the primary described version, the reduction in components reduces the costs of providing these versions of the invention.

Also, it may be desirable to attach limb holder 1050 to the surgical table so the limb holder is disposed over both the inner drape between the surgical table 1052 and the patient and the outer drape disposed over the patient.

Further, there is no requirement that in all versions of the invention, a flexible shield be used to restrain the movement of the limb in the frame. In alternative versions of the invention, simple straps that extend across the frame may hold the limb in place. This arrangement may be useful when the procedure is being performed on the limb fitted to the frame. In some versions of the assembly, a rigid shell may be used to hold the limb to the frame. This is useful if there is need to essentially prevent any movement of the limb in the frame.

Further the limb-holding frame may be provided with features other than posts for releasably holding surgical tools to the frame. These alternative features can include clips designed to hold surgical instruments. The frame may also be provided with notches to hold the instruments. Thus, the limb holder of this invention may be have features to hold instruments other than those with flexible straps.

In some versions of the invention, the shield that extends of the frame-encased limb and the straps that hold the shield to the frame are formed from a single piece of material. This eliminates the need to provide fasteners or stitching to hold the straps to the shield.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A limb positioning device comprising:
a clamp attachable to a patient support;
a first support member configured to connect to the clamp;
a second support member slidingly coupled to the first support member;
a limb holder polyaxially and detachably coupled to the second support member; and
a support wing attached to and extending from the limb holder, the support wing having a retractor attachment portion including a plurality of discrete, spaced apart attachment features disposed thereon and positioned on both a medial and lateral side of the limb holder for coupling a retractor to the support wing, the retractor being configured to hold an incision open.

2. The limb positioning device of claim 1, further comprising a tracking system for use with a navigation system, wherein a component of the tracking system is mountable to the support wing.

3. The limb positioning device of claim 1, wherein the first support member further comprises:

a post connected to the clamp; and an elongate bar providing a track along which the second support member can slide.

4. The limb positioning device of claim 3, wherein the second support member includes a ball and socket assembly.

5. The limb positioning device of claim 4, wherein the second support member includes a second lock configured to be in one of a locked state in which the ball is capable of zero degrees of movement with respect to the second support member and an unlocked state in which the ball is capable of at least two degrees of movement with respect to the second support member.

6. The limb positioning device of claim 4, wherein the ball is configured to attach the limb holder to the second support member.

7. The limb positioning device of claim 6, wherein the limb holder is capable of three degrees of freedom of movement with respect to the second support member.

8. The limb positioning device of claim 3, wherein the second support member includes a first lock biased by at least one spring to a locked state with respect to the elongate bar in which the second support member cannot slide along the elongate bar.

9. The limb positioning device of claim 8, wherein, upon application of force, the first lock is configured to change from the locked state to an unlocked state with respect to the elongate bar in which the second support member can slide along the elongate bar.

10. The limb positioning device of claim 3, wherein the elongate bar comprises a first portion and a second portion, one of the first portion and second portion configured to be coupled to the post, and the first portion configured to be coupled to the second portion.

11. The limb positioning device of claim 10, wherein the elongate bar further includes a coupling mechanism, the coupling mechanism comprising a protrusion on one end of the first portion and a slot in one end of the second portion, the slot configured to accept the protrusion.

12. The limb positioning device of claim 1, wherein the limb holder is infinitesimally adjustable in six degrees of movement with respect to the clamp.

13. The limb positioning device of claim 1, further comprising a retractor coupled to the support wing, the retractor configured to hold an incision open.

14. The limb positioning device of claim 1, wherein at least a portion of the support wing is at least partially circular with a virtual center configured to align with a center of a joint of a limb positioned in the limb holder.

15. A limb positioning assembly comprising;

a clamp;

a support post connectable to the clamp and infinitesimally adjustable in at least one degree of movement with respect to the clamp;

a rail connectable to the support post;

a support assembly connectable to the rail and infinitesimally adjustable with respect to the rail in at least one degree of movement;

a limb holder detachably connectable to the support assembly and infinitesimally adjustable with respect to the support assembly in at least three degrees of movement; and a support wing attached to and extending from the limb holder, the support wing having a retractor attachment portion including a plurality of discrete, spaced apart attachment features disposed thereon and positioned on at least one of a medial and lateral side of the limb holder for coupling a retractor to the support wing, the retractor being configured to hold an incision open.

* * * * *